(12) United States Patent
Kay

(10) Patent No.: US 8,895,610 B1
(45) Date of Patent: *Nov. 25, 2014

(54) PLATINUM (IV) COMPOUNDS TARGETING ZINC FINGER DOMAINS

(76) Inventor: Heldi Kay, Springfield, VA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/011,613

(22) Filed: Jan. 21, 2011

Related U.S. Application Data

(63) Continuation-in-part of application No. 12/122,855, filed on May 19, 2008, now Pat. No. 8,026,382.

(60) Provisional application No. 61/336,360, filed on Jan. 21, 2010, provisional application No. 60/938,781, filed on May 18, 2007.

(51) Int. Cl.
*A61K 31/28* (2006.01)

(52) U.S. Cl.
USPC .......................................................... 514/492

(58) Field of Classification Search
USPC .......................................................... 514/492
See application file for complete search history.

(56) References Cited

U.S. PATENT DOCUMENTS

| | | | |
|---|---|---|---|
| 4,716,157 A | 12/1987 | Bitha et al. | |
| 5,849,790 A | 12/1998 | Palmer et al. | |
| 6,113,934 A | 9/2000 | Farrell et al. | |
| 6,313,333 B1 | 11/2001 | Da Re et al. | |
| 6,426,093 B1 | 7/2002 | Chevion et al. | |
| 6,630,172 B2 | 10/2003 | Batarsah | |
| 6,939,566 B2 | 9/2005 | Bataresh et al. | |
| 6,989,157 B2 | 1/2006 | Gillis et al. | |
| 7,238,372 B2 | 7/2007 | Turkson et al. | |
| 7,445,764 B1 | 11/2008 | Kratz | |
| 7,566,798 B2 | 7/2009 | Kay et al. | |
| 7,759,510 B2 | 7/2010 | Kay et al. | |
| 7,763,585 B2 | 7/2010 | Turkson et al. | |
| 7,943,600 B2 | 5/2011 | Froim et al. | |
| 7,977,381 B2 | 7/2011 | Kay et al. | |
| 7,977,500 B2 | 7/2011 | Kay et al. | |
| 8,026,382 B2 | 9/2011 | Kay | |
| 8,247,445 B2 | 8/2012 | Kat et al. | |
| 8,338,454 B2 | 12/2012 | Menon | |
| 8,455,543 B2 | 6/2013 | Kay et al. | |
| 2004/0209836 A1 | 10/2004 | Spencer et al. | |
| 2005/0074502 A1 | 4/2005 | Turkson | |
| 2005/0080131 A1* | 4/2005 | Kay et al. ..................... 514/492 |
| 2005/0288365 A1 | 12/2005 | Kay et al. | |
| 2007/0065888 A1 | 3/2007 | Ring et al. | |
| 2007/0161613 A1 | 7/2007 | Kay | |
| 2008/0187992 A1 | 8/2008 | Turkson | |
| 2008/0286316 A1 | 11/2008 | Kay | |
| 2009/0136590 A1 | 5/2009 | Plotnikov | |
| 2009/0214626 A1 | 8/2009 | Kay | |
| 2009/0275099 A1 | 11/2009 | Glick | |
| 2009/0285884 A1 | 11/2009 | Kay | |
| 2009/0324743 A1 | 12/2009 | Carter | |
| 2010/0104645 A1 | 4/2010 | Ali et al. | |
| 2010/0216801 A1 | 8/2010 | Dhanak et al. | |
| 2010/0310645 A1 | 12/2010 | Turkson | |
| 2010/0316704 A1 | 12/2010 | Kay | |
| 2011/0021483 A1 | 1/2011 | Du Preez | |
| 2011/0027255 A1 | 2/2011 | Ferrari | |
| 2011/0236471 A1 | 9/2011 | Kay | |
| 2011/0293565 A1 | 12/2011 | Kandimalla et al. | |
| 2012/0189537 A1 | 7/2012 | Menon | |
| 2013/0011419 A1 | 1/2013 | Chari et al. | |
| 2013/0122114 A1 | 5/2013 | Golan et al. | |

OTHER PUBLICATIONS

Kelland et al, "A Novel trans-Platinum Coordination Complex Possesing in Viro and in Vovo Antitumor Activity", Cancer Research, vol. 54, pp. 5618-5622, Nov. 1, 1994.*

Anzellotti et al., Supplemental Data—Targeting retroviral Zn finger-DNA interatcions: A small molecule approach using the electrophilic nature of trans-platinum-nucleobase compounds.

Anzellotti et al., Covalent and noncovalent interactions for [Metal(dien)nucleobase]2+ complexes with I-tryptophan derivatives; formation of palladium-tryptophan species by nucleobase substitution under biologically relevant conditions, Inorganic Chemistry, vol. 45, No. 4, 2006.

Arnesano et al., Mechanistic insight into the inhibition of matrix metalloproteinases by platinum substrates, J. Me. Chem, 2009, 52, pp. 7847-7855.

Banks et al., Permeability of the blood-brain barrier to HIV-1 Tat, Experimental Neurology, 193 (2005), pp. 218-227.

Barabas et al., Cisplatin: a review of toxicities and therapeutic applications, Department of Small Animal Clinical Sciences, College of Veterinary Medicine, University of Florida, Gainesville, FL, USA, Journal Compilation, 2008.

Bose, Biomolecular Targets for Platinum Antitumor Drugs, Mini Reviews in Medicinal Chemistry, 2002, 2, pp. 103-111.

Campbell et al., What does the structure-function relationship of the HIV-I Tat protein teach us about developing an AIDs vaccine, Retrovirology, 2009, 6:50.

Anzellotti et al., Zinc metalloproteins as medicinal targets, Chem. Soc. Reb., 2008, 37, pp. 1629-1651.

Caputo et al., HIV-1 Tat-Based Vaccines: An overview and perspectives in the field of HIV/AIDS vaccine development, International Reviews of Immunology, 28:285-334, 2009.

Chandra et al., Molecular interactions of the type 1 human immunodeficiency virus transregulatory protein TAT with N-Methyl-D-Aspartate receptor subunits, Neuroscience 134, (2005), pp. 145-153.

Cruceanu et al., Nucleic acid binding and chaperone properties of HIV-1 gag and nucleocapsid proteins, Nucleic Acids Research, 2006, vol. 34, No. 2, pp. 593-605.

(Continued)

*Primary Examiner* — Elli Peselev
(74) *Attorney, Agent, or Firm* — Allen, Dyer, Doppelt, Milbrath & Gilchrist, P.A.

(57) ABSTRACT

This application pertains to compositions and use of platinum (IV) compounds to alter zinc-binding sites, zinc-binding domains, zinc metalloproteins or zinc-associated proteins. Such interactions alter specific activities of these zinc-binding sites and associated protein functions, therefore offering therapeutic value.

2 Claims, 10 Drawing Sheets

(56) References Cited

OTHER PUBLICATIONS

Gorelick et al., Strict Conversation of the Retroviral Nucleocapsid Protein Zinc Finger is Strongly Influenced by its Role in Viral Invection Processes: Characterization of HIV-1 particles Containing Mutant Nucleocapsid Zinc-Coordinating Sequences, Virology, 256, 1999, pp. 92-104.

Khan et al., Nucleic Acid Binding Properties of Recominant Zn2 HIV-1 Nucleocapsid Protein Are Modulated by COOH-terminal Process,ing, the Journal of Biological Chemistry, vol. 269, No. 36, Issue of Sep. 9, 1994, pp. 22538-22546.

Kesel, A System of protein target sequences for anti-RNA-viral chemotherapy by a vitamin B6-derived zinc-chelating trioxa-adamantane-triol, Bioorganic & Medicinal Chemistry 11, 2003, pp. 4599-4613.

Hamberger, et al., Characterization of chemosensitivity and resistance of human cancer cell lines to platinum (II) versus platinum (IV) anticancer agents, Anti-cancer Drugs, 2009, 20, pp. 559-572.

Gil et al., Recombinant nucleocapsid-like particles from dengue-2 virus induce protective CD4+ and CD8+ cells against viral encephalitis in mice, International Immunology, vol. 21, No. 10, pp. 1175-1183, 2009.

Greenstone et al., Chimeric papillomavirus virus-like particles elicit antitumor immunity against the E7 oncoprotein in an HPV16 tumor model, Proc. Natl. Acad. Sci. USA, vol. 95, pp. 1800-1805, Feb. 1998.

Fruh et al., Immune evasion by a novel family of viral PHD/LAP-finger proteins of gamma-2 herpesviruses and poxviruses, Virus Research 88, 2002, pp. 55-69.

Manrique et al., Functional domains in the feline immunodeficiency virus nucleocapsid protein, Virology 327, 2004, pp. 83-92.

Galanski et al., Recent Developments in the Field of Tumor-Inhibiting Metal Complexes, Current Pharmaceutical Design, 2003, 9, pp. 2078-2089.

Larabee et al., Mechanisms of inhibition of zinc-finger transcription factors by selenium compounds ebselen and selenite, Journal of Inorganic Biochemistry 103, 2009, pp. 419-426.

Garcia et al., Characterization of Junin virus particles inactivated by a zinc finger-reactive compound, Virus Research 143, 209, pp. 106-113.

Jeong et al., Immunicatioin with hepatitis C Virus-like particles induces humoral and cellular immune responses in nonhuman primates, Journal of Virology, Jul. 2004, pp. 6995-7003.

Kang et al., Influenza vaccines based on virus-like particles, Virus Res., 143(2); pp. 140-146, Aug. 2009.

Kang et al., Induction of Long-Term Protective Immune Responses by Influenza H5N1 Virus-Like Particles, PLOS One, Mar. 2009, Vo.4, Issue 3.

Kang et al., Regulation of hepatitis C virus replication by the core protein through its interaction with viral RNA polymerase, Biochemical and Biophysical Research Communications 386, 2009, pp. 55-59.

Marcotrigiano et al., Purification and Crystallization NS5A Domain I of Hepatitis C Virus, Hepatitis C: Methods and protocols, Second Edition, Vo. 510, 2009, Chapter 7.

Markovic et al., [Pt(HPxSC)C13], a novel platinum (IV) compound with anticancer properties, European Journal of Phamacology, 517, 2005, pp. 28-34.

Larabee et al., Mechanisms of inhibition of zinc-finger transcription factors by selenium compounds ebselen and selenite, Journal of Inorganic Chemistry, 103, 2009, pp. 419-426.

Russian literature by I.I. Cernjaev, Izv. Plat. 8, 1931; 55-71.

Pushko et al., Influenza virus-like particles comprised of the HA, NA, and M1 proteins of H9N2 influenza virus induce protective immune responses in BALB/c mice, Vaccine 23 (2005), pp. 5751-5759.

Peritiz et al., Antitumor and DNA-Binding Properties of a Group of Oligomeric Complexes of Pt(II) and Pt(15), J. Med. Chem., 1990, 33, pp. 2184-2188.

Paliard et al., Priming of Strong, Broad and Long Lived HIV Type 1 p55gag-Specific CD8+ Cytotoxic T Cells after Administration of a Virus-Like particle Vaccine in Rhesus Macaques, Aids Research and Human Retroviruses, vol. 16, No. 3, 2000, pp. 273-282.

Ottmann et al., The Central Globular Domain of the Nucleocapsid Protein of Human Immunodeficiency Virus Type 1 is Critical for Viron Structure and Infectivity, Journal of Virology, Mar. 1995, pp. 1778-1784.

New et al., Investigations using fluroescent ligands to monitor platinum (IV) reduction and platinum (II) reactionis in cancer cells, Dalton Trans., 2009, pp. 3092-3101.

Murata et al., Immunication with hepatitis C virus-like particles protects mice from recombinant hepatitis C virus-vaccinia infection, PNAS, May 27, 2003, vol. 100, No. 11, pp. 6753-6758.

Tellinghuisen et al., The NS5A protein of hepatitis C Virus is a Zinc metalloprotein, The Journal of Biological Chemistry, vol. 279, No. 47, (2004), pp. 48576-48587.

Tedbury et al., Characerisation of the Role of Zinc in the Hepatitis C Virus NS2/3 Auto-cleavage and NS3 protease Activities, J. Mol, Biol. (2007), 366,pp. 1652-1660.

Tallant et al., Matrix metalloproteinases: Fold and function of their catalytic domains, Biochimica et Biophysica Acta 1803 (2010), pp. 20-28.

Tacket et al., Humora, musocal, and cellular immune responses to oral Norwalk virus-like particles involunteers, Clinical Immunology 108, (2003), pp. 241-247.

Sugrue et al., Expression of the dengue virus structural proteins in *Pichia pastoris* leads to the generation of virus-like like particles, Journal of General Virology (1997), 78, pp. 1861-1866.

Storni et al., Nonmethylated CG motifs packaged into virus-like particles induce protective cytotoxic T cell responses in the absence of systemic side effects, The Journal of Immunology, 2004, 172, pp. 1777-1785.

Morellet et al., Conformational Behaviour of the Active and Inactive Forms of the Nucleocapsid NCp7 of HIV-1 studied by 1H NMR, J. Mol. Biol., 1994, 235, pp. 287-301.

Jaeschke et al., Function Follows Form: The structure of the N-Terminal Domain of HCV NS5A, Hepatology Elsewhere, Nature 2005, 435, pp. 374-379.

Misumi et al., Zn2+ Binding to Cysteine-Rich Domain of Extracullar Human Immunodeficiency Virus Type 1 Tat Protein is Associated with Tat Protein-Induced Apoptosis, AIDS Research and Human Retroviruses, vol. 20, pp. 297-304, 2004.

Mellor et al., The influence of tumour microenvironmental factors on the efficacy of cisplatin and novel platinum (IV) complexes, Biochemical Pharmacology, 70, 2005, pp. 1137-1146.

Wingard et al., Induction of HIV-specific T and B Cell Responses with a replicating and conditionally infectious lentiviral vaccine, Eur. J. Immunol. 2008, 38, pp. 1310-1320.

Williams et al., Specific zinc-finger architecture required for HIV-1 nucleocapsid protein's nucleic acid chaperone function, PNAS, Jun. 25, 2002, vol. 99, No. 13, pp. 8614-8619.

Maynard et al., Reactivity of Zinc Finger Cores: Analysis of Protein packing and Electrostatic Screening, J. Am. Chem. Soc., 2001, 123, pp. 1047-1058.

Masarenhas et al., The capsid protein of human immunodeficiency virus: interactions of HIV-1 capsid with host protein factors, FEBS Journal, 276, 2009, pp. 6118-6127.

Morellet et al., Structure of the Complex between the HIV-1 Nucleocapsid Protein NCp7 and the single-stranded pentanucleotide d(ACGCC), J. Mol. Biol. (1998), 283, pp. 419-434.

Lindwasser et al., Human Immunodeficiency Virus Type 1 Gag Contains a Dileucine-Like Motif That Regulates Association With Multivesicular Bodies, Journal of Virology, Jun. 2004, pp. 6013-6023.

Thomas et al., Mutations inhuman immunodeficiency virus type 1 nucleocapsid protein zinc fingers cause premature reverse transcription, Journal of Virology, Oct. 2008, pp. 9318-9328.

Tortorici et al., Zinc binding properties of Junin virus nucleocapsid protein, Journal of General Virology, 2001, 82, pp. 121-128.

Li et al., Role to Tat Protein in HIV Neuropathogenesis, Neurotox Res, 2009, 16, pp. 205-220.

Shresta et al., Early activation of natural killer and B cells in response to primary dengue virus infection in A/J mice, Virology 319, 2004, 262-273.

(56) References Cited

OTHER PUBLICATIONS

Seve et al., The human immunodeficiency virus-1 Tat protein increases cell proliferation, alters sensitivity to zinc chelator-induced apoptosis, and changes SP1 DNA binding in HeLa cells, Archives of Biochemistry and Biophysics, vol. 361, No. 2, Jan. 15, 1999, pp. 165-172.

Sedlik et al., Recombinant parvorius-like particles as an antigen carrier: A novel nonreplicative exogenous antigen to elicit protective antiviral cytotoxic T cells, Proc. Natl, Acad. Sci. USA, vol. 94, pp. 7503-7508, Jul. 1997.

Saini et al., A Japanese encephalitis virus peptide present on Johnson grass mosaic virus-like particles induces virus-neutralizing antibodies and protects mice against lethal challenge, Journal of Virology, Mar. 2003, pp. 3487-3494.

Manrique et al., Functional relationship between the matrix proteins of feline and simian immunodeficiency viruses, Virology 329, 2004, pp. 157-167.

Manicone et al., Matrix Metalloproteinases as modulators of inflammation, Semin Cell Div Biol., 2008, 19(1), pp. 34-41.

Liang et al., A Novel CCCH-Zinc finger protein family regulates proinflamatory activation of macrophages, The Journal of Biological Chemistry, vol. 283, No. 10, pp. 6337-6346, Mar. 7, 2008.

Liang et al., Domain 2 of Nonstructural Protein 5A (NS5A) of Hepatitis C Virus is Natively Unfolded, Biochemistry 2007, 46, pp. 11550-11558, Apr. 24, 2007.

Luttge et al., FIV Gag: Virus assembly and host-cell interactions, Veterinary Immunology and Immunopathology 134, 2010, pp. 3-13.

Larabee et al., Inhibition of zinc finger protein-DNA interactions by sodium selenite, Biochemical Phamacology 64, 2002, pp. 1757-1765.

Guo et al., Zinc Finger Structures in the human immunodeficiency virus type 1 nucleocapsid protein facilitate efficient minus- and plus-strand transfer, Journal of Virology, Oct. 2000, pp. 8980-8988.

Ivanov et al., Cisplatin Binding Sites on Human Albumin, The Journal of Biochemistry, vol. 273, No. 24, Issue of Jun. 12, 1998, pp. 14721-14730.

Ishida et al., Prominent stacking interaction with aromatic amino acid by N-quarternization of nucleic acid base: X-ray crystallographic characteristics and biological implications, Archives of Biochemistry and Biophysics, vol. 2178, No. 1, Apr. 1990, pp. 217-227.

Heinz et al., Structural adaptability of zinc binding sites: different structures in partially, fully, and heavy-metal loaded states, Chem. Eur. J., 2009, 15, pp. 7350-7358.

Kratochwil et al., Relationships between Reduction properties and cancer cell growth inhibitory activities of cis-Dichloro-and-cis-Diiodo-Pt(IV)-ethylenediamines, Arch. Pharm. Pharm. Med. Chem., 1999.

Koellensperger et al., Characterisation of zinc-binding domains of peroxisomal RING finger proteins using size exclusion chromatography/inductively coupled plasma-mass spectrometry, Biol. Chem. vol. 388, pp. 1209-1214, Nov. 2007.

King et al., HIV tat and neurotoxicity, Microbes and Infections 8, 2006, pp. 1347-1357.

Kim et al., Caveolin-1 inhibits membrane-type 1 matrix metalloproteinase activity, Department of Biotechnology, Hannam University, Daejeon, 305-811, 2008.

Harney et al., Targeted inhibition of Snail family zinc finger transcription factors by oligonucleotide-Co(III) Schiff base conjugate, PNAS, Aug. 18, 2009, vol. 106, No. 33, pp. 13667-13672.

Huang, Structural characterization of the metal binding site in the cysteine-rich region of HIV-1 Tat protein, Biochemical and Biophysical Research Communication, 227, pp. 615-621, 1996.

Houzet et al., Nucleocapsid mutations turn HIV-1 into a DNA-containing virus, Nucleic Acids Research, 2008, vol. 36, No. 7, pp. 2311-2319.

Houzet et al., Intracellular assembly and budding of the Murine Leukemia Virus in infected cells, Retrovirology, 2006, 3: 12.

Joshi et al., Evidence that productive human immunodeficiency virus type 1 assembly can occur in an intracellular compartment, Journal of Virology, Jun. 2009, pp. 5375-5387.

Jacobsen et al., The Design of Inhibitors for Medicinally Relevant Metalloproteins, ChemMedChem, 2007, 2, pp. 152-171.

Gorelick et al., Nucleocapsid protein zinc-finger mutants of simian immunodeficiency virus strain Mne produce virons that are replication defective in Vitro and in Viro, Virology, 253, 1999, pp. 259-270.

Song et al., A20 is an antigen presentation attenuator, and its inhibition overcomes regulatory T cell-mediated suppression, Nature Medicine, vol. 14, No. 3, Mar. 2008.

Van Lint, et al., Chemokine and cytokine processing by matrix metalloproteniases and its effect on leuklcyte migration and inflammation, Journal of Leukocyte Biology, vol. 82, Dec. 2007.

Wadia et al., Transmembran delivery of protein and peptide drugs by TAT-mediated Transduction in the treatment of cancer, Advanced Drug Deliver Reviews, 57, 2005, pp. 579-596.

Warfield et al., Ebola virus-like particles protect from lethal Ebola virus infection, PNAS, vol. 100, No. 26, Dec. 23, 2003.

Webster et al., Matrix metalloproteinases, their production by monocytes and macrophages and their potential role in HIV-related diseases, Journal of Leukocyte Biology, vol. 80, Nov. 2006.

Younce et al., (Monocyte Chemotactic Protein-1)-induced Protein, a Recently Identified Zinc Finger Protein, Induces Adipogenesis in 3T3-L1 Pre-adipocytes without Peroxisime Proliferator-activated Receptor y, Journal of Biological Chemistry, vol. 284, No. 40, Oct. 2, 2009.

Yu et al., Caveolin-I interacts with the Gag precursor murine leukaemia virus and modulates virus production, Virology Journal, published Sep. 6, 2006.

Stevenson et al., Inhibitioin of MHC class I-restricted antigen presentation by y2-herpesviruses, Immunology, Jul. 18, 2000, vol. 97, No. 15, pp. 8455-8460.

Thomas et al., Nucleocapsid protein function in early infection processes, Virus Res, Jun. 2008, 134(1-2) pp. 39-63.

Zhong et al., Caveolin-1 regulates HIV-1 TAT-induced alteratioins of tight junction protein expression via modulation of the RAS signaling, J Neurosci., Jul. 2008, 28(31), pp. 7788-7796.

Zucker et al., Tissue inhibitor of metalloproteinase-2 (TIMP-2) binds to the catalytic domain of the cell surface receptor, membrane type 1-matrix metalloproteinase 1 (MT1-NMM), The Journal of Biological Chemistry, vol. 273, No. 2, Jan. 9, 1998, pp. 1216-1222.

Alvarez-Lajonchere et al., Hepatic C virus (HCV core protein enhances the immunogenicity of a co-delivered DNA vaccine encoding HCF structural antigens in mice, Biotechnol. Appl. Biochem (2006), 44, pp. 9-17.

Amalinei et al., biology of metalloproteinases, Romanian Journal of Morphology and Embryology, 2007, 48(4) pp. 323-334.

Amexis et al., Multiple antigenic peptides as vaccine platform for the induction of humoral responses against dengue-2 virus, Viral Immunology, vol. 20, No. 4, 2007, pp. 657-663.

Andras et al., HIV-1 Tat protein alters tight junction protein expression and distribution in brain endothelial cells, Journal of Neuroscience Research, 74, pp. 255-265, 2003.

De Francesco, et al., Mechanisms of hepatitis C virus NS3 proteinase inhibitors, Journal of Viral Hepatitis, 1999, 6 (Suppl. 1) pp. 23-30.

Deniaud et al., Overexpression of transcription of factor Sp 1 leads to gene expression of perturbations and cell cycle inhibition, Plos one, Sep. 2009, vol. 4, Issue 9.

Bose et al., Non-DNA-binding platinum anticancer agents: cytotoxic activities of platinum-phosphato complexes towards human ovarian cancer cells, PNAS, Nov. 25, 2008, vol. 105, No. 47.

Bednarski et al., Photoactivatable platinum complexes, Anti-Cancer Agents in Medicinal Chemistry, 2007, vol. 7, pp. 75-93.

Berthoux et al., Mutations in the N-terminal domain of human immunodeficiency virus type 1 nucleocapsid protein affect virion core structure and proviral DNA synthesis, Journal of Virology, Sep. 1997, pp. 6973-6981.

Brayer et al., Keep your fingers off my DNA: protein-protein interactions mediated by C2H12 zinc finger domains, Cell Biochem Biophys (2008) 50:111-131.

dE Paula et al., Zinc finger proteins as templates for metal ion exchange: substitution effects on the C-finger of HIV nucleocapsid NCp7 M(chelate) species (M=Pt, Pd, Au), Journal of Inorganic Biochemistry 103, (2009), pp. 1347-1354.

(56) References Cited

OTHER PUBLICATIONS

Cruceanu et al., Rapid Kinetics of protein-nucleic acid interaction is a major component of HIV-1 nucleocapsid protein's nucleic acid chaperone function, J. Mol. Biol (2006), 363, pp. 867-877.

Campbell et al., In Vitro assembly properties of human immunodeficiency virus typ 1 gag protein lacking the p6 domain, Journal of Virology, Mar. 1999, pp. 2270-2279.

Campbell et al., Lipid rafts and HIV-1: from viral entry to assembly of progeny virions, Journal of Clinical Virology 22, (2001), pp. 217-227.

Didierlaurent et al., The conserved N-terminal basic residues and zinc-finger motifs of HIV-1 nucleocapsid restrict the viral cDNA synthesis ruing virus formation and maturation, Nucleic Acids Research, 2008, vol. 36, No. 14, pp. 4745-4753.

Egele et al., Modulation of microtubule assembly by the HIV-1 tat protein is strongly dependent on zinc binding to Tat, Retrovirology, 2008, 5:62.

De Rocquigny et al., Targeting the viral nucleocapsid protein in anti-HIV-1 therapy, Mini-Reviews in Medicinal Chemistry, 2008, 8, pp. 24-35.

Estrada et al., The hantavirus glycoprotein G1 tail contains dual CCHC-type classical zinc fingers, The journal of Biological Chemistry, vol. 284, No. 13, pp. 88654-8660, 2009.

Elkington et al., Analysis of matrix metalloproteinase secretion by macrophages, Macrophages and Dendritic Cells, Methods in Molecular Biology, vol. 531, 2009.

Elmowalid et al., Immunization with hepatitis C virus-like particles results in control hepatitis C virus infection in chimpanzees, PNAS, May 15, 2007, vol. 104, No. 20, pp. 8427-8432.

Didierlaurent et al., The conserved N-terminal basic residues and zinc-finger motifs of HIV-1 nucleocapsid restrict the viral cDNA synthesis during virus formation and maturation, Nucleic Acids Research, 2008, vol. 36, No. 14, pp. 4745-4753.

Ding et al., Inhibitioin of Poly(ADP-ribose) polymerase-1 by arsenite interferes with repair of oxidative DNA damage, The Journal of Biological Chemistry, vol. 284, No. 11, pp. 6809-6817, 2009.

Enterlein et al., Rescue of recombinant marburg virus from cDNA is dependent of nucleocapsid protein VP 30, Journal of Virology, Jan. 2006, pp. 1038-1043.

Adamson et al., Virus Maturation as a novel HIV-1 therapeutic target, Expert Opin Ther Targets, Aug. 2009, 13 (8) pp. 895-908.

Sadeyen et al., Insertion of a foreign sequence on capsid surface loops of human papillomarvius type 16 virus-like particles reduces their capacity to induce neutralizing antibodies and delineates a conformational neutralizing epitope, Virology 309, (2003), pp. 32-40.

Riedl et al., Binding immune-stimulation oligonucleotides to cationic peptides from viral core antigen enhances their ptoency as adjuvants, Eur. J. Immunol, 2002, 32, pp. 1709-1716.

Riedl et al., Priming Th1 immunity to viral core particles is facilitated by trace amounts of RNA bound to its arginine-rich domain, The Journal of Immunology, 2002, 168, pp. 4951-4959.

Rappport et al., TAT-based drug delivery system—new directions in protein delivery for new hopes, Informa Healthcare, 2009.

* cited by examiner

Fig. 4A Control (Unexposed)

Fig. 4B Exposed to 10 Micromolar Platinum(IV) Compound

Fig. 4C Exposed to 20 Micromolar Platinum(IV) Compound

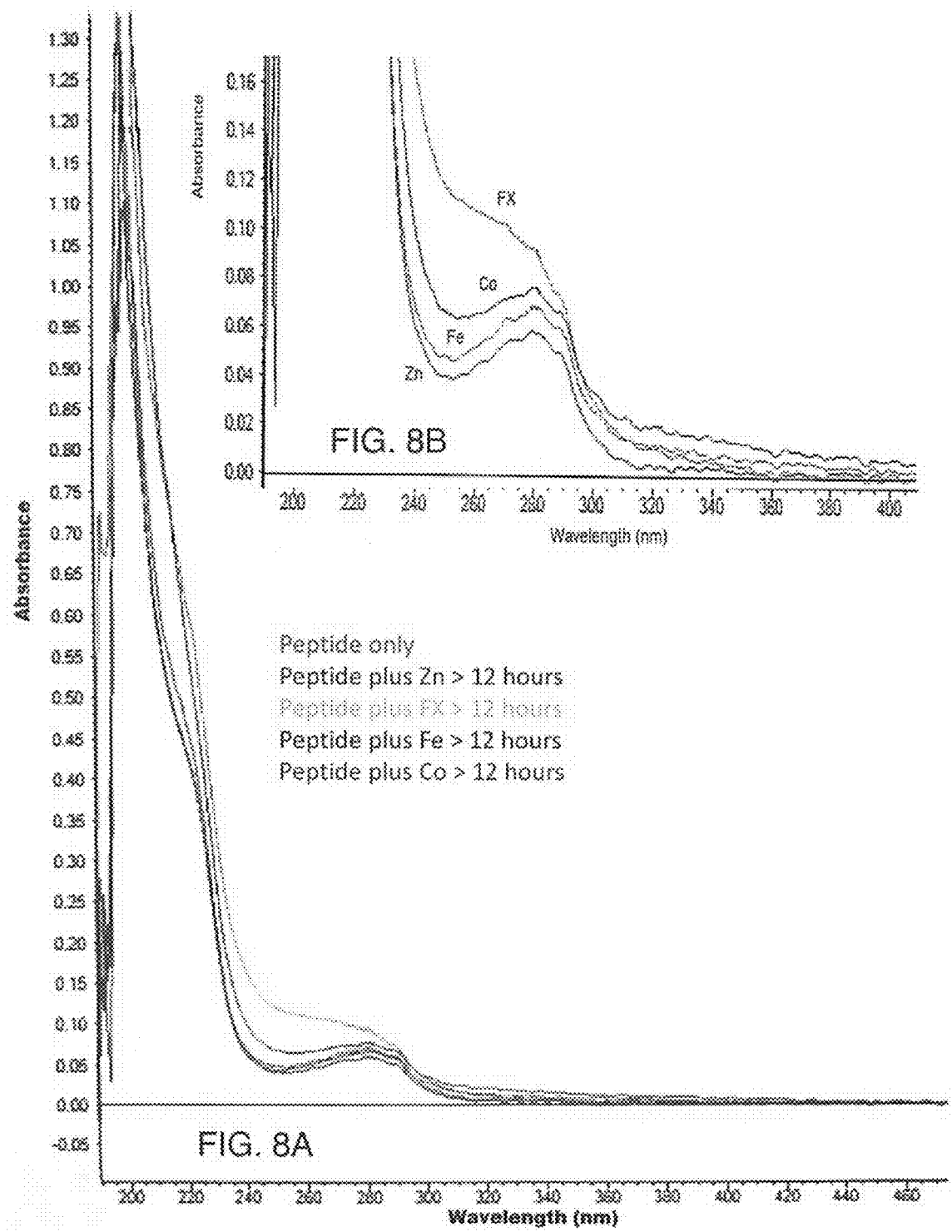

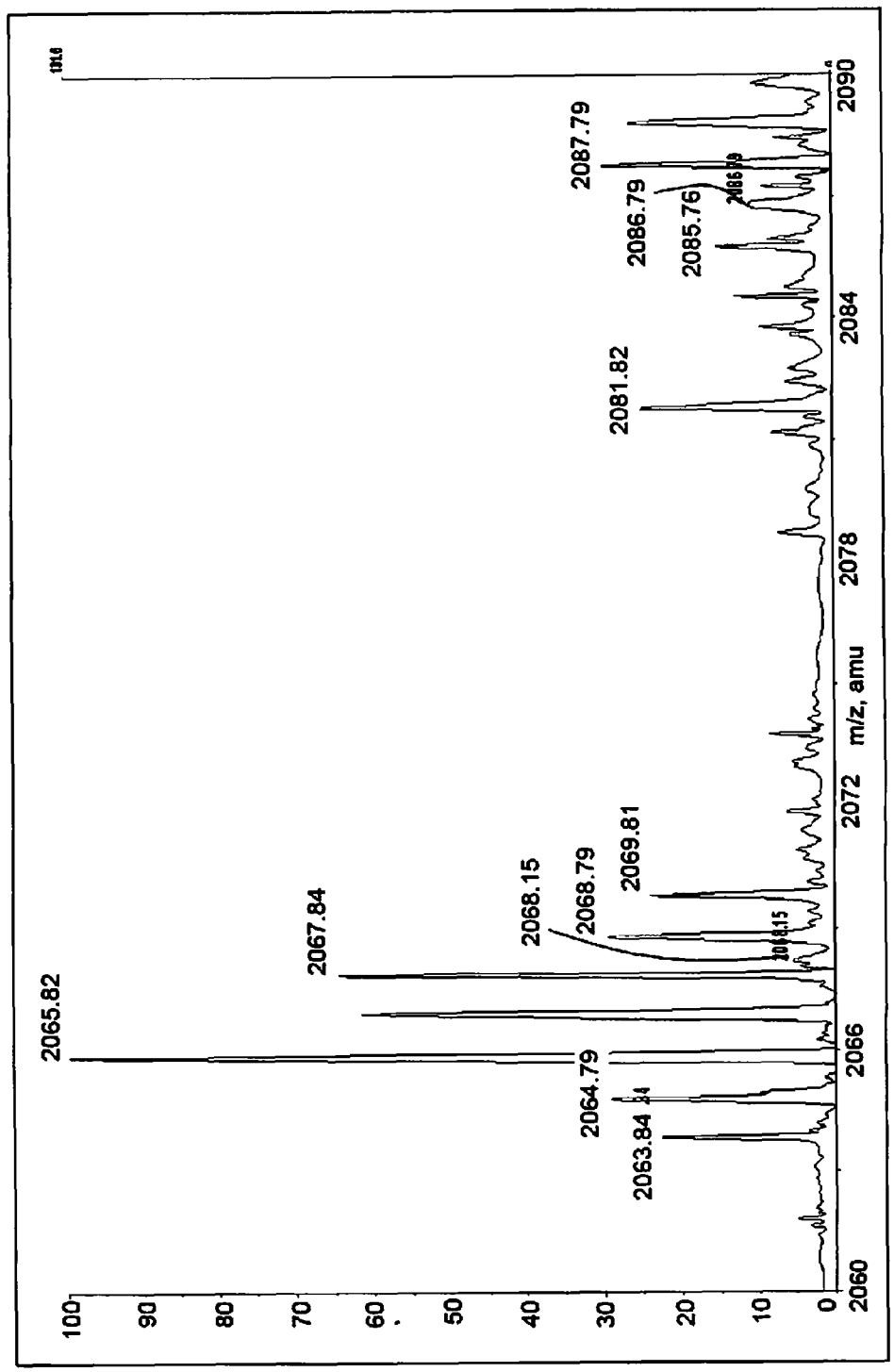
FIG. 9A: MALDI TOF spectrum of F2 Peptide diluted 1:100 zoomed in to the main peaks at 2063-2069 Da

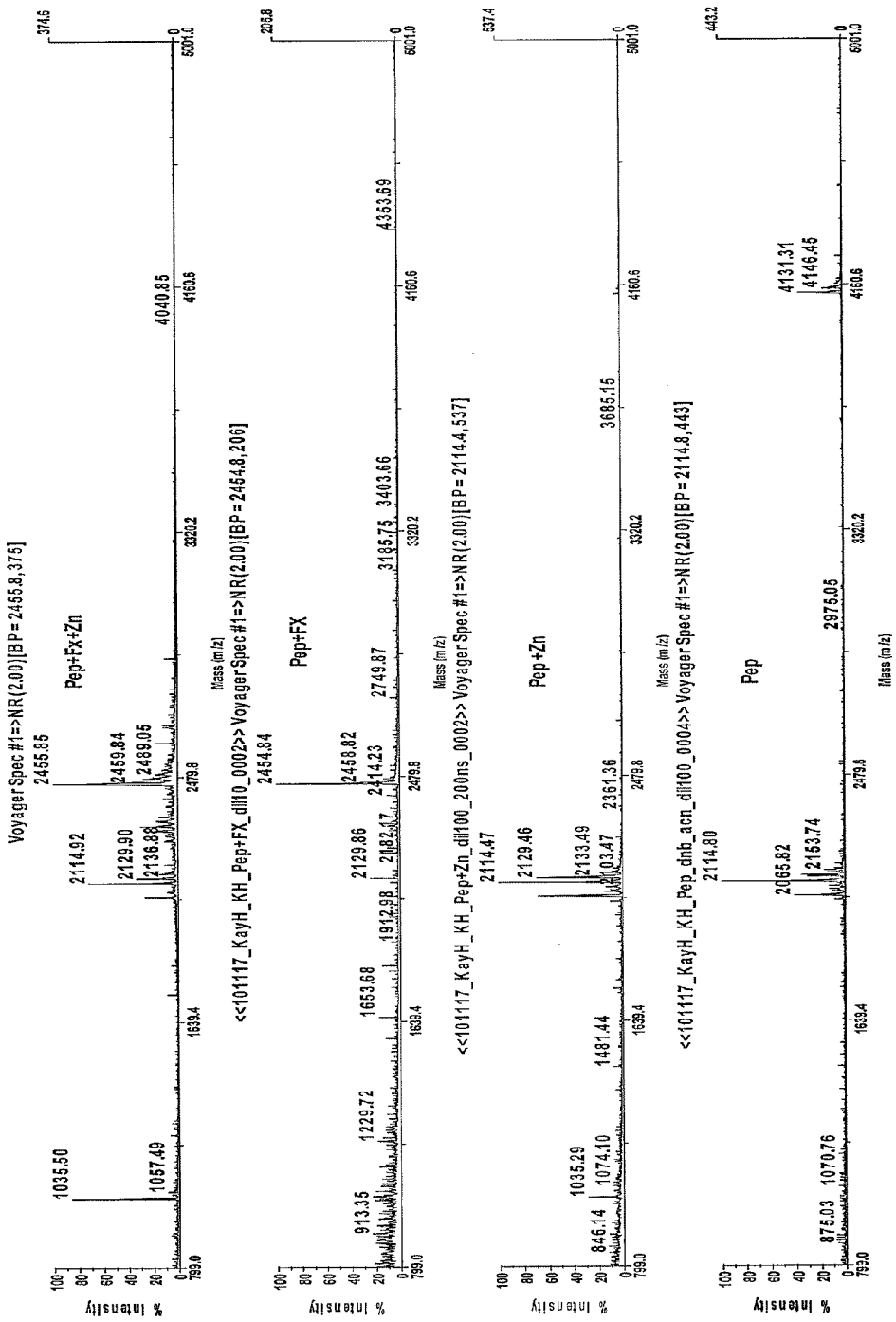
Fig 9B: MALDI-TOF spectra of samples (from top to bottom) Pep+Fx+Zn, Pep+FX, Pep+Zn and Pep within mass range 800-5000Da

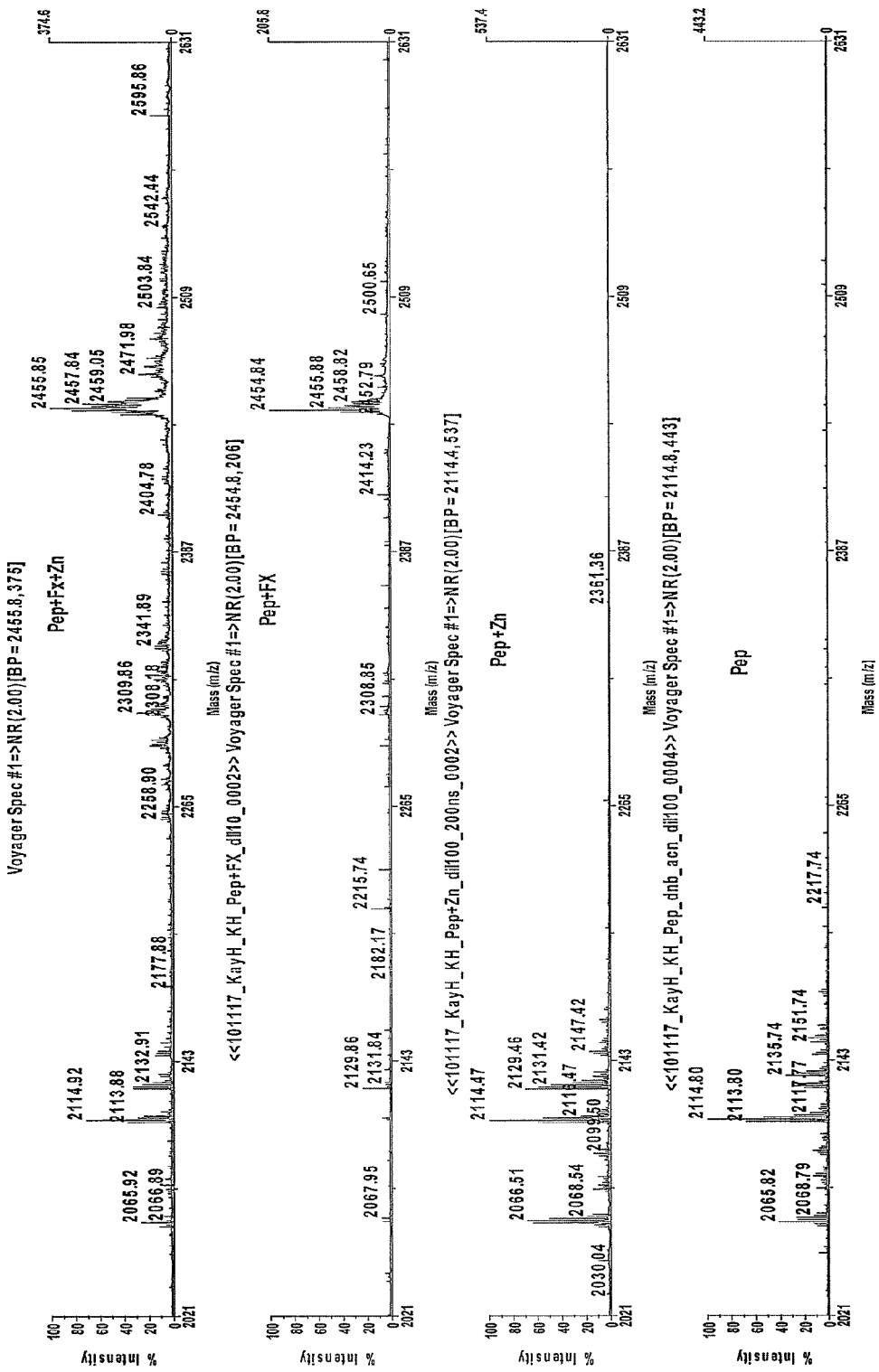
FIG 9C: MALDI-TOF spectra of samples (from top to bottom) Pep+Fx+Zn, Pep+FX, Pep+Zn and Pep, zoomed into mass range 2021-2621Da

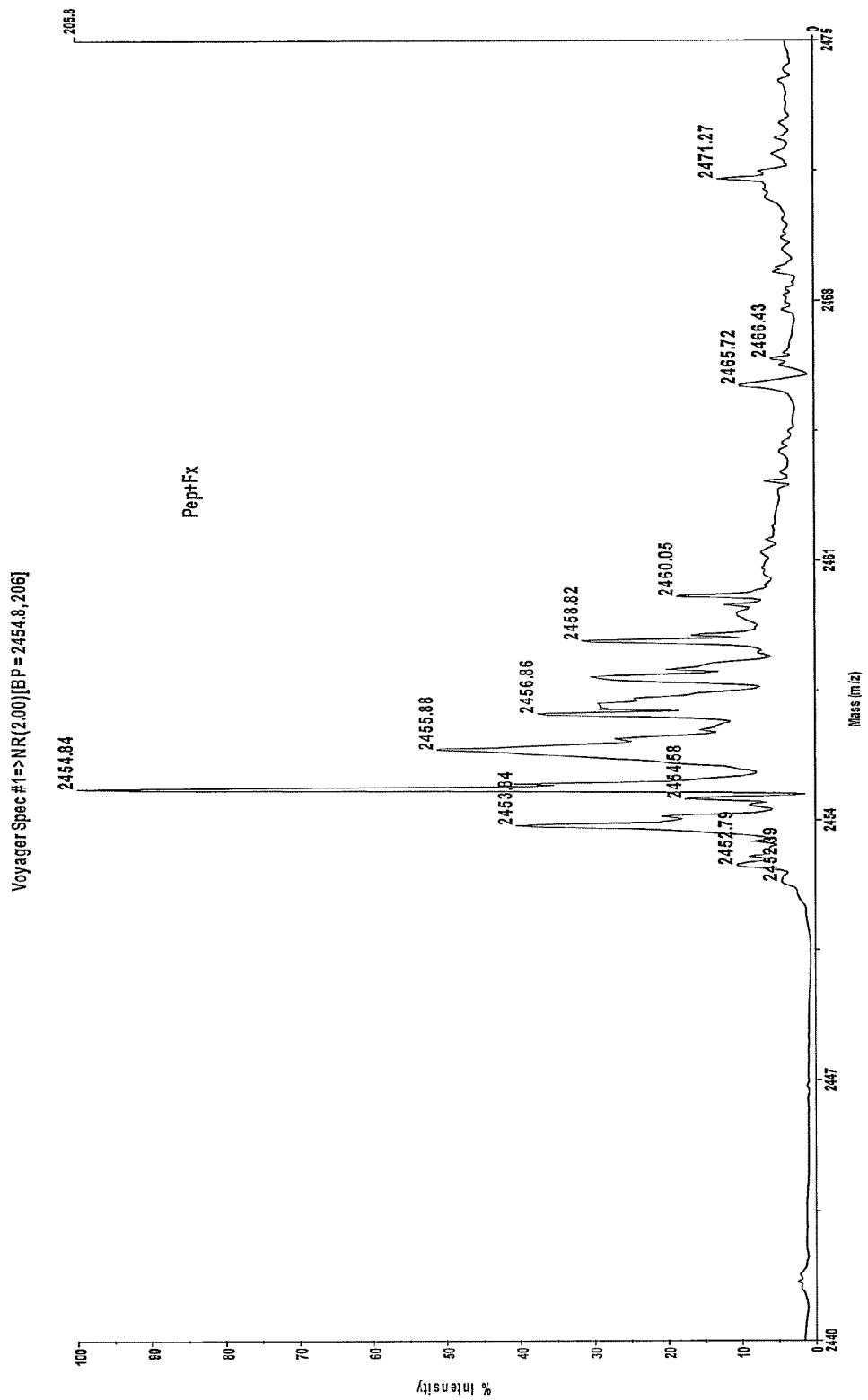
FIG 9D: MALDI-TOF spectrum of Pep+FX zoomed into the most intense set of peaks between 2440-2475 Da

PLATINUM (IV) COMPOUNDS TARGETING ZINC FINGER DOMAINS

CROSS-REFERENCE TO RELATED APPLICATION

This application claims priority to provisional application Ser. No. 61/336,360, filed on Jan. 21, 2010, and is a continuation-in-part of application Ser. No. 12/122,855, which was filed on May 19, 2008 and issued as U.S. Pat. No. 8,026,382 on Sep. 27, 2011, which claims priority to provisional application Ser. No. 60/938,781 filed May 18, 2007.

BACKGROUND OF THE INVENTION

In vitro, ex vivo and in vivo experimental results speak to the effective use of certain Pt(IV) compounds in the treatment of viral infections and their associated pathologies. Use of these compounds may also provide for recovery of immunological suppression by viruses, and be useful for the development of vaccines. This application is relevant to retroviruses, oncoretroviruses, filoviruses, arenaviruses and other viruses expressing nucleocapsid proteins or zinc-binding proteins where a Pt(IV) compound interacts with zinc-binding domains or zinc-binding sites, altering activities of the corresponding proteins. Other applications include interactions with the CCCH-zinc finger protein family, MCPIP-1, -2, -3, and -4, relevant to macrophage inflammatory responses (Liang et al., 2008) and adipogenesis (Younce et al., 2009). Pt(IV) compounds are proposed to also be relevant to the specific inhibition of other proteins containing cysteine-rich regions that could coordinate metals. The HIV-1 Trans-Activator of Transcription (Tat) protein, for instance, contains such a region (Huang and Wang, 1996; Frankel et al., 1988).

HIV-1 and other lentiviruses deliver two copies of single-stranded RNA into host cells where these are reverse-transcribed to DNA (deoxyribonucleic acid), incorporated into host DNA ("proviral DNA"), transcribed to make viral proteins, proviral circular (c)DNA and viral RNA (ribonucleic acid), then transported and packaged into virions. Gag protein is transcribed as a single structural polyprotein, and then sequentially cleaved to generate its components. A ribosomal frameshift may generate another viral protein, Gag-Pol, providing the viral enzymes: protease, reverse transcriptase and integrase. For HIV-1, protease cleaves Gag into three final nucleocapsid proteins (NCp): NCp15, NCp9 and NCp7.

Current interest in Gag owes partly to its ability to independently form virus-like particles (VLPs) in mammalian cells; in vitro, this occurs in the presence of nucleic acids and a cofactor (Campbell and Rein, 1999; Campbell, 2001). Immature VLPs do not include a surrounding outer membrane, yet emphasize the thermodynamic role of Gag proteins associated with RNA. Presence of nucleic acids is critical for Gag VLP production although Gag demonstrates preferential selectivity for viral RNA over other available oligonucleotides (Berkowitz, 1996).

The Gag-RNA interaction is proposed to rely upon unique zinc finger domains found in the NCp7 product of Gag. While zinc finger domains are frequent to the human genome—4500 CCHH zinc finger domains in 564 proteins—the CCHC zinc finger domain specific to all known nucleocapsid proteins of retroviruses is found in only 17 zinc domains of 9 human proteins. HIV-1 nucleocapsid protein 7 (NCp7) contains two such domains. Furthermore, these zinc finger domains of Cys-XX-Cys-XXXX-His-XXXX-Cys (or CCHC, where C/Cys is cysteine; H/His is histidine; and X is a variable residue) include 15 basic residues and two aromatic residues (phenylalanine and tryptophan)—each strategically located adjacent to the N-terminus Cys in each loop (see sequences below). These aromatic residues have special significance in their association with unpaired nucleotides through pi stacking; tryptophan (W37) associates between adjacent cytosine and guanine nucleotides, stacking with guanine (Morellet, 1998). Zinc ions ($Zn^{2+}$) coordinate to each of the 3 Cys (through the sulfur atoms) and one His residue (through the nitrogen atoms) in each loop. Cys49 and its sulfur have experimentally been found to be the most reactive sites (Maynard and Covell, 2001) and are expected to be the first event of zinc destabilization from the loop. NCp7 zinc-binding domains participate in essential viral conformational RNA strand changes known as "chaperoning"—both prior to virion packaging (strand aggregation) and prior to reverse transcription (helix destablilzation). Omission of either NCp7 zinc domain results in unexpected premature viral DNA synthesis in virus producer cells and the production of noninfectious particles with a high level of viral DNA, as opposed to RNA (Houzet, 2008). Synchronization of cellular translational events is also regulated through NCp7, making the nucleocapsid protein a promising target for therapeutic treatments (Didierlaurent, 2008).

Primary sequences of NCp7 highlighting residue properties and zinc coordination sites:

```
SEQ ID NO 2:
IQKGNFRNQRKTVKCFNCGKEGHIAKNCRAPRKKGCWKCGKEGHQMKDCT

ERQANFLGKIWPSHKGRPGNF (Cruceanu, 2006)

SEQ ID NO 3:
MQRGNFRNQRKNVKCFNCGKEGHTARNCRAPRKKGCWKCGKEGHQMKDCT

ERQANFLGKIWPSYKGRPGNFL (Anzellotti, 2006)
```

Multiple and cell-specific activities act through NCp7, emphasizing the efficient redundancy notorious to viruses. Besides serving as structural housing components of genomic viral RNA (the nucleocapsid), NCp7 proteins are required for genomic RNA packaging and chaperoning; transfer RNA annealing; integrase-mediated strand-transfer; virus assembly and budding; Gag trafficking and processing; and temporal control of reverse transcription (Didierlaurent, 2008; Houzet, 2008; Thomas and Gorelick, 2008; Mascarenhas and Musier-Forsyth, 2009). While other peptides and proteins may substitute for these activities—resulting in cell-specific effects—optimized efficiencies by NCp7 may be critical to successful virus infection and production. Additionally, zinc finger domains of NCp7 are integral to the full length Gag protein prior to each of three sets of protease cleavages resulting in the final products: matrix (NCp15), capsid (NCp9), nucleocapsid (NCp7) and p6. Therefore, zinc-finger domain alterations by coordinating to platinum(IV) compounds may range across effects of full length Gag precursor protein to the fully cleaved mature nucleocapsid protein.

Alterations to the zinc-finger domain configuration result in profound changes to its protein function. Site-directed mutagenesis of HIV-1 NCp7, substituting leucine for proline-31 in the peptide linker between its two zinc-binding domains, resulted in the formation of non-infectious and immature viral particles (Morellet, 1994). Even subtle residue substitutions (interchanging cysteines and histidines) in the zinc-binding domain altered the cooperativity of DNA helix-coil transitions such that the protein lost its nucleic acid-chaperoning capacity (Guo, 2002; Williams, 2002;

Ramboarina, 2004); a mutant form of nucleocapsid with both CCHC domains changed to SSHS is unable to bind zinc and is impaired to facilitate minus-strand transfer in reverse transcription (Guo, 2000). Other mutations to this domain result in premature reverse transcription and unusual incorporation of viral DNA into virion progeny (Thomas, 2008). Mutations in the N-terminal domain of the nucleocapsid protein result in a strong reductions of proviral DNA in host cells (Berthoux, 1997; Tanchou, 1998). Numerous other investigators report that mutations to the NC protein, as part of Gag and/or as mature NCp7, result in production of viral particles defective in replication (Dannull, 1994; Ottmann, 1995; Poon, 1996; Schmalzbauer, 1996) and/or defective in genomic RNA packaging (Aldovini and Young, 1990; Gorelick, 1990; Dorfman, 1993; Mizuno, 1996).

Manrique et al. (2004) addressed the role of the feline immunodeficiency virus (FIV) nucleocapsid (NC) protein in late stage virus replication. Defective phenotypes with respect to particle formation and RNA binding were observed when the first cysteine residue in the NC proximal zinc finger, or when basic residues connecting both zinc fingers, were replaced. HIV-1, SIV and FIV each share the highly conserved $CX_2CX_4HX_4C$ sequence of NC zinc finger domains (Table 1; Thomas and Gorelick, 2008). The function of FIV Gag proteins parallel those of HIV-1 Gag, as reviewed by Luttge and Freed (2010), including short peptide motifs essential for proper release of assembled virions from infected cells, RNA chaperoning, trafficking to membranes and virus assembly. Similarities in structure and functions of Gag/nucleocapsid zinc finger domains, together with in vitro HIV-1 data illustrating associated defective particle phenotypes and reductions in virion production support the success of human translational efficacies.

TABLE 1

Comparative Sequences of Nucleocapsid Zinc Domains

| Virus | Protein | Size | N-Terminal Zinc finger | C-Terminal Zinc finger | Basic Residues | Acid Residues |
|---|---|---|---|---|---|---|
| HIV-1 | p7 | 55 | SEQ ID NO 4: CFNCGKEGHIAKNC | SEQ ID NO 7: CWKCGKEGHQMKDC | 15 (27%) | 4 (7.3%) |
| SIV | p8 | 52 | SEQ ID NO 5: CWNCGKEGHSARWC | SEQ ID NO 8: CWKCGQMGHVMAKC | 12 (23%) | 1 (1.9%) |
| FIV | p10 | 66 | SEQ ID NO 6: CFNCKKPGHLARQC | SEQ ID NO 9: CNKCGKPGHVAAKC | 14 (21%) | 1 (1.5%) |

HIV-1 sequence data from GenBank accession number AF324493 (Ottmann, 1995).
SIV sequence data from GenBank accession number AY817672 (Gorelick, 1999).
FIV sequence data from GenBank accession number M25381 (Manrique, 2004).

In a pilot study of two FIV-infected felines, a short increase in peripheral blood mononuclear cell proviral load was observed in both animals immediately following (14 days later) the final dosing of the platinum(IV) compound, FX101. Proviral loads declined over subsequent months, even below pretreatment baseline measures, together with undetectable plasma viremia. The initial spike in proviral load following drug clearance may reflect a temporary yet insufficient recovery of NCp7 in its role as helix destabilizer, preceding incorporation into host DNA. Other studies (in vitro p24, in vivo plasma viremia and in vitro reduced virion production) may reflect inhibition of NCp7 in its role as strand aggregator preceding viral assembly. Ultimately, a long term in vivo reduction of both proviral DNA burden and plasma viremia support a virus-debilitating target with corresponding host relief from daily dosing.

TABLE 2

Alignment of Group M HIV-1 Nucleocapsid Protein Sequences.

| | N-terminal Zinc Finger | C-terminal Zinc Finger |
|---|---|---|
| M-Group Consensus | SEQ ID NO 10: CFNCGKEGHIARNC | SEQ ID NO: 14 CWKCGKEGHQMKDC |
| A1 | SEQ ID NO 11: ---------L---- | SEQ ID NO: 14 -------------- |
| A2 | SEQ ID NO 11: ---------L---- | SEQ ID NO: 14 -------------- |
| B | SEQ ID NO 12: -----------K-- | SEQ ID NO: 14 -------------- |
| C | SEQ ID NO: 10 -------------- | SEQ ID NO: 14 -------------- |
| D | SEQ ID NO: 12 -----------K-- | SEQ ID NO: 14 -------------- |
| F1 | SEQ ID NO: 12 -----------K-- | SEQ ID NO: 15 -----R-------- |
| G | SEQ ID NO: 11 ---------L---- | SEQ ID NO: 14 -------------- |
| H | SEQ ID NO: 10 -------------- | SEQ ID NO: 15 -----R-------- |
| K | SEQ ID NO: 10 -------------- | SEQ ID NO: 14 -------------- |
| 01-AE | SEQ ID NO: 11 ---------L---- | SEQ ID NO: 14 -------------- |
| 02-AG | SEQ ID NO: 11 ---------L---- | SEQ ID NO: 14 -------------- |
| 03-AB | SEQ ID NO: 13 ------D--L---- | SEQ ID NO: 14 -------------- |
| 04-CPX | SEQ ID NO: 11 ---------L---- | SEQ ID NO: 14 -------------- |
| 06-CPX | SEQ ID NO: 11 ---------L---- | SEQ ID NO: 14 -------------- |
| 07-BC | SEQ ID NO: 10 -------------- | SEQ ID NO: 14 -------------- |
| 08-BC | SEQ ID NO: 12 -----------K-- | SEQ ID NO: 14 -------------- |
| 10-CD | SEQ ID NO: 12 -----------K-- | SEQ ID NO: 15 -----R-------- |
| 11-CPX | SEQ ID NO: 11 ---------L---- | SEQ ID NO: 14 -------------- |
| 12-BF | SEQ ID NO: 12 -----------K-- | SEQ ID NO: 15 -----R-------- |
| 14-BG | SEQ ID NO: 11 ---------L---- | SEQ ID NO: 14 -------------- |
| NL4-3 | SEQ ID NO: 12 -----------K-- | SEQ ID NO: 15 -------------- |

Applications across most lentivirus strains and subtypes are anticipated since the zinc binding domain is highly conserved. Consensus M-Group HIV-1 Subtypes, for example, are summarized in Table 2 from Thomas and Gorelick (2008), using the Los Alamos HIV Sequence Database. Since the NC zinc finger is conserved across HIV-1, HIV-2, SIV (Morellet, 2006) and FIV (Manrique, 2004), activities across these mutants are anticipated.

Positively-charged NCp7 is well-suited to accommodate the negatively-charged phosphate groups of polynucleotides, positioning base complements within range to form energetically-stabilizing hydrogen bonds. These effects would be especially favorable in the context of a lipid membrane (hydrophobic), and could possibly include diffusional forces generated by changing solubility dynamics as folding transpires. It has been suggested that the rapid conformational changes of NCp7 required to facilitate observed interactions with both ssDNA and dsDNA (single stranded and double stranded; analogous to RNA) could involve alternating pi-stacking interactions of key aromatic residues with DNA nucleotides (Cruceanu, 2006). Aromatic residues reduce the HOMO-LUMO (highest occupied molecular orbital—lowest unoccupied molecular orbital) energy gap in pi-stacking groups, enhancing these associations (Ishida, 1990). Hence, these aromatic residues could essentially act as switches. Any alterations to their properties would have profound effects on Gag-RNA interactions. Interestingly, the precursor to NCp7, NCp9, contains a length of hydrophobic residues and demonstrates significantly slower DNA interactions (Khan and Giedroc, 1994). Noncovalent pi stacking interactions between proline and tryptophan residues (~7 kcal/mol, comparable to hydrogen bonding) have recently been measured, despite proline's lack of aromaticity (Biedermannova, 2008), adding another possible residue contributing to such interactions.

Zinc is critical to the functionality of nucleocapsid proteins; platinum, however, can coordinate in these metal-binding peptides. Transplatin has been shown to displace zinc (Burdette, 2006), owing to the geometry of cysteine residue coordination sites, with displacement of Pt(II)-coordinated chloride ions being an early step (Ivanov, 1998). Two Pt(II) equivalents may be required to fully eject zinc, although there are several observations where metal coordination sharing a single chloride occurs (—Pt—Cl—Zn—); importantly, these studies have been limited to Pt(II) structures. Using an aromatic ligand to direct trans-Pt(II) complexes toward the tryptophan (W37) of NCp7 zinc fingers, trans-[Pt(II)Cl(bispyridine)(9-ethylguanine)] eventually displaces zinc, transitioning through a Pt—S—Zn bridging complex with the loss of chloride ions (Anzellotti, 2006). Gold and palladium have each also demonstrated the capacity to form sulfide-bridging interactions with zinc-like domains (de Paula, 2009), suggesting that alternative modes may contribute additional interactions with the zinc finger domain. Previous small molecule approaches to zinc finger domain interruptions include electrophilic attack by nitrosylated organic aromatics, disulfides, disulfoxides, etc., although these are both nonspecific (toxic) and unstable (Rice, 1997). The nature of specific metal uptake by cells may provide improved specificity for this approach, concentrating metal species within membrane compartments shared by viruses during both infection and assembly.

Current antiviral therapeutics require daily dosing with associated toxicities and development of drug-resistance. Our studies suggest a relief from daily dosing capable of maintaining low viral loads, both in viremia and proviral load, over successive months. It is proposed that viral progeny incorporate the small molecule into their nucleocapsid proteins, thus impairing successful replication in subsequent host cells. Further, alterations to zinc fingers of nucleocapsid proteins have been shown to result in vast differences in viral RNA/DNA splicing and packaging, impacting subsequent infection viral production pathways (Houzet, 2006). Inhibitory effects would then be compounded with first cycle effects, amplifying activities. Mass spectrometric analysis confirms that select Pt(IV) compounds target CCHC nucleocapsid zinc domains of lentiviral Gag proteins, thus accounting for altered activities known to require zinc in the active site. Effects include inhibition of processes such as mature virion formation, of proviral DNA incorporation and of Gag polyprotein processing.

Both selenite ($SeO_3$) and ebselen (2-phenyl-1,2-benzisoselenazol-3[2H]-one) interfere with zinc finger-containing DNA binding domains (Larabee, 2002), albeit via distinct interactions. While both of these selenium compounds successfully ejected the zinc atom from the transcription factor Sp1 DNA-binding domain, ebelsen induced the formation of a disulfide bond (oxidation) in the vacated protein while selenite also produced a sulfur-coordinated selenium species with the two available cysteines (Larabee, 2009). Thus, different modes of action were ultimately effective in achieving inhibition of DNA binding through alteration of the zinc finger by selenium.

Other metals shown to compete or coordinate with zinc finger domains include arsenite (Ding, 2009); cobalt(III) (Harney, 2009); platinum(II), palladium(II) and gold (III) (de Paula, 2009); cadmium(II) and mercury(II) (Heinz, 2009).

Other Factors

Trans, cis-$[Pt(en)(OH)_2Cl_2]$ and trans, cis-$[Pt(en)(OH)_2I_2]$ exhibited different reactions to albumin proteins. The difference is due to iodo attack of the cysteine residue, resulting in a sulfenic acid derivative. Low molecular weight thiols react with Pt(IV)-Iodo bonds of trans, cis-$[Pt(en)(OH)_2I_2]$ forming chelate-ring-opened Pt(II)(en) species. (Kratochwil and Bednarski, 1999). Given the high proportion of thiols in zinc fingers, these types of interactions may be significant. It also suggests that Pt(IV)iodo compounds may prove unexpectedly effective.

Pt(IV) compounds have been reported to have biological actions distinct from their Pt(II) counterparts, even when they show cross-resistance (Hamberger, 2009). The octahedral geometries of Pt(IV) complexes are unusually substitution and kinetically inert; this stability can be explained by its filled $5d_{t2}$ low spin configuration coordinated with weak field ligands resistant to oxidation. Pt(IV) may require reduction to the Pt(II) species to become cytotoxic (Bednarski, 2007; Mellor, 2005; Galanski, 2003); several Pt(IV) compounds have been reported stable against biological reductants such as glutathione (Kratochwil and Bednarski, 1999). DNA alkylation by cisplatin is proposed to transition through the exchange of a chloride with an aquo ligand, leading to a positively-charged Pt(II) intermediate that approaches negatively-enveloped DNA. In contrast, nucleocapsid proteins are highly basic. A positively charged Pt species analogous to those alkylating DNA would be electronically hindered from interaction with a basic protein such as NCp7; being substitution inert may be a critical feature of the Pt(IV) capacity to interact with the zinc coordination site.

The absence of myelosuppression from our in vivo studies using Pt(IV) compounds may reflect cytotoxicities limited to specific transformed cell lines rather than to primary cells. Other Pt(IV) compounds have been reported to exhibit direct cytotoxicities in rat and human astrocyte cell lines, without affecting the viability of rat primary astrocytes, nor their functions (Markovic, 2005); in contrast, cisplatin was toxic to both primary cells and transformed cell lines in these studies. While cisplatin can be used to treat certain tumors in the dog, it cannot be utilized in the cat because of fulminant pulmonary oedema that occurs at standard doses (Barabas, 2008); yet, we have successfully administered repeated doses of a Pt(IV) compound to cats without complications. Clinical chemistry panels, complete blood counts and urinalysis from FIV studies in cats evidence no indications of adverse reactions to this therapeutic when administered twice weekly over 4 weeks at the proposed therapeutic dose (6-8 mg/dose intravenous).

While alkylation of peripheral blood leukocyte DNA occurs with cisplatin and its analogs, neither impairment of leukocyte function nor myelosuppression have been observed in our studies. Other reports of Pt(IV) compounds, such as those produced by hydrogen peroxide oxidation, are inactive as antitumor agents and have been shown incapable of unwinding PM2-DNA (Peritz, 1990). Experiments distinguish between Pt(IV) and Pt(II) compounds, both of which exhibit cytotoxicity in ovarian cell lines (A2780, A2780/C30, and CHO), yet only the Pt(II) compounds show evidence of covalent binding to single- or double-stranded DNA by highly sensitive nuclear magnetic resonance (NMR) detection studies (Bose, 2008). Further, some Pt(IV) compounds do not accumulate as cisplatin analogs do (New, 2009). These observations and measures "represent a clear paradigm shift not only in expanding the molecular targets for Pt . . . but also in strategic development . . . " (Bose, 2008). Some Pt(IV) compounds resistant to reduction have failed to react with DNA in the presence of either low (0.015 mM) or high (3.0 mM) concentrations of glutathione (Kratochwil and Bednarski, 1999), hence interactions exclusive of DNA interactions are evidenced for platinum compounds of the higher oxidation state (i.e., +4). The metallo-biochemistry of certain platinum(IV) compounds focuses on cellular and molecular events beyond DNA binding (Bose, 2002).

Standard in vitro HIV antiretroviral testing has focused upon viral targets such as inhibitors of transcription, infection, viral protease and integrase. The targets for certain platinum(IV) compounds, however, are the zinc finger domains of nucleocapsid proteins, whose activities may not be accurately reflected by these test methods. For instance, deletion of both zinc fingers causes activation of reverse transcription in virus producer cells (Didierlaurent, 2008), which would appear to be counteractive as an antiviral if viewed as an inhibitor of transcription. Furthermore, depending on the specific mutation of the zinc finger motif, increases (rather than decreases) of infectivity have been reported (Mark-Danieli, 2005), although these mutations coincided with genomic encapsidation of larger amounts of foreign RNA in the production of "normal" virion-like particles. Changes to viral transcription, protease and integrase activities may be indirect consequences of the primary mechanism of action—alterations in viral RNA/DNA "chaperoning", Gag processing and virion assembly due to alterations of the zinc domain.

Most available HIV therapeutics belong to classes of nucleoside/nucleotide reverse transcriptase inhibitors (NRTIs), non-NRTI's or protease Inhibitors (PIs). While no maturation inhibitors have yet achieved FDA approval, this new class of therapeutics includes both Bevirimat (PA-457 or MPC-4326; CS Adamson, 2009) and Vivecon (MPC-9055), both by Myriad Pharmaceuticals and in clinical trials. Azodicarbonamide (ADA) had also proceeded into clinical trials. The utility of maturation-inhibiting antiretrovirals recognizes the fundamental roles of highly conserved Gag viral domains, applicable across multiple strains.

With respect to Pt(IV) compounds of octahedral geometries, it seems interesting that trans-halide geometries have demonstrated antiviral activities while corresponding cis-halide geometries have been ineffective. Pt(IV)s of octahedral geometries form many thermally stable and kinetically inert complexes (Cotton and Wilkinson, 1972, p. 1040), reducing toxic side effects associated with Pt(II)'s. It may have been fortunate to have first examined virus inhibition using feline T-cells, since localization of Gag proteins differs between T-cells and macrophages—the former localize to plasma membranes while the latter distribute to multivesicular bodies (Joshi, 2009). Gag protein associations with cholesterol have been identified for macrophages in multivesicular bodies (Lindwasser and Resh, 2004); cholesterol is well known to traffic with caveolin proteins, so this could offer alternative interactions since Pt(IV)s appear to partition to caveolar fractions as well as to lipid rafts.

A number of gamma-retroviruses have been identified to contain the classical caveolin-1 binding domain (CBD) motif rich in aromatic residues and exhibiting the characteristic spacing $\phi xxxx\phi xx\phi$ or $\phi x\phi xxxx\phi$; $\phi$=W, F, Y (Yu, 2006). Other interactions between viruses and caveolin-1 proteins may occur through nonclassical motifs, and have been observed to involve the cytoplasmic tail of caveolin-1. Since precipitation of caveolar proteins from sucrose-gradient extractions included a high proportion of Pt(IV) distribution to that fraction, direct associations between the protein and Pt are implied. Whether these associations contribute to nucleocapsid protein inhibitions is yet to be explored. Nevertheless, Pt specifically distributed to the most buoyant lipid raft fraction as well, creating additional modes of exposure to sites of viral assembly. Targeting to lipid rafts may prove advantageous to certain antiviral applications.

Matrix Metalloproteinases

It is noteworthy that we observed marked reductions in both MMP-2 and MMP-9 gelatinases throughout our studies. Matrix metalloproteins (MMP's) are characterized by zinc-binding domains also, although their chelating residues differ from those of lentiviral nucleocapsid proteins. The interaction of Pt(IV) compounds with these zinc domains offers therapeutic value; inhibition of the zinc domain of MMP-3 has been reported for certain Pt(II) compounds comprising 3 labile ligands (Arnesano, 2009).

MMPs are a large family (26 at present) of zinc-dependent proteases with multiple roles in extracellular matrix remodeling (Amalinei, 2007), signaling pathway regulations, cell morphology, immune (Elkington, 2009) and inflammatory responses (Manicone and McGuire, 2008) and in the release of soluble factors (Van Lint and Libert, 2007). Most MMPs are secreted in a latent (pro-MMP) form and activated either by proteolytic or oxidative disruption of a conserved cysteine switch (PRCGVPDLGR). Tissue inhibitors of metalloproteinases (TIMPs) physiologically regulate MMPs. Interestingly, this regulation involves interactions between cysteines on TIMPs and zinc metal (Zucker, 1998), otherwise coordinated to histidines and gluatamic acid residues within the MMP catalytic site. Involvement of MMPs in neurodegenerative diseases, oncological disorders, autoimmune and cardiovascular and other diseases identifies them as therapeutic targets.

Data from in vivo studies of mice and cats demonstrate significant reductions in plasma MMPs with administration of certain Pt(IV) compounds. Both MMP-2 and MMP-9 levels were reduced, although no corresponding changes to measured TIMPs accounted for these reductions. MMP's are reported to be particularly involved in the pathogenesis of HIV infections (Webster and Crowe, 2006). These data suggest an interaction between the catalytic zinc binding site and platinum complexes that may contribute inhibitory effects observed for virus production and infiltration. Importantly, platinum coordination to cysteine residues on TIMPs might affect TIMP regulation of MMPs. The MMP's coordinate Zn mainly through N (of His) or O (of Glu or Asp) atoms (Tallant, 2009), different from the mostly S(Cys)-chelated Zn in Gag proteins.

The core domain of MT1-MMP (aka MMP-14, membrane bound) contains four highly occupied metal sites binding two zinc and two calcium ions in a similar manner to the classical MMPs, but lacking a third calcium binding site. The catalytic zinc is chelated by nitrogens on 3 histidines and one cysteine. The second 'structural zinc', ZN002, is similarly coordinated to nitrogens of 3 histidines and one carboxylate oxygen of aspartate. MT1-MMP is found in cholesterol-rich lipid rafts on the plasma membrane. Upregulation of caveolin-1 has also been related to the inhibition of MT1-MMP through its surface regulation (Kim and Chung, 2008).

Hepatitus C and Other Viruses

The nonstructural protein 5A (NS5A) of HCV is essential to viral RNA replication and appears to modulate the host cell environment (Marcotrigiano and Tellinghuisen, 2009). NS5A is a large hydrophilic phosphoprotein with three domains; the amino-terminal domain notably coordinates a single zinc atom to 4 cysteines (Cys39, Cys57, Cys59 and Cys80) and is required for virus replication, interferon resistance and apoptosis (Liang, 2007). NS5A is an active component of HCV replicase, a key regulator of replication and a modulator of cellular processes ranging from innate immunity to dysregulated cell growth; the amphipathic-helix at its amino terminus contains anchors to the host cell membrane (Moradpour, 2005). Mutations of NS5A disrupting either the membrane anchor or zinc binding of NS5A are lethal for RNA replication (Moradpour, 2005). Conserved among the Hepacivirus and Pestivirus genera, the zinc-coordinating cysteines follow the pattern of $CX_{17}CXCX_{20}C$. Mutation of any of the four cysteine residues coordinating the NS5A zinc atom produces a lethal phenotype for HCV RNA replication, suggesting this motif is absolutely required for functionality (Tellinghuisen, 2004).

Another HCV nonstructural 3 (NS3) protein, a serine proteinase, is zinc-containing, whose distinct auto-proteolytic and protease activities are both zinc-dependent, with an absolute requirement for cysteine residues 1123, 1125 and 1171 within NS3 (Tedbury and Harris, 2007). Spectroscopic studies have shown that changes in the conformation of the zinc-binding site correlate with changes in the specific activity of the enzyme, such that the NS3 proteinase is inhibited by compounds capable of extracting zinc from its native coordination sphere (De Francesco, 1999). NS3 is also required for virus maturation (De Francesco, 1999). Pt(IV) compounds may interact with these key HCV viral proteins—NS5A and/or NS3—preventing viral activities or virus maturation, and providing therapeutic value.

Junin virus, a South American arenavirus, is the aetiological agent of Argentine haemorrhagic fever. A zinc-coordination site of the carboxy-terminal region of its N protein corresponds to the sequence $CX_2HX_{23}CX_4C$. Specificity for zinc binding was demonstrated by competition with other divalent metal ions (Tortorici, 2001). Inactivation of the arenavirus by antiretroviral zinc finger-reactive compounds resulted in particles which retained the immunoreactivity of their surface glycoproteins, providing a potential antigenic agent for the development of a vaccine (Garcia, 2009) or development of an immunological adaptive response. Production of inactive or dysfunctional virions in such a manner may extend to numerous vaccine applications; studies evaluating such potentials are in progress.

Examples of Viruses Containing Zinc-Binding Domains

Hantaviruses display a highly conserved CCHC-type classical zinc finger domain that participates in viral assembly and host-pathogen interactions (Estrada, 2009).

The nucleocapsid protein VP30 of Marburg and Ebola fiolviruses each contain a zinc-binding motif (Enterlein, 2006).

Human T-Cell Lymphotropic Virus Type 1 is a retrovirus containing two CCHC zinc finger domains in its nucleocapsid domain; infection can lead to adult T-cell leukemia or demyelinating diseases. As compared with HIV-1, HTLV-1 shares nucleic acid chaperoning and packaging activities, although exhibiting some differences in these overall efficiencies (Darugar, 2008)

Herpes Simplex Virus (HSV) replication requires binding of DNA with a zinc metalloprotein, characterized as a zinc finger Cys-$X_{2-5}$-$Cys_{2-15}$-Cys/His-$X_{2-4}$-Cys/His, with Cys=cysteine and X=a variable residue, each of subscripted numbers (Chinami, 1996). Zinc finger domains have been suggested as therapeutic targets for HSV (Beerheide, 1999; Scozzafava, 2002).

A recent review by AJ Kesel (2003) depicted the zinc finger domains (or motifs) in HIV-1. Similar motifs are reported in various viruses such as Picornaviridae (poliovirus, human coxsackievirus, hepatitis A virus), Flaviviridae (yellow fever virus, Dengue virus, West Nile virus, Kunjin virus, St. Louis encephalitis virus, hepatitis C virus), Togaviridae (rubella virus), Coronaviridae (human coronavirus, human SARS-associated coronavirus), Rhabdoviridae (rabies virus), Paramyxoviridae (human parainfluenza virus, measles virus, human respiratory syncytial virus), Filoviridae (Marburg virus, Ebola virus), Bornaviridae (Borna disease virus), Bunyaviridae (Hantaan virus), Arenaviridae (Lassa virus), Reoviridae (human rotavirus) and Retroviridae (HTLV-1, HIV-1, HIV-2).

Malaria

Trypanosomatids, the causative parasite of malaria, contains a single mitochondrion containing kinetoplast DNA—a unique extrachromosomal DNA network. Two short sequences of these DNA minicircles of this network are conserved in all trypanosomatid species. A protein containing five CCHC-type zinc finger domains, designated universal minicircle sequence-binding protein (UMSBP), mediates DNA-binding activity and protein oligomerization throughout the trypanosomatid cell cycle. Importantly, this activity has been shown to be redox-sensitive (oxidation state dependent). Reported to regulate UMSBP activity through a redox-based biological switch (Sela, 2008), platinum(IV) coordination to the zinc finger domain could impair trypanosomatids and be useful in the treatment of malaria.

Tat Proteins

Trans-activator of transcription proteins (Tat) are encoded by lentiviruses. Reported as early as 1988 (Frankel), Tat monomers form metal-linked dimers with metal ions through cysteine-rich regions, coordinating with either cadmium(II) or zinc(II). The cysteine-rich region of Tat proteins does not define a zinc-finger motif, per se, but five of the seven cysteine residues have been identified to coordinate two zinc(II) ions in a zinc-binding site (Huang and Wang, 1996). Coordination of zinc(II) ions appears to be critical to Tat transcriptional functions, as the Monoclonal Antibody MAb 5A4, which recognizes only the zinc-coordinated epitope, inhibited the trans-activation of the HIV long terminal repeat (LTR) in HeLa-CD4-LTR/beta-gal cells induced by treatment with the recombinant Tat protein (Misumi, 2004). Tat proteins interact with various cell receptors, including N-methyl-d-aspartate (NMDA) receptors. Its potentiating effects are associated with zinc(II) ions (Chandra et al., 2005). The sequence of a representative HIV-1 Tat protein below highlights cysteine residues of this region. Pt(IV) compounds are proposed to interact with the cysteine-rich region of Tat proteins, thus altering their activities.
Tat Protein, NCBI Accession Number AF224507.1:

```
SEQ ID NO 16:
mepvdprlep wkhpgsqpkt pctkcyckkcclhcqvcfmt kglgisygrk krrqrrrapq dnknhqvsls kqptsrargd ptgqeeskek veketvvdpv t
```

Tat proteins are produced by HIV-1 infected cells, and are sufficient to elicit detrimental pathological responses. Tat increases proliferation, sensitizes cells to apoptosis, and changes the conformation of Sp1, affecting its ability to bind to its cognate DNA sequence and to retain its zinc (Seve et al., 1999). Tat induces apoptosis of non-infected T lymphocytes, leading to a massive loss of immune competence (Egele et al., 2008). Importantly, holo-Tat (Tat protein coordinated to zinc (II) ions) appears to differ from apo-Tat (without zinc ions) in this activity (Egele, et al., 2008). The MAb 5A4 also inhibits apoptosis of Jurkat cells induced by treatment with the released native-Tat-protein-containing supernatant from the culture of HIV-1 (JRFL)-infected cells (Misumi et al., 2004).

Tat proteins have been shown to directly cause neurological damage or to activate microglial cells (King et al., 2006). They transport across the blood-brain-barrier and uniquely transport along neuronal pathways (Banks et al., 2005; Li et al., 2009). The integrity of the blood-brain-barrier itself is markedly affected by Tat proteins through the expression and distribution of specific tight junction proteins in brain endothelium (Andras et al., 2003), thus contributing to HIV trafficking into the central nervous system. Further relationships between Tat-caveolin signaling pathways (Zhong et al., 2008) and the localization of Pt(IV) compounds to caveolae may present targeting advantages for Pt(IV) in Tat regulation. Current HIV therapeutics do not affect Tat proteins after the lentivirus proviral DNA has integrated into host cells, such that Tat proteins continue to cause pathological damage independent of viral load.

Tat proteins have also been proposed to be useful in the development of vaccines (Campbell and Loret, 2009; Caputo et al., 2009). Their cell-penetrating capacities serve well as transporters, including cargoes of peptides, proteins, drugs, oligonucleotides, imaging agents, nanoparticles, micelles and liposomes (Wadia and Dowdy, 2005; Rapoport and Lorberboum-Galski, 2009). Whether the coordination of Tat proteins to metals such as Pt(IV) would render these transporters more useful—and less pathogenic—is likely. Since Pt(IV) would compete with biologically available metal cations for coordination, and prove to be more thermodynamically (or kinetically) stable, this could reduce detrimental effects of Tat proteins in their use as vectors and perhaps serve advantageously to stabilize protein conformations, even protecting from degradation. In this regard, coordination with zinc(II) cations deters Tat oxidation (Egele et al., 2008).

Tristetraprolin

Tristetraprolin (TTP), also known as TIS11, Nup475 or zinc finger protein 36 homolog (ZFP36), is a protein containing zinc binding domains of the CCCH type, each coordinating one zinc atom. The tandem zinc fingers consist of $CX_8CX_5CX_3H$ sequences (Genbank accession number X02611), where C is cysteine and X refers to variable amino acids with the subscript designating numbers of these. Alignments of these tandem zinc binding domains of all vertebrate members of the subclass are highly conserved, reflecting the importance of the domain. Tristetraprolin is important to macrophages as an intracellular regulator of tumor necrosis factor alpha (TNF-alpha) and granulocyte-macrophage colony-stimulating factor (GM-CSF) through message (m)RNA-stabilizing interactions. TTP knockout mice overproduce TNF-alpha. Mutation of a single cysteine residue to an arginine in either zinc finger completely abolished mRNA-destabilizing activities in TTP, suggesting that the zinc finger domain is critical to these activities (Lai, 2000). Coordination of TTP to platinum(IV) may be useful to alter regulation of both TNF-alpha and GM-CSF from immune cells. TTP has also been suggested as a therapeutic target for HPV-induced cervical cancer (Gallouzi and Di Marco, 2009).

Immunological Contributions

Viral proteins containing zinc-finger domains have been noted to inhibit antigen presentation pathways in host organisms. Members of both gamma-2 herpesviruses and poxviruses have been shown to downregulate major histocompatability complex (MHC) class I (Fruh, 2002). In addition, other cell surface molecules involved in immune recognition by thymus (T-)cells and Natural Killer cells are downregulated. Homologous K3 and K5 genes of Kaposi's sarcoma-associated virus inhibited antigen presentation and decreased cell surface expression of HLA class I antigens (Stevenson, 2000). The proposed downregulations may be associated with K3 and K5 genes encoding zinc-domain-containing proteins from viral open reading frames (ORFs), affecting ubiquitin ligases that regulate the intracellular transport of transmembrane proteins through ubiquitination (Fruh, 2002). The association of Pt(IV) compounds with zinc binding domains of these proteins may prevent such viral subversions of the immune system, hence facilitating antigen presentation of the adaptive immune response and Natural Killer cell activities of the innate immune response.

Virus-like particles (VLP) are an effective type of protein subunit vaccine that mimic viral structure in the absence of the viral RNA or DNA genome. The capsid proteins of enveloped viruses, in particular, have been widely used for this purpose. VLPs present antigens causing both B-cell and T-cell immune responses (Paliard, 2000; Murata, 2003). The VLP-approach has been successfully evaluated as vaccines and adjuvants (Sedlick, 1997; Sugrue, 1997; Tacket, 2003; Warfield, 2003; Pushko, 2005; Kang, 2009); as carriers for presenting foreign epitopes (Sadeyen, 2003; Saini and Vrati, 2003); for the chemical conjugation of peptides (Kang, 2009); and for the delivery of antigenic molecules (Storni, 2004; Alvarez-Lajonchere, 2006). VLPs may induce potent immunity by continuously priming dendritic cells (Wingard, 2008). Immunization of mice with a semipurified recombinant capsid protein from Dengue-2 Virus (produced in *E. coli*) has been reported to confer protection against challenge of the same Dengue-2 virus (Amexis and Young, 2006).

Exposure to nucleocapsid proteins for antigen presentation may enhance immune responses (Lazo, 2010). Evidence of this include a corresponding virus humoral response increased production of interferon-gamma by spleen cells, induced dendritic cell maturation and secretion of cytokines stimulating CD4+ and CD8+ T-cells (Shresta, 2004). Additionally, the uptake of VLPs by dendritic cells may polarize cells toward a cytotoxic response. Oligodeoxynucleotides as adjuvants are capable of enhancing cell-mediated immunity; oligodeoxynucleotides packaged into VLP's are particularly effective (Riedl, 2002; Gil, 2009). In addition to neutralizing antibodies, an antiviral response achieved utilizing VLPs might be produced through cell-mediated cytotoxicity (Sedlik, 1997; Greenstone, 1998) or complement activation. Long term humoral and cellular protective responses have been demonstrated in baboons (Jeong, 2004) and chimpanzees (Elmowalid, 2007) immunized with Hepatitis-C VLPs containing either structural proteins or oligodeoxynucleotides. Data evidence production of nucleotide-defective and nucleotide-deficient virion particles with morphologically altered phenotypes upon exposure of HIV-infected host cells to platinum(IV) compound, FX101. Formation of these virus-like particles may account for observed long term virus control in FIV-infected cats.

A20 Proteins

Cytoplasmic A20 is a zinc finger protein with ubiquitin-modifying activity. Ubiquitin, a small protein rich in lysine residues, is covalently attached to numerous proteins by ligases. Ubiquitylation affects protein stability, function, and intracellular localization; sorting to the proteosome by ubiquitin results in degradation.

Human A20 is a 790-residue protein comprising seven zinc fingers of the Cys2/Cys2 type at the C-terminus. Importantly, A20 is a negative regulator of nuclear factor kappa beta (NF-κB) signaling and activator protein-1; in dendritic cells, down-regulation of A20 results in dendritic cells with enhanced T-cell stimulatory capacity (Breckpot, 2009). A20 is also a negative regulator of the toll-like receptor and tumor necrosis factor (TNF) receptor signaling pathways, controlling the maturation, cytokine production and immunostimulatory potency of dendritic cells (Song, 2008). A20 expression is up-regulated by either TNF-alpha or lipopolysaccharide (LPS) stimulation. The effect of Pt(IV) compounds on proteins such as A20 may impact associated functions.

Prion Proteins

Transmissible Spongiform Encephalopathies (TSE) are a unique class of neurodegenerative diseases where the disease agent is a prion protein. Prion protein binds copper in 4 tandem repeats of PHGGGWGQ (SEQ ID NO: 17); adjacent histidines (H96 and H111) may also bind copper. In addition to copper, other metals have been associated with Prion protein—notably zinc ($Zn^{2+}$). Zinc is also the only metal other than copper that induces PrP endocytosis and inhibits fibril formation in synthetic prions (Perera and Hooper, 2001; Walter, 2007).

Zinc Fingers and DNA Regulation

The regulation of DNA by zinc fingers is well known. Whether Pt(IV) compounds could interact with zinc fingers within the nucleus would depend upon their transport into the compartment and selectivity requirements. Nonspecific interactions could be overcome by association with specific proteins or oligonucleotides. Cobalt(III) oligonucleotides, for example, are reported to selectively target Snail family zinc transcription factors (Harney, 2009).

The ubiquitous transcription protein Sp1 contains a zinc finger domain of the CysCysHisHis (CCHH) type, binding to the GC box elements of DNA. Sp1 interacts with numerous factors (Deniaud, 2009). It is possible that certain Pt(IV) compounds could interact with such zinc domains, especially if positively charged. The cellular role of CCHH-type zinc domains in affecting protein interactions is proposed to be much greater than their role in DNA binding (Brayer, 2008), and thus possibly self-limiting. The number of zinc finger domains per protein would also contribute to an optimization of the therapeutic use (Koellensperger, 2007).

SUMMARY OF THE INVENTION

The present invention is directed to the modulation of zinc-binding domains or zinc-binding sites by platinum(IV) compounds. Viral nucleocapsid proteins, for example, contain two highly conserved zinc-binding domains critical to genomic RNA packaging and chaperoning; transfer RNA annealing; integrase-mediated strand-transfer; virus assembly and budding; Gag trafficking and processing; and temporal control of reverse transcription. Certain platinum(IV) compounds coordinate with zinc-binding domains and alter associated functions; zinc-binding sites are known therapeutic targets. Diseases and infections currently known to be therapeutically targeted through zinc-binding sites include certain viruses, trypanosomatids, specific proteins and immunomodulatory pathways. Modulation of zinc-binding domains by platinum(IV) compounds also produces immature virion particles and virus-like particles, useful for humoral, cell-mediated and complement immune responses, or as vectors.

This application also pertains to compositions and use of platinum(IV) compounds to alter zinc-binding sites, zinc-binding domains, zinc metalloproteins or zinc-associated proteins. Such interactions alter specific activities of these zinc-binding sites and associated protein functions, therefore offering therapeutic value (Anzellotti and Farrell, 2008; de Rocquigny et al., 2008; Jacobsen et al., 2007).

We will paste the claims here and turn them into paragraphs.

BRIEF DESCRIPTION OF THE DRAWINGS

FIG. 8A-8B are comparative ultraviolet-visible spectra of the F2 peptide zinc-binding domain associations with various metals.

FIGS. 9A-D are mass spectrograms comparing platinum (IV) and zinc(II) binding to the F2 peptide zinc-binding domain by matrix-assisted laser desorption ionization (MALDI) time of flight (TOF) spectroscopy.

DETAILED DESCRIPTION OF PREFERRED EMBODIMENTS

Figure 1A:
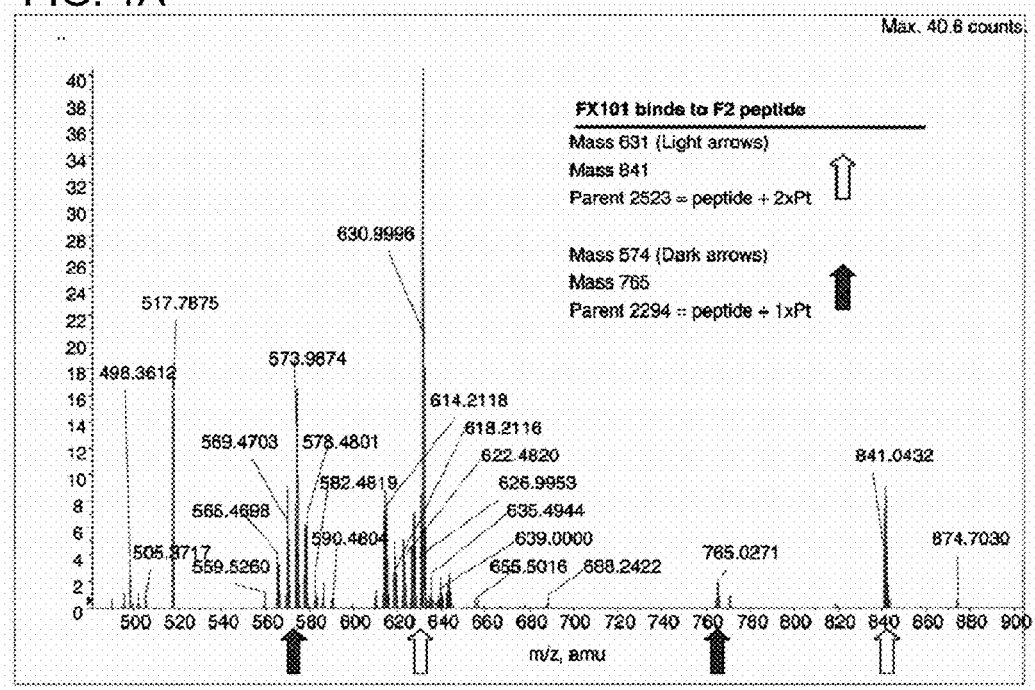
FIGS. 1A-1B are mass spectrograms of platinum bound to F2 peptide following incubation with Pt(IV) compound incubated with HIV-1 zinc-binding domain peptide sequence, F2 (FIG. 1A), and the magnified characteristic platinum isotopic distribution pattern (FIG. 1B) of the peptide-bound metal.

A detailed description of the preferred embodiments of the invention will now be presented with reference to FIGS. 1A-9D.

The interactions noted above in the Background between zinc-coordinating peptide domains, or zinc-binding sites, and certain platinum(IV) compounds suggest specific and potential applications of use to modulate activities of these domains or motifs by their coordination/interaction with platinum(IV) compounds.

Since a number of viruses are known to require nucleocapsid proteins containing zinc-binding domains for replication and survival, altering this domain by coordination or interaction with platinum(IV) compounds impairs virus production, virion formation and proviral DNA incorporation, providing therapeutic value. Platinum compounds of the present invention have been shown to provide long term virus suppression in infected hosts. Furthermore, the production of immature virions by platinum(IV) exposure provides a source of virus-like particles useful in immunological applications.

Manner and Process of Making and Using the Invention

Oxidation of platinum compounds to platinum(IV) can be achieved by methods known in the art. Some of these methods include oxidation or oxidative addition by $H_2O_2$, $NO_2$, $Cl_2$, $Br_2$, $SO_2$, HCl, HBr, HI, HCN, HCOOR, $HClO_4$, $H_2S$, RNCS, $CS_2$, and others (see Cotton and Wilkinson, 1972, p. 774, for example). Substitution reactions may include precipitation of ligands by other metals such as silver(I) with the addition of a preferred ligand. Care must be taken to minimize coordination of two platinums to bridging ligands, and this can be accomplished in part by conducting the syntheses in excess of these ligands, selecting appropriate solvents and respective volumes, and controlling the kinetic conditions of the reactions. Lewis bases can be coordinated to metals through methods known in the art. Substitution reactions and trans-activating ligands provide control of desired products. Methods of purification are well known in the art.

Pt(IV) compounds providing trans-oriented halides and/or directly coordinated to the platinum atom are best suited for zinc-coordinated interactions. Alternatively, trans-coordinated leaving groups to Pt(IV) provide geometries suitable for coordinating with protein zinc domains. These requirements have been observed through mass spectrometric analyses. Examples of effective compounds include diamminotrihalonitroPt(IV), where one pair of halides are in trans, equatorial geometries. The optimal ratio of Pt(IV) compound will be one to one with each zinc domain, although greater ratios would also be possible. Preferred platinum compounds useful in these applications include compositions of the formula $[PtL_1L_2XYAB]$, where Pt is platinum(IV), of octahedral geometry; $L_1$ and $L_2$ are each Lewis Base-coordinating ligands, trans to each other; X and Y are each halides, sulfides or leaving (labile) groups, trans to each other; A and B can each be various ligands coordinating to platinum, in a trans geometry; halides or sulfides may provide additional beneficial coordinate sites. Such structures have previously been described in the literature and are disclosed in other applications. While Pt(II) compounds have been explored as potential zinc-domain-targeting compounds (Anzellotti, 2006), the use of Pt(IV) compounds is novel.

Synthesis of diamminotrichloronitroPt(IV) has been previously described. Using trans-diamminodichloroPt(II) as starting material (Sigma-Aldrich P1525), oxidation to Pt(IV) can be achieved by adding an equimolar amount of butylnitrite (Sigma-Aldrich 22-663-7) or other source of nitrite, into a mixture of the Pt starting material in a solvent such as water. Several drops of HCl (or other acid) can then be added to the mixture, until a blue or green color, for instance, evidences the initiation of oxidation. The mixture can then be stirred overnight, at room temperature. Several drops of hydrogen peroxide can then be added to provide further oxidation of the Pt transition state. An equimolar amount of HCl (or other acid) provides the sixth ligand, as the anion of the acid. Choice and substitution of the ligands are well known in the art. The product should be allowed to crystallize slowly from solution (over approximately one week), whereby the solid can be collected, recrystallized and purified by methods known in the art. Most of these products have low solubilities in physiological saline, and can thus be better solubilized with the use of 2% for example, of dimethylsulfoxide for therapeutic applications. The product from the above reaction would be diamminotrichloronitroPt(IV), retaining its trans geometries of the starting material.

Therapeutic use requires administration of an effective dose below the no observable adverse effects level (NOAEL) for a given organism in the treatment of a disease, infection, or condition. In felines for the treatment of feline immunodeficiency virus, this level was found to be equivalent to a bolus injection of 5 micromolar blood serum concentration, or 3 mg per kg per dose, twice weekly for a minimum of four weeks. At this dose, plasma viremia as measured by p24 antigen falls below detection limits and appears to have long term effects, beyond those attributable to residual concentrations of the administered compound.

In vitro, HIV-1 virion production is inhibited in a concentration-dependent manner using 10-20 micromolar concentrations. These concentrations also severely impair normal formation of virion progeny, resulting in immature phenotypes. Lower concentrations are also anticipated to be effective.

Example 1

Mass Spectrometry Evidences Direct Binding of Pt(IV) Compound Incubated with HIV-1 Zinc-Binding Domain Peptide Sequence, F2

Figure 1B:
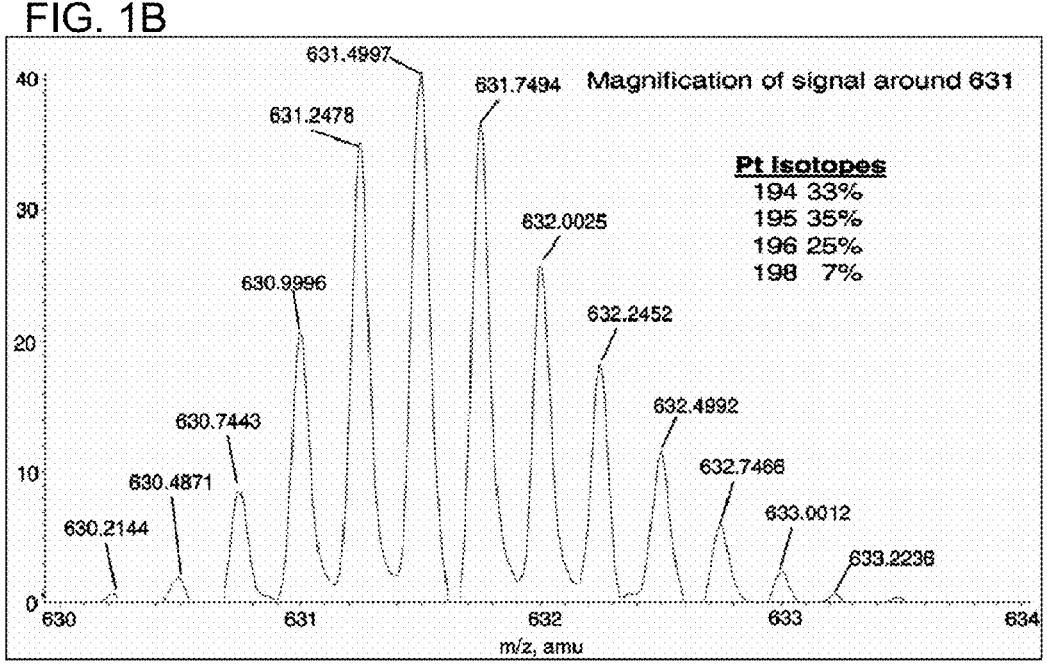

FIGS. 1A and 1B show Time of Flight (TOF) mass spectroscopy (MS) fragmentation pattern of the synthetic peptide F2, the carboxy-terminal zinc finger domain of HIV-1, bound to platinum. The F2 peptide sequence KGCWKCGKEG-HQMKDCTE was 95% pure with molecular weight 2069 (Peptide 2.0, Chantilly, Va.). Individual solutions containing 100 pmole/microliter of each F2 peptide, nitrotrichlorodiamminoPt(IV) (FX101) and $ZnCO_3$ in deionized water were prepared. Equal volumes of F2 with FX101, F2 with $ZnCO_3$, F2 with both FX101 and $ZnCO_3$ were mixed, resulting in four total peptide solutions. Full TOF MS was acquired on the QSTAR at the Johns Hopkins Proteomics Core Facility with 1 uL of original sample diluted 1:10 in 50% methanol with 0.1% formic acid/water and 3 uL of this mixture loaded onto the 2 um New Objective tip and nano-sprayed using ion spray voltage of 1200 eV; mass calibration of Csl mixture was performed prior to sample injection. Mass range 590 kDa (50%) to 10500 kDa (50%) was collected for 1.0 minute. Each spectrum confirmed the fragmentation masses of the peptide (m/z~690 and 1035) as well as specific metal-bound peptide fragments for each zinc and/or FX101. Blue arrows of FIG. 1A indicate matched FX101-peptide fragments m/z~631 and 831 of parent mass 2523 (two molecules of Pt compound per peptide); red arrows indicate matched FX101-peptide fragments m/z~574 and 765 of parent mass 2294 (1 molecule Pt compound per peptide). FIG. 1B highlights a magnified view of signals around m/z~631, showing the characteristic isotopic distribution of platinum (194, 195, 196 and 198) definitively identifying Pt-bound peptide. These results are consistent with data indicating reductions in virion production, production of immature phenotypes, and reductions in Gag protein processing, each shown to require nucleocapsid (NC) proteins comprising this zinc-binding domain. The nucleocapsid zinc fingers are a major target for therapeutics in HIV-1 and other zinc-binding domains (Williams, 2002; Mark-Danieli, 2005; Turner, 2006; Didierlaurent, 2008; Houzet, 2008)

Example 2

Figure 2:
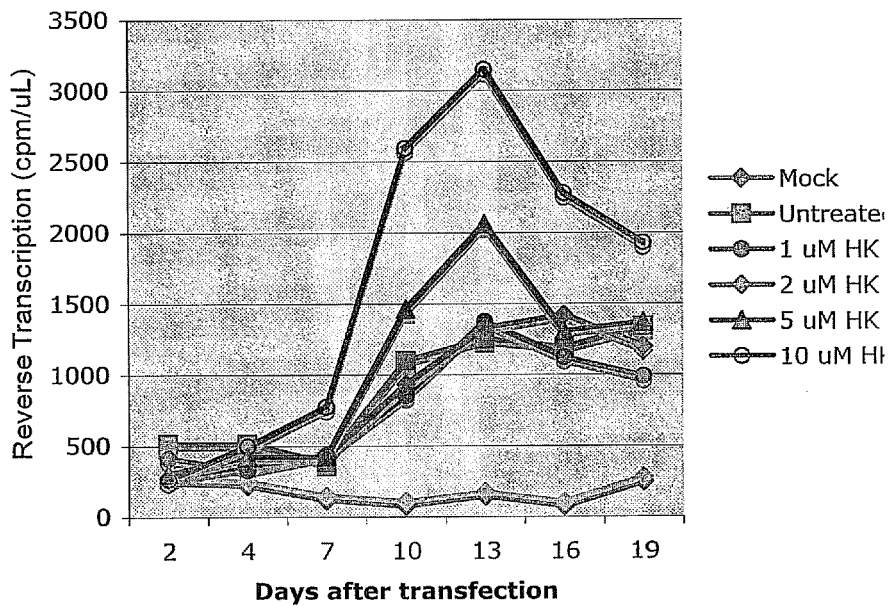
FIG. 2 is an increase in reverse transcription rate in HIV-1-infected monocyte-derived macrophages treated with platinum(IV) compound.
Figure 3:
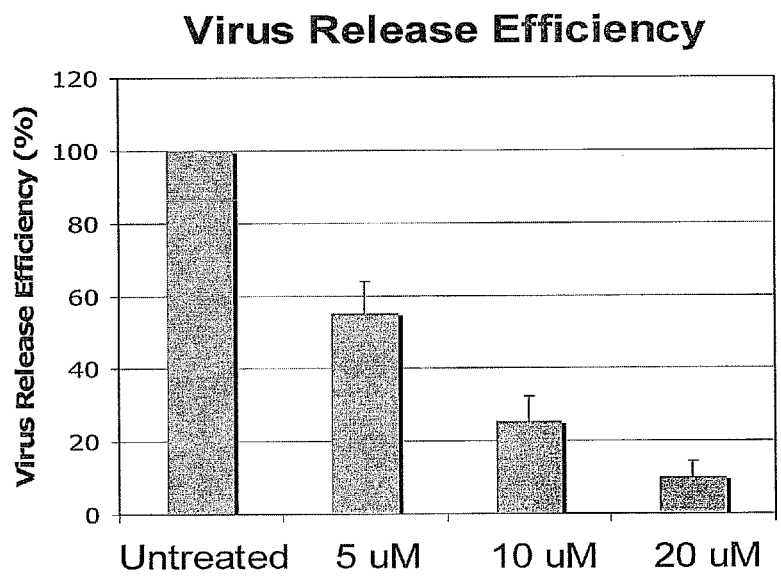
FIG. 3 is reduction of virus release by platinum(IV) compound in HIV-transfected HeLa cells.
Figure 4:
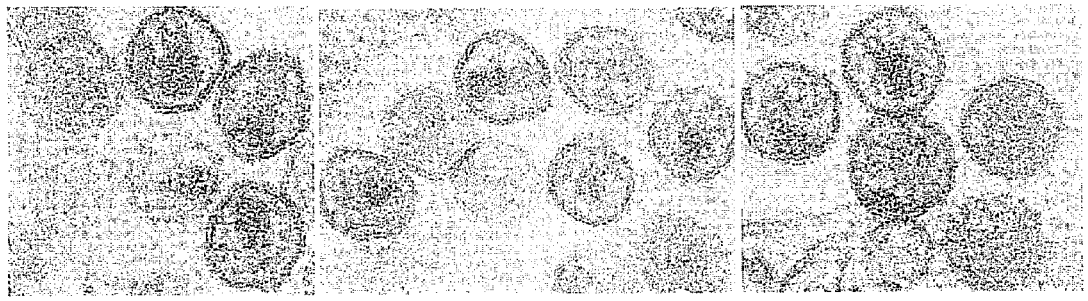
FIGS. 4A-4C are comparative electron micrographs images of virions produced by HIV-1-transduced HeLa cells produced in the presence of platinum(IV) compound.
Figure 4:
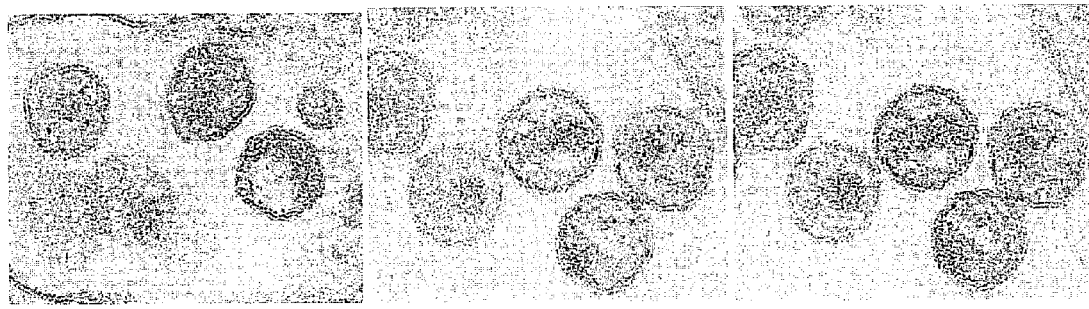
Figure 4:
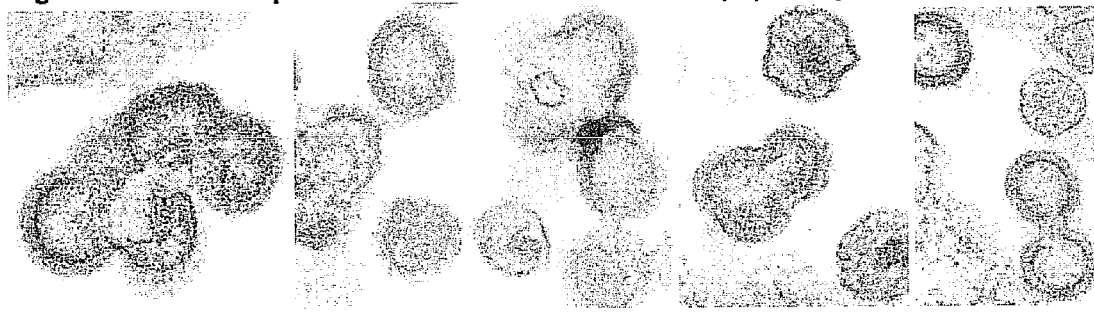
Figure 5:
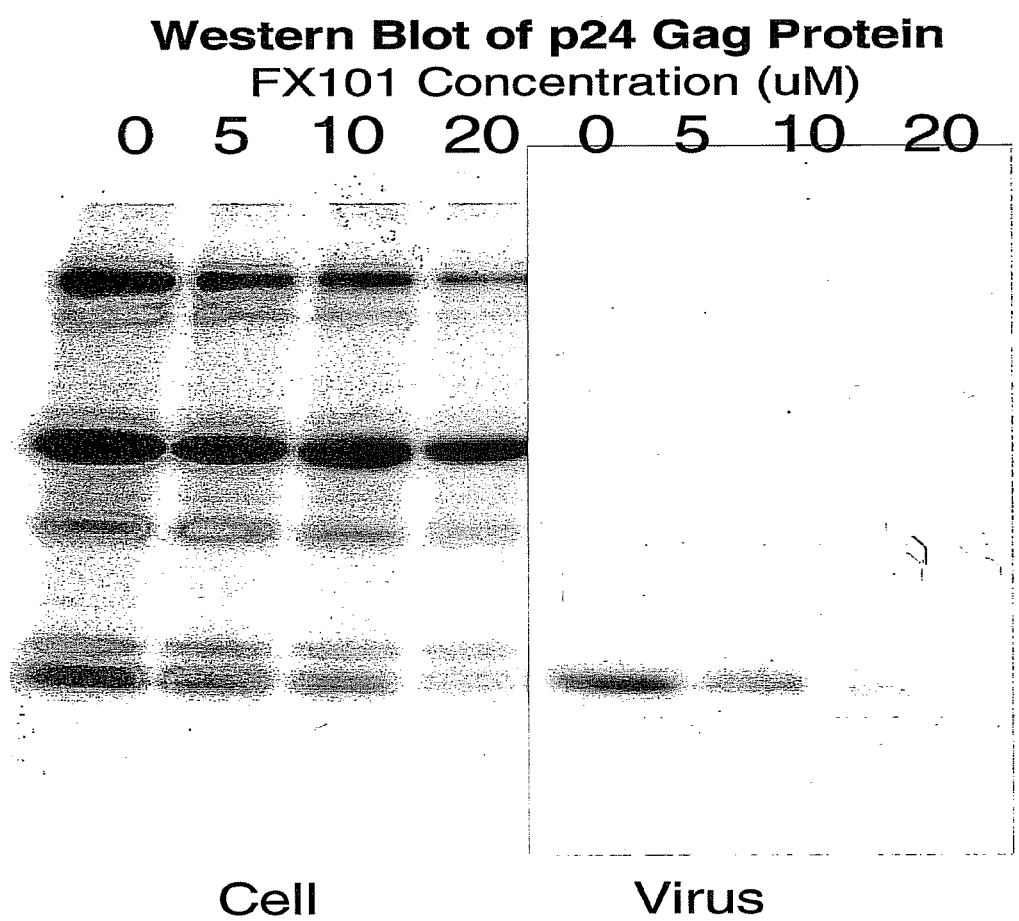
FIG. 5 is a Western Blot of decreasing p24 content in both host cell and virus particle with increasing platinum(IV) compound.

Platinum(IV) Compound Alters Reverse Transcription Rates in HIV-Infected Human Monocyte-Derived Macrophages Primary human monocyte-derived macrophages (MDM) were prepared by culturing elutriated monocytes in RPMI-1640 medium, supplemented with 10% fetal bovine serum for 5 to 7 days on ultra-low attachment plates. MDMs were detached from the plates and plated onto tissue culture dishes or microscope culture chambers. MDMs in 6-well plates were infected with WT pNL(AD8) virus stocks and $2 \times 10^6$ reverse transcriptase cpm/well. Various incubated concentrations of platinum(IV) compound ranging from 1 to 10 uM were compared with untreated (no drug) and mock-infected MDM reverse transcription rates (counts per minute/microliter). Medium in the MDM cultures was changed every two days and an aliquot was reserved for reverse transcriptase (RT) activity at each time point (Gousset, 2008). Increasing concentrations of FX101 (labeled as HK) do not inhibit reverse transcription in this system, but rather increase this rate as shown in FIG. 2. This activity parallels that observed by Mark-Danieli et al. (2005) by certain zinc finger mutations of the nucleocapsid protein; other investigators have reported decreases or no changes in transcription rates with various mutations (Ramboarina, 2004; Houzet, 2008). These results also distinguish between reported activities of platinum(IV) compounds as signal transducers and activators of transcription (STAT) inhibitors, which would produce reductions in this measure. Increasing the efficiency of reverse transcription initiation is detrimental to viral replication (Thomas and Gorelick, 2008). One role of nucleocapsid proteins is regulation of the transcription cadence in virally-infected cells.

Example 3

Inhibition of Virus Release by Platinum(IV) Compound in HIV-Transfected HeLa Cells Both HIV-1 virus release efficiency and p24 Gag proteins are greatly reduced by FX101 as compared with untreated HIV-1-transfected HeLa host cells (FIG. 3); these results parallel our feline MBM T-lymphoblastoid studies. Briefly, HeLa cells were transfected (calcium phosphate method) with the full-length, infectious HIV-1 molecular clone pNL4-3 to examine single-cycle particle production (Freed, 1994). Transfected cells were metabolically radiolabeled, and cell- and virus-associated proteins were immunoprecipitated and quantified as previously described (Waheed and Freed, 2008). Virus release efficiency was reduced in a concentration-dependent manner with FX101 as compared with untreated controls. Other experimentation with transfected HeLa and HEK-293 cells suggest that FX101 did not act as a direct inhibitor of viral transcription or infectivity, although these latter activities may depend upon the experimental system and/or cell type(s).

Example 4

Comparative Electron Micrographs of Virions Produced by HIV-1 Transfected HeLa Cells Exposed to Platinum(IV) Compound Electron micrographs illustrate the production of immature virions from HIV-1-transfected HeLa cells when cultivated at both 10 and 20 uM FX101 concentrations (FIGS. 4B-4C) as compared with untreated control cells (FIG. 4A). Virions collected from HeLa cells 24 hours post-transfected with pNL4-3 HIV-1 were treated with or without FX101 for 2 hours, washed with phosphate-buffered saline, pelleted by ultracentrifugation, fixed with buffer containing 2% glutaraldehyde and 0.1M sodium cacodylate as described (Freed, 1994), and analyzed by electron microscopy. These images reveal comparative distortions of both viral core and corresponding membranes of viral progeny, consistent with published images of immature virion particles having a thick electron-dense outer shell and an electron-lucent center lacking a typical cone-shaped core, produced by nucleocapsid mutant virions (Tanchou, 1998). Mutational deletion of either or both zinc finger domains of the nucleocapsid protein also produces morphologically altered virions, reduces virion release and alters RNA packaging (Houzet, 2008). The failure of nucleocapsid protein proteins to chaperone viral RNA together with the failure to form the nucleocapsid membrane reflects two roles of nucleocapsid proteins involving zinc finger domains. Obstruction of virion assembly may create impotent virions while maintaining antigens for host humoral immune response as virus-like particles. Note the absence of condensed core proteins within the particles, alterations in membrane spaces, formation of indiscreet virion particles and irregular shapes with increasing exposure to platinum (IV) compound. The formation of virus-like particles may partially explain the long term antiviral effects evidenced by FIV studies in cats, where both proviral loads and plasma viremia were profoundly reduced many months post treatment.

Example 5

Reduction of p24 Gag Protein with Increasing Platinum(IV) Concentration by Western Blot Analysis Virion assembly has been demonstrated to require viral Gag proteins (Freed, 1998); Gag precursors independently induce virus-like particles in mammalian cells (Adamson, 2009; Luttge, 2009). In vitro, this process occurs in the presence of nucleic acids and a cofactor (Campbell, 1999; Campbell, 2001). Immature particles fail to consolidate an outer membrane, emphasizing the critical role of Gag proteins in the assembly process (Didierlaurent, 2008). As virions bud from the host membrane, viral protease cleaves p55 Gag into its final mature components: matrix (p17), capsid (p24), nucleocapsid (p7) and p6, each designated by its apparent molecular weight. The absence of mature p24 from pNL4-3- transfected HeLa cells and viral progeny (FIG. 5), as described in Kiernan (1998) by Western blot using anti-p24 monoclonal antibody (Advanced Biotechnologies, Columbia, Md.) evidences the concentration dependent effect of FX101 upon maturation of virus. Effects may extend across the Gag polyprotein and its components, further compounding activities.

Example 6

Feline Immunodeficiency Virus Studies

Currently available antiretrovirals require daily dosing, often in combination therapy. Two $12^+$-year old specific-pathogen-free domestic female cats infected >5 years with the Petaluma strain of FIV were used in this study. The animals were housed individually in a climatized animal facility in accordance with standards, had ad libitum access to fresh water and food, and were sedated with Tiletamine/Zolazepam intramuscularly prior to any procedure. The cats weighed from 3-5 kg each. Three weeks before initiation of the treatment and at scheduled times, samples were collected for hematological and virological analyses. The cats received 9 intravenous doses of 3 mg/kg FX101 over 4.5 weeks (2× weekly). No local reactions or adverse clinical indicators due to treatments were observed during the complete study.

Plasma Viremia

Viral RNA extracted from plasma using the QIAmp viral RNA kit (QIAGEN), was reverse transcribed and amplified by reverse transcription TaqMan PCR. Reverse transcription and amplification conditions, and minimum detection limits of the assay (100-200 copies/mL plasma) are described elsewhere (Pistello, 2005). This measure represents viral presence in circulation, reflecting potential infectivity and productive synthesis of viral particles.

Proviral Load (in Peripheral Blood Mononuclear Cells)

Genomic DNA was extracted from the PBMC using the QIAamp DNA Blood Mini kit (QIAGEN). Proviral DNA was quantified from 0.4 ug genomic DNA by TM-PCR under the same conditions used for cDNA amplification except that the reaction mixture volume was 25 ul (n=3). The sensitivity of the assay was 100 copies/ug genomic DNA (Pistello, 2005). Proviral load varied over the course of treatment, but measured much lower than baseline pretreatment measures both 6 and 9 months later (27 and 38 weeks, respectively). This measure reflects viral integration into the host PBMCs, primed for production of viral particles with commencement of transcription. It is highly noteworthy that the proviral load reduced significantly even long after final treatment (+9 months). This is indicative of viral clearance and immune recovery, including apoptotic elimination of virally-infected cells. Viral reservoirs, such as those of macrophages and monocytes, have prevented eradication of lentiviruses (Nicastri, 2008).

Drug Preparation 0.1664 g FX101 was dissolved into 30 mL 15% DMSO/PBS and stirred overnight. This solution was sterile-filtered using a 20-mL syringe fitted with a 0.2 µM Sarstedt filter. Each dose was administered under anesthesia, a 1.5 mL venous injection using a 2.5 mL syringe fitted with a 22G 1¼-in. needle (latex free). Feline BR weighed 3.2 kg at the start of the experiment and CF weighed 2.8 kg. Each received 8.3 mg drug with each dose, so dosages were 2.6 mg/kg for BR and 3.0 mg/kg for CF.

CBC Measures

The hematological counts were performed with EDTA blood using the QBC-Vet Autoread Hematology System counter (IDEXX Laboratories Inc., Westbrook, Me., USA). This system measures hematocrit, hemoglobin concentration, and number and percent of total leukocytes, granulocytes, combined lymphocytes and monocytes, eosinophils platelets, and reticulocytes.

The control cat experienced a kidney infection prior to the September 6 sample; the BR cat experienced a uterine infection (documented history, ongoing) prior to the October 4 sample. These data are noted in the tables. Table 3 summarizes total WBCs over time for each cat. Absence of increased myelosuppression attributable to drug treatment is noted (Tables 3-7, recognizing that these felines presented with severe immunological impairments. Initially presenting with both leukopenia (<5500 cells/µL) and lymphopenia (<1500 cells/µL), both conditions persisted throughout the study with slight fluctuations. However, the absence of anemia (defined by <24% hemtocrit, Table 6) and thrombocytopenia (defined by <150,000 platelets, Table 7) were noted. While not necessarily indicative of disease progression, all these measures are therapeutically important and suggest an avoidance of immunosuppressive mechanisms typically associated with platinum therapeutics.

TABLE 3

Total White Blood Cell Counts Unaffected by Drug Treatment (Counts/µL)

| | Baseline Measures | | Treatment Measures | | | Post Measures | |
|---|---|---|---|---|---|---|---|
| | | | 30-Aug. | 4-Sep. | 20-Sep. | 4-Oct. | 20-Oct. |
| | 2-Aug. | 23-Aug. | (+7 d) | (+12 d) | (+28 d) | (+42 d) | (+58 d) |
| Control (infected) | — | 3900 | 4700 | 7900* | 2300 | 2500 | — |
| HK Inhibitor (cat BR) | — | 5200 | 4600 | 4300 | 3800 | 15500* | — |
| HK Inhibitor (cat CF) | — | 4800 | 4400 | 4500 | 4200 | 4800 | — |

*indicates local infection, unrelated to treatment

TABLE 4

Total Lymphomonocyte Counts Unaffected by Drug Treatment (Counts/μL)

|  | Baseline Measures | | Treatment Measures | | | Post Measures | |
| --- | --- | --- | --- | --- | --- | --- | --- |
|  | 2-Aug. | 23-Aug. | 30-Aug. (+7 d) | 4-Sep. (+12 d) | 20-Sep. (+28 d) | 4-Oct. (+42 d) | 20-Oct. (+58 d) |
| Control (infected) | — | 1300 | 2000 | 1800* | 1000 | 1300 | — |
| HK Inhibitor (cat BR) | — | 1000 | 1800 | 1200 | 1100 | 1400* | — |
| HK Inhibitor (cat CF) | — | 1300 | 1300 | 1400 | 1300 | 1500 | — |

*indicates local infection, unrelated to treatment

TABLE 5

Granulocytes (Neutrophils) Unaffected by Drug Treatment (Counts/μL)

|  | Baseline Measures | | Treatment Measures | | | Post Measures | |
| --- | --- | --- | --- | --- | --- | --- | --- |
|  | 2-Aug. | 23-Aug. | 30-Aug. (+7 d) | 4-Sep. (+12 d) | 20-Sep. (+28 d) | 4-Oct. (+42 d) | 20-Oct. (+58 d) |
| Control (infected) | — | 2600 | 2700 | 6100* | 1300 | 1200 | — |
| HK Inhibitor (cat BR) | — | 4200 | 2600 | 3100 | 2700 | 14100* | — |
| HK Inhibitor (cat CF) | — | 3500 | 3300 | 3100 | 2900 | 3300 | — |

*indicates local infection, unrelated to treatment

TABLE 6

Hematocrit (% Red Blood Cell Hemoglobin) Unaffected by Drug Treatment

|  | Baseline Measures | | Treatment Measures | | | Post Measures | |
| --- | --- | --- | --- | --- | --- | --- | --- |
|  | 2-Aug. | 23-Aug. | 30-Aug. (+7 d) | 4-Sep. (-1- 12 d) | 20-Sep. (+28 d) | 4-Oct. (+42 d) | 20-Oct. (+58 d) |
| Control (infected) | — | 29 | 30 | 31* | 21 | 21 | — |
| HK Inhibitor (cat BR) | — | 27.1 | 21.1 | 25 | 25.2 | 16.5* | — |
| HK Inhibitor (cat CF) | — | 28.2 | 23.8 | 23.4 | 24.8 | 27.4 | — |

*indicates local infection, unrelated to treatment

TABLE 7

Absence of Thrombocytopenia (Platelets <150,000) Due to Drug Treatment (in Thousands of Counts/μL)

|  | Baseline Measures | | Treatment Measures | | | Post Measures | |
| --- | --- | --- | --- | --- | --- | --- | --- |
|  | 2-Aug. | 23-Aug. | 30-Aug. (+7 d) | 4-Sep. (+12 d) | 20-Sep. (+28 d) | 4-Oct. (+42 d) | 20-Oct. (+58 d) |
| Control (infected) | — | 126 | 148 | 144* | 176 | 165 | — |
| HK Inhibitor (cat BR) | — | 212 | 157 | 215 | 210 | 110* | — |

TABLE 7-continued

Absence of Thrombocytopenia (Platelets <150,000) Due to Drug Treatment (in Thousands of Counts/μL)

|  | Baseline Measures | | Treatment Measures | | | Post Measures | |
| --- | --- | --- | --- | --- | --- | --- | --- |
|  | 2-Aug. | 23-Aug. | 30-Aug. (+7 d) | 4-Sep. (+12 d) | 20-Sep. (+28 d) | 4-Oct. (+42 d) | 20-Oct. (+58 d) |
| HK Inhibitor (cat CF) | — | 168 | 196 | 195 | 178 | 158 | — |

*indicates local infection, unrelated to treatment

Table 8 illustrates measures of plasma viremia from the two test cats, "BR" and "CE" relative to the treatment period, receiving intravenous injections of FX101 twice weekly over four weeks. Each blood sample was taken immediately prior to drug injection for the scheduled dosing, August 23-September 30. This provided two pretreatment samples as baseline measures, 3 samples during treatment, and two post-treatment samples; note the addition of an unscheduled sample October 20. A significant reduction in plasma viremia occurred in both cats over two weeks until measures were below detection for the remaining duration of treatment. Following the last dosage, the first post-treatment results were ambiguous, with one cat experiencing a strong rebound and the other remaining below detection. This difference may be attributable to a uterine infection experienced by cat "BR" at this time—a historically frequent occurrence for this cat. It is well known that lipopolysaccharides (LPS) induce lentiviral replication, and this may therefore be related. Cat "CF" continued to show low levels of viremia, and both cats demonstrated significantly lower viremia as compared with baseline measures even 4 weeks to 9 months past the final dosage, in the absence of additional therapies, suggestive of an immune-based recovery. Current studies (in progress) are validating these results, with significant reductions in proviral load extending over several months.

TABLE 8

Plasma Viremia (Number of Viral RNA Copies/mL Plasma)

|  | Pretreatment Period Measures | | | | | Treatment Period* | | | Post Treatment Measures | | | |
| --- | --- | --- | --- | --- | --- | --- | --- | --- | --- | --- | --- | --- |
|  | | | | | | | | | | | Mar. | Jun. |
| Date | Jan. 1, 2006 | Feb. 1, 2006 | Mar. 1, 2006 | Aug. 2, 2007 | Aug. 23, 2007 | Aug. 30, 2007 | Sep. 4, 2007 | Sep. 20, 2007 | Oct. 4, 2007 (+2 wk) | Oct. 20, 2007 (+4 wk) | 27, 2008 (+27 wk) | 12, 2008 (+38 wk) |
| BR | 4932 | 3864 | 2819 | 4282 | 6974 | 1249 | <100 | <100 | 10517 | 1057 | <200 | <200 |
| CF | 1461 | 6557 | 3072 | 2582 | 8841 | 1300 | <100 | <100 | <100 | 898 | <200 | <200 |

TABLE 9

Proviral Load in PBMC (Number proviral DNA copies/ug genomic DNA)

|  | Pretreatment Period | | Treatment Period* | | | Post Treatment Measures | | | |
| --- | --- | --- | --- | --- | --- | --- | --- | --- | --- |
| Date | Aug. 2, 2007 | Aug. 23, 2007 | Aug. 30, 2007 | Sep. 4, 2007 | Sep. 20, 2007 | Oct. 4, 2007 (+2 wk) | Oct. 20, 2007 (+4 wk) | Mar. 27, 2008 (+27 wk) | Jun. 12, 2008 (+38 wk) |
| BR | 8560 | 6867 | 6476 | 1048 | 4660 | 14724 | 2790 | 1000 | 1350 |
| CF | 4148 | 4472 | 5803 | 6738 | 4152 | 14500 | 4211 | 1250 | 1747 |

*Treatment period 23-Aug. to 20-Sep.; blood collected prior to dosing

Circulating CD4+ and CD8+ T-Lymphocytes

Numbers of peripheral $CD4^+$ and $CD8^+$ T-lymphocytes in the blood were determined by labeling with mouse monoclonal antibodies to feline $CD4^+$ (FE1.7B12) and feline $CD8^+$ (FE1.10E9), obtained from Peter F. Moore, University of California, Davis, Calif. Bound primary antibodies were detected using FITC-conjugated anti-mouse IgG1 (Space-Serotec, Milan, Italy), and the samples were analyzed on a FACScan flow cytometer (Becton Dickinson, San Jose, Calif.). Both a negative (no drug) and positive (integrase inhibitor cocktail) control are included with data from two HK inhibitor-tested felines. Final $CD4^+/CD8^+$ ratios remained higher in both tested felines as compared with controls at the conclusion of this study (Table 10).

weeks supports a distinct mechanism from the nucleotide/non-nucleotide reverse transcriptase, protease and infectivity inhibitors. Efficacy extends across diverse strains of FIV, in agreement with alterations by platinum(IV) compounds to the zinc-binding nucleocapsid domain being therapeutically targeted. It is anticipated that cotherapies targeting multiple mechanisms may eventually provide viral clearance for an infected host.

Example 7

Feline Blood Serum Measures Following Treatment

Test sera samples from select felines were analyzed using the Rules-Based Medicine (Austin, Tex.) human multi-ana-

TABLE 10

Relative CD4+/CD8+T-Lymphocyte Counts in Cats
Receiving Platinum(IV) Compound vs. Positive (HAART drugs) and Negative Controls

| | Pretreatment Period Measures | | | | | | | Treatment Period* | | Post Treatment | |
|---|---|---|---|---|---|---|---|---|---|---|---|
| Date | Nov. 1, 2005 | Dec. 1, 2005 | Jan. 1, 2006 | Feb. 1, 2006 | Mar. 1, 2006 | Aug. 2, 2007 | Aug. 23, 2007 | Aug. 30, 2007 | Sep. 4, 2007 | Oct. 4, 2007 (+2 wk) | May 8, 2008 (+33 wk) |
| Cat BR +FX101 | 0.86 | 1.5 | 1.6 | 0.82 | 0.84 | 1.1 | 1.2 | 1.5 | 1.5 | 1.9 | 1.8 |
| Cat CF +FX101 | 0.85 | 2.0 | 0.92 | 1.1 | 1.2 | 1.3 | 1.2 | 1.3 | 1.6 | 1.4 | 1.6 |
| Control (FIV+) | nd | nd | nd | nd | nd | 1.0 | 0.93 | 0.97 | 1.1 | 1.1 | nd |
| Control (FIV+) +ART | nd | nd | nd | nd | nd | 1.3 | 0.74 | 1.6 | 1.2 | 1.2 | 1.2 |
| | nd | nd | nd | nd | nd | 0.76 | 0.80 | 1.0 | 1.4 | 0.73 | nd |

Reproducible Results for FIV Inhibition in Cats

Figure 6:
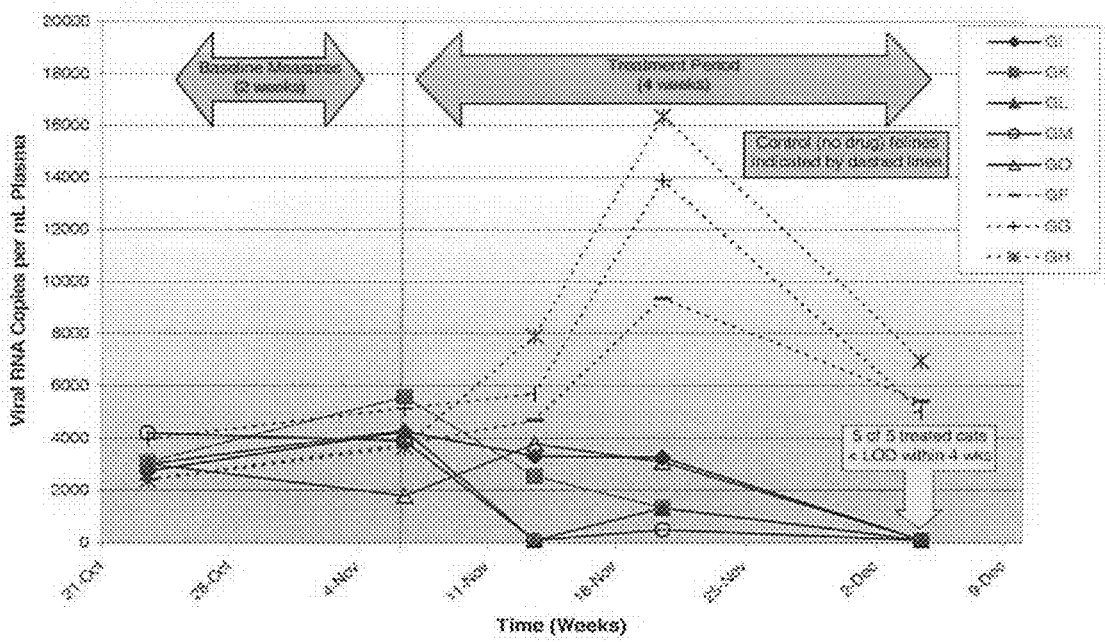
FIG. 6 is a summary of an FIV-infected cat study where five of eight cats received six doses of platinum(IV) compound over four weeks, resulting in plasma viremia levels below detection limit for all five cats.
Figure 7:
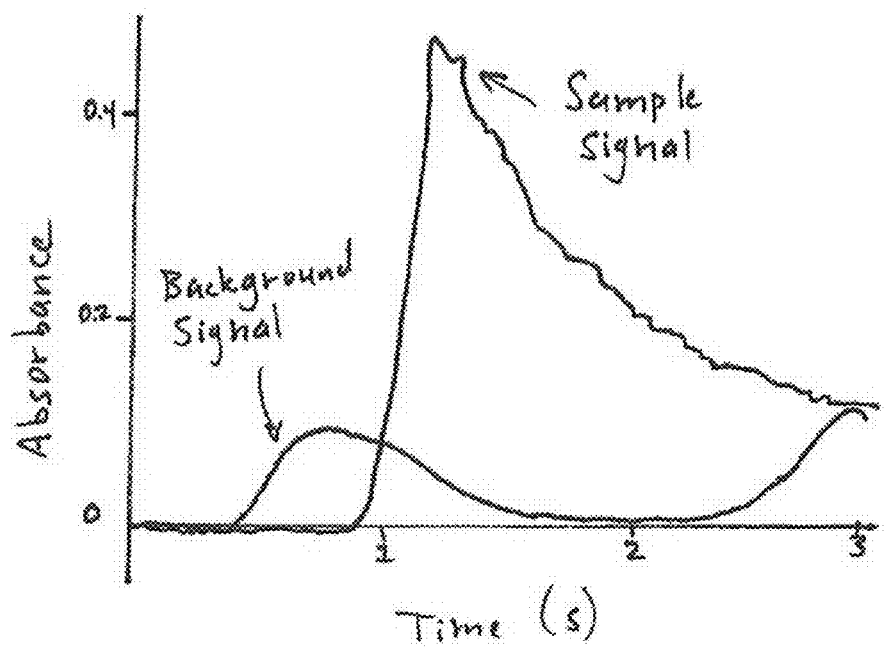
FIG. 7 is a platinum absorption spectrum by graphite furnace analysis, produced from the cerebrospinal fluid sample of a cat following intravenous delivery of platinum(IV) compound.

Eight specific-pathogen-free domestic female cats infected >2 years with the M2 strain of FIV were used in another study. Cats were housed individually in a climatized animal facility in accordance with standards, had ad libitum access to fresh water and food, and were sedated with Tiletamine/Zolazepam intramuscularly prior to any procedure. The animals were divided into two groups, with five receiving FX101 in 10% DMSO/saline (treated) and three receiving only 10% DMSO/saline (control). Prior to initiation of the treatment and at scheduled times, samples were collected for hematological and virological analyses. The cats received 6 intravenous doses of 3 mg/kg FX101 over four weeks. Cats were matched by birthdates and infection dates with similar viral blood plasma viremia levels at the onset of the study. Following 6 intravenous doses of FX101, all five of the FX101-treated cats demonstrated plasma viremia levels below the detection limit of the assay while the three control cats demonstrated active viremia (FIG. 6). Current antretrovirals are required on a daily basis; the efficacy of six doses of treatment over four lyte for 90 measures from a single sample of less than 0.5 mL. The assay uses immunofluorescent beads to simultaneously measure antibody recognition to individually identifiable colored beads, each conjugated with a specific antibody, within a single well plate. Blood samples were drawn preceding (pretreatment) and following (post treatment) one-month FX101 treatment (from felines in Example 6), and are compared with two uninfected control felines. Human cross-reactive antibodies are commonly used for felines, and are relative rather than quantitative measures. Reductions in TNF-alpha and MMP-2 are evident in treated cats; TIMP-1 (Tissue Inhibitor of Metalloproteinases) is not associated with the downregulation of MMP-2. Both MMP-2 and MMP-9, as well as MCP-1, are considered important contributors to the penetration of virally-infected cells across the BBB (Webster, 2006). Additional comments follow the table.

TABLE 11

Relative Blood Serum Measures from Cats by Immunofluorescent Bead Analysis

|  | Calcitonin (pg/mL) | IL-13 (pg/mL) | CD40L (ng/mL) | IL-8 (pg/mL) | TNF-alpha (pg/mL) | IL-12p70 (pg/mL) | MMP-2 (ng/mL) | TIMP-1 (ng/mL) |
|---|---|---|---|---|---|---|---|---|
| Control 1 (uninfected) | <6.0 | 26 | 0.036 | <3.5 | 1.9 | 15 | <LOW> | 6.8 |
| Control 2 (uninfected) | <6.0 | 22 | 0.054 | <3.5 | 2.4 | 19 | <LOW> | 8.0 |
| Cat BR pretreatment | 7.6 | 15 | 0.036 | <3.5 | 1.3 | 22 | 3000 | 6.5 |
| Cat CF pretreatment | 11 | 12 | 0.029 | <3.5 | 1.0 | 31 | 3150 | 9.8 |
| Cat BR post treatment | 2.9 | 27 | 0.017 | 4.1 | 0.91 | 38 | 2070 | 9.0 |
| Cat CF post treatment | 2.9 | 34 | 0.0067 | 5.7 | 0.57 | 51 | 2120 | 7.3 |

CD40L: CD40L (sCD40L) in paired samples of plasma and cerebrospinal fluid obtained from 25 HIV-infected individuals is significantly higher in both for cognitively impaired patients as compared with their unimpaired counterparts. CD40 signaling in microglia and monocytes synergizes with effects of TNF-alpha and lentiviral Tat proteins, amplifying inflammatory processes within the CNS and influencing neuronal survival (Sui, 2007).

IL-8: Interleukin-8 (CXCL8) is a CXC chemokine of the innate immune system primarily related to the recruitment of neutrophil granulocytes, thus also known as Neutrophil Chemotactic Factor. It is produced by macrophages, endothelial and epithelial cells; while other cells such as macrophages, mast cells, keratinocytes and endothelial cells are also responsive to it, through CXCR1 and CXCR2 receptors. Some of these productions are therefore self-regulating. IL-8 presents both as homodimers and monomers.

Decreased levels of IL-8 production in HIV-1 subjects have been measured. Notably, the reduced levels may increase susceptibility to pneumococcal infection in HIV-infected subjects (Gordon, 2005). IL-8 and RANTES (regulated upon activation normal T cell expressed and secreted) have been shown to suppress HIV-1 replication in macrophages, together with reducing the CCR5 receptor availability and sensitivity—CCR5 is a coreceptor for HIV-1 R5 variant infection (Csoma, 2006). Furthermore, patients identified to control virus replication during periods of structured HAART treatment interruptions and long-term nonprogressors (LT-NPs) exhibit greater CD8+ T-cell responsiveness to IL-8 through expression of CXCR1; contrastingly, this receptor was found to be downregulated during periods of uncontrolled viral replication in vivo. Therefore, IL-8/CXCR1 CD8+ T-cell cytotoxic potential may effectively control HIV-1 replication (Hess, 2004).

TIMP-1: Tissue Inhibitor of Metalloproteinases, is usually inversely related to MMP activities, but cannot account for the change in MMP-2 in these data.

Calcitonin is a protein produced primarily by the parafollicular (also known as C-cells) of the thyroid, and in many other animals in the ultimobranchial body. It acts to reduce blood calcium ($Ca^{2+}$), opposing the effects of parathyroid hormone. Procalcitonin is a prohormone of calcitonin; both have been identified as monocyte chemoattractants (Wiedermann, 2002). Serum procalcitonin levels are markedly elevated in sepsis and correlate positively with severity (Sexton, 2008). Procalcitonin concentrations distinguish between bacterial and viral infections, being lower in viral infections and inflammatory diseases. These increased levels in FIV-infected felines, therefore, may be more indicative of blood brain barrier penetration in late-stage lentiviral infections.

IL-12p70: During early infection, HIV-infected individuals have higher numbers of virus-specific cytotoxic T lymphocytes (CTLs) that initially reduce the viral load but later fail. Dysregulation of cytokines like interleukin-12 (IL-12) result from the interaction of HIV-1-specific T cells with antigen-presenting cells, resulting in CTL dysfunction. Secretion of IL-12 is reduced as HIV progresses, correlating with impaired CTL function (Gupta, 2008). Data suggest a role of IL-12 in priming CD4(+) T cells to stimulate CD8(+) T cells. In addition, IL-12 can downregulate a constitutively active G protein-coupled receptor that contributes to the development of Karposi's sarcoma in AIDS patients (Yarchoan, 2007). Functional IL-12(+) dendritic cells may stabilize HIV disease progression (Daniel, 2008). Impaired response of Natural Killer cells in HIV-progressors as compared to LTNP's and HIV-negative donors correlates with a decreased production of IL-12 (Saez, 2007).

TNF-alpha: Tumor Necrosis Factor-alpha is secreted by macrophages, monocytes, neutrophils, T-cells and NK-cells in response to different stimuli including interferon, IL-2, GM-CSF (granulocyte macrophage colony-stimulating factor) and others. Its production typically increases with the progression of HIV/AIDS, and is hypothesized to act via lipid raft-dependent stimulation of the HIV-1 provirus present in such cellular reservoirs as mononuclear phagocytes (Herbein, 2008). Human brain microvascular endothelial cells (HBMEC) exposed to HIV-1-infected macrophages increase expression of tumor necrosis factor-alpha-induced proteins, interferon (IFN)-inducible genes, intercellular adhesion molecule-1, transcription factors of the nuclear factor-kappaB family, and signal transducer and activator of transcription-1, leading to BBB (blood-brain-barrier) impairment (Chaudhuri, 2008). Direct inhibition of TNF-alpha through Tristetraprolin may is also possible.

IL-13: Both IL-4 and IL-13 downregulate expression of the monocyte receptor CXCR4, while IL-13 also downregulates CCR5; both these receptors are utilized by lentiviral infections. Additionally, both IL-4 and IL-13 inhibit virus replication in monocytes (Creery, 2006). Acute exposure of PBMCs derived from HIV-infected subjects to IL-13 increased recall T cell lymphoproliferative responses against antigens through enhanced antigen presentation together with increased CD86 (B7.2) expression (Papasavvas, 2005). This T-cell activation and survival may also be evidenced in the CD4+/CD8+ ratios of Table 10 of Example 6.

Matrix Metalloproteinases (MMPs): MMPs include 23 human types, identified by number and/or other names. While their overall function relates to extracellular matrices such as collagens, they are also important in angiogenesis, antigen processing and presentation, inflammation, chemokine/cytokine regulation, and other physiological functions. Dysfunction in MMPs has been identified for diseases including arthritis, cirrhosis, glaucoma, lupus, multiple sclerosis and HIV-1 associated dementia (Webster, 2006).

Of special interest are the gelatin-binding metalloproteinases, MMP-2 and MMP-9 (Gelatinases A and B, respectively). These have a unique fibronectin-repeat catalytic domain, a standard prodomain, which initially folds over a $Zn^{2+}$ catalytic zinc-binding site, and a $Ca^{2+}$-containing homopexin-like carboxyl end related to substrate specificity. MMPs are normally regulated. However, HIV infection of monocytes and macrophages generally results in elevations of both MMP-2 and MMP-9 and reduction in their regulators, tissue inhibitors of metalloproteinases, TIMPs (Webster, 2006). Experimental evidence relates these MMP activities to increased permeability of the blood-brain-barrier (BBB), infiltration of inflammatory cells, and progression of HIV-1 associated dementia (Power, 1993). MMP's -1, -2, -3 and -9 are found at higher mRNA and protein levels in brain tissues of HAD patients (Ghorpade, 2001). Both Collagen type IV and laminin, substrates of MMP-2 and -9, are reduced in these tissues, the former from the basal membrane of the BBB and the latter from neurons (Buttner, 1996; Chen, 1997). Elevated MMP-9 is also found in the cerebral spinal fluid of HIV-infected HAD patients (Conant, 1999). The relationship between MMP-9 and dementia is further emphasized in SIV-mac239-infected macaque monkeys, which overexpressed MMP-9 in their microglia, and developed significant loss of cognitive and motor skills as compared with controls (Berman, 1999).

Interestingly, monocyte activation rather than infection appears to be the key mechanism for monocyte migration across the BBB and altered MMP production (Persidsky, 1997). Tat protein upregulates MMP-9 in monocytes, but can be blocked by tyrosine phosphatase inhibitors, which also block NF-kappaB and prevent IkappaB-alpha degradation (Kumar, 1999). Neurotoxicity induced by Tat proteins can be inhibited by the MMP (-2, -3, -9, -13 and -14) inhibitor prinomastat in murine models (Johnston, 2001). HAD remains the leading cause of morbidity in AIDS.

Example 8

Blood Brain Barrier Penetration of Platinum(IV) Compound

Most antiretrovirals cannot penetrate into the CNS where both direct and indirect viral burden lead to neuronal damage. Although neurons do not directly support HIV infection, soluble factors and neurotoxins produced by CNS-resident infected cells—such as microglia and astrocytes—are known to lead to neuronal death. Additionally, viral and bacterial proteins can lead to neuronal death through inflammatory responses of CNS-resident cells, even in the absence of direct viral infection. Virus components such as Tat (Trans-activator of transcription) and glycoprotein gp120 are known to cause indirect injury to neurons (Valcour, 2010). Further, antiretrovirals differ in their ability to permeate the BBB in therapeutic concentrations where the viral burden is compartmentally distinct from blood periphery and lymphoid tissue.

Cerebrospinal fluid (CSF) from cats BR and CF of Example 6 were collected under sedation following humane animal practices. CSF (0.5-1 ml) samples were collected within 15 minutes of FX101 peripheral intravenous (IV) injection to examine for drug penetration into the CNS. Importantly, this analysis was conducted upon the final IV drug treatment, which would most likely evidence resistances to CNS uptake as experienced by other CNS-penetrable drugs. Instead, CSF concentrations (analyzed by graphite furnace atomic absorption spectrometry for this inorganic complex as illustrated for cat "BG") were equivalent to blood serum concentrations of 5 micrograms/mL in both cats, supporting a continuing unimpeded penetration into the vital CNS compartment through the blood brain barrier.

Example 9

Comparative Ultraviolet-Visible Absorption Spectra of Zinc Domain F2 with Various Metals The synthetic peptide F2, the carboxy-terminal zinc finger domain of HIV-1, was examined by ultraviolet-visible absorption spectroscopy for its interaction with various metals. Spectral analyses of metal coordination to peptides by this method are published (Frankel, 1988; Blasie and Berg, 2000). The F2 peptide sequence, KGCWKCGKEG-HQMKDCTE (SEQ ID NO 1: KGCWKCGKEG-HQMKDCTE) was 95% pure with molecular weight 2069 (Peptide 2.0, Chantilly, Va.). Stock solutions of $2\times10^{-4}$ mole/liter F2 peptide were prepared in phosphate buffered saline (PBS) without calcium or magnesium; known stock concentrations of Fe(II), Co(II), Zn(II) and Pt(IV) metals were also prepared in PBS. One to one ratios of F2 peptide with each metal were individually combined at room temperature with final concentrations of $10^{-4}$ mole/liter, and spectra were collected at various times using a Nanodrop Spectrophotometer (Thermo Scientific, Inc.) having a xenon flash lamp and requiring <2 microliters of sample deposited directly onto an optical lense. FIGS. 8A and 8B illustrate profound spectral differences between metals known to interact with zinc-finger domains, Fe(II), Co(II), and Zn(II), and the Pt(IV) compound nitrotrichlorodiamminoPt(IV) (noted here as FX). Changes in absorption at ~250 nm could be observed over the course of minutes upon addition of FX101 to F2 peptide solution, indicating charge transfer between the platinum metal and sulfur ligands (Frankel, 1988). This rapid association was unique to FX, even after 12 hours of incubation with F2 with metals at 4° C. The strong coordination of FX to F2 peptide can be seen in FIG. 8B in the upper curve; Co(II), Fe(II) and Zn(II) coordination with F2 peptide are each depicted in decreasing order, with comparative absorptions at 250 nm of 0.066, 0.047 and 0.039, respectively, versus Pt(IV) at 0.118; shapes of absorption curves also emphasize these differences. FX:F2 coordination absorption curves increased quickly at ~250 nm over the course of 20 minutes at room temperature. These data suggest a strong interaction of Pt(IV) compound FX with the zinc-finger binding domain characteristic of nucleocapsid proteins. Alterations in the metal-coordinating capacity have extensive implications to nucleocapsid functions as nucleotide chaperones, structural components, in the production and maturation of virions, among other activities.

Example 10 p25 Antigen Evaluation of Antiviral Activity in MBM Cells

Antiviral activity in MBM was determined by inoculating 200 Tissue Culture Infectious Doses 50% FIV Petaluma (Talbott, 1989) in 100 μL RPMI 1640 medium into quadruplicate wells of 96-well microplates containing $2\times10^5$ cells in 100 μL medium. The cultures were monitored by measuring FIV p25 capsid protein (Lombardi, 1994) release in the supernatants after 7 days of incubation at 37° C. in 5% $CO_2$ (Table 12). Half the media (without drug) was replaced on days 2 and 6 after infection and initial drug exposure. This reduces the actual contact time with drug as the experiment progresses, suggesting an early time cellular event leading to the observed responses. At 7 days, drug #4 completely eliminated (100%) all measures of virus at both concentrations used, 5 and 20 μM; drug #1 resulted in <30% inhibition by day 7. Drugs are identified as: CPA-7 (#1); NAD (#2); cisplatin (#3) and FX101 (#4). Drugs #1, #3 and #4 are Pt(IV)'s while drug 2 is a Pt(II). Both drugs #1 and #2 have been shown to inhibit STAT3, yet are either completely ineffective (#2) or insignificantly effective (#1). A minimum of 50% inhibition in vitro is required to offset viral infectivity and replication in vivo. These data demonstrate significant differences between Pt(IV) compounds, suggesting that select ligands and their orientations with respect to the octahedral geometry of Pt(IV) compounds define a distinct subset of effective compounds.

TABLE 12 p25 Viral Antigen Measured by OD
P25 (OD) 7 DAYS POST INFECTION

| Drug # | 1 | 2 | 3 | 4 |
|---|---|---|---|---|
| | conc 5 μM | | | |
| | 1.093 | 1.06 | 1.04 | 0 |
| | 1.122 | 1.136 | 1.021 | 0 |
| | 1.068 | 1.113 | 0.986 | 0 |
| average | 1.0943 | 1.103 | 1.0157 | 0 |
| std dev | 0.0221 | 0.0318 | 0.0224 | 0 |
| | conc 20 μM | | | |
| | 0.788 | 1.13 | 1.014 | 0 |
| | 0.825 | 1.099 | 1.033 | 0 |
| | 0.836 | 1.081 | 0.993 | 0 |
| average | 0.8163 | 1.1033 | 1.0133 | 0 |
| std dev | 0.0205 | 0.0202 | 0.0163 | 0 |

K+ = 1.195 (OD of virus-infected control cells)
K− = 0.08 (OD of non-infected control cells)

Example 11

MALDI-TOF MS Analysis of Metal Binding to F2 Zinc Finger Peptide

Solutions of F2 zinc finger peptide in phosphate-buffered saline without calcium or magnesium (see Example 1) alone or mixed with zinc and/or platinum compounds were analyzed by MALDI-TOF (matrix-assisted laser desorption/time-of-flight) MS (mass spectrometry). Briefly, the samples comprised 1:1 ratios of F2 peptide with metals in phosphate buffered saline without calcium or magnesium at $2\times10$ moles/liter concentrations. Additionally, samples containing both Zn(II) and Pt(IV) metals with F2 peptide in a 1:1:1 ratio were analyzed, as were various Pt(IV) and Pt(II) compounds mixed with F2 peptide solutions. Samples were considered to be at equilibrium after 12 hours stored at 4° C. Volumes of 0.5-1.0 microliters for each sample were individually spotted with or without dilution at 1:10, 1:100 or 1:1000 (~165-193 pmole/microliter) in DHB matrix (Laser Biolabs, France). The Mass Spectrometer Voyager DE STR (Applied Biosystems) with Instrument Control Panel (v 5.1) and Data Explorer (v4.0) sample analysis used an ACTH reflector; accelerating voltage of 25000 eV; grid voltage 63.8%; mirror voltage ratio 1:12; laser rep rate 20.0 Hz band width 500; vertical scale 50; bin size 0.5; acquisition mass range 800-4000 Da; Delay 155, 165 or 200 sec; laser intensity 1480-1590; 75 nsec delay time; C1 or C2 standards in DHB matrix. DHB matrix was 10 mg/ml in either 50% acetonitrile/water (with or without 0.1% TFA) or 50% ethanol/water (without 0.1% TFA). Samples were used without clean up. Spectra are illustrated in FIGS. 9A-9D.

F2 Peptide ("Pep") Alone

There are two main sets of peaks in the F2 peptide mass spectrum. One of these is a group of peaks between 2063-2069 Da which seems to be overlapping of two or more peaks, possibly with neutral monoisotopic masses 2062.84 Da, 2064.84 Da (most intense) and 2066.84 Da. These kinds of spectrum are often observed if a peptide contains 2 to 6 cysteines, which make form 1-3 S—S bonds, and all these species could be present simultaneously, so the spectrum is the result of 2-3 overlapping spectra. Peaks at m/z 4128-4135 Da are likely dimer(s) of the main peptide. The complexity of the spectrum suggests presence of more then one monomer. Dimers could be spectrometric (formed during the MS ionization), chemical or both.

Peptide Plus Zinc ("Pep+Zn")

Zinc ions have a mass of 65.39 amu; coordinated F2-Zn mass peaks can be seen at mass 2133.49 Da (2069+65=2134). The large group of peaks between 2063-2069 Da are similar to peptide alone.

Peptide Plus Platinum(IV) ("Pep+FX")

The main group of peaks include at least two overlapping peaks characteristic of cysteines (see note above) with neutral mass within 2451.82-2457.82 Da, singly charged ions at m/z 2452.82-2458.82 Da. These could be peptide mass +195×2-n2H, where n=1, 2, 3) Da or coordination of the peptide to the full molecule of FX (380.15 Da, recovered from MALDI-TOF analysis; not shown), although the expected mass falls slightly below the actual peak range (2065+380=2445 Da) and may indicate peptide oxidation or addition/substitution of ions in the resulting complex. The set of peaks at m/z 2452.82-2458.82 Da is unique to the F2 peptide+FX spectral complex and was not produced by the isomer of FX; platinum (II) compounds resulted in only slight coordination with F2 peptide, only slightly different from peptide alone (not shown). While MALDI-TOF MS is not quantitative, relative peak heights are proportional to relative amounts of species. The same peaks as in the Pep alone sample are present, but of very low intensity as compared to the main peak. There is a significant reduction in the peak heights of peptide alone (m/z 2063-2069 Da) as compared with metal-coordinated peptide (m/z 2452.82-2458.82 Da) in spectra of FX. These peaks further display the characteristic isotopic distribution of platinum isotopes (FIG. 9D). There is also a group of low intensity peaks at ~2296-2324 Da. Samples containing FX were more difficult to ionize, suggesting they may be more thermodynamically inert.

Peptide Plus Platinum(IV) Plus Zinc ("Pep+FX+Zn")

This spectrum is more similar to that of peptide plus FX, suggesting thermodynamic competition of FX over zinc for the nucleocapsid zinc finger binding domain since 1:1:1 F2:FX:Zn ratios were mixed. Evidence for continued zinc-peptide binding appears in a small set of peaks ~m/z 2133 Da is similar to that for the peptide plus zinc spectrum (see above), although a much more intense set of peaks at ~m/z 2452.82-2458.82 Da indicative of FX coordination with F2 peptide (see above) and a broad set of peaks between ~m/z 2258-2342 and ~m/z 2471-2542 may include both zinc and platinum simultaneously coordinated to peptide.

DEFINITIONS AND METHODS

Platinum(IV) compounds are well known in the art. Since zinc-binding domains have specific architectures, the ligand requirements for Pt(IV) species most useful for interacting with a particular zinc-binding site sequence may include geometries of either cis or trans arrangements optimally meeting the zinc-binding site requirements. Further preferred embodiments may include ligands providing conjugation to antibodies or vehicles, other therapeutics, charged species, other metals, light-activated release, or polymers. Structures contemplated to be candidates include:

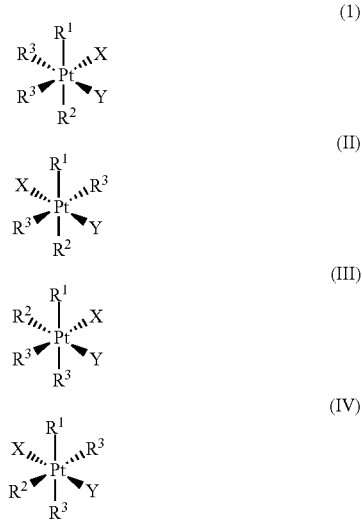

wherein X and Y are, independently, any halogen, —CN, —SCN, —NCS, —$NO_2$, —ONO, —$OHSO_3$, —$OH_2PO_3$, —$OHSO_2$, —$SO_3H$, —OH, —$OR^2$, —$OS(CH_3)_2$, —$OCOR^2$, —$OCOOR^2$, —$OSO_2CH_3$, —SH, —$SR^2$, —$S_2CN(R^2)_2$, —$OSiO_3$, —$OBO_2H$, —$OHSeO_2$, —NH-COH, —$NH_2CHO$, —$NH_2CH_2OH$, —$NH_2C(OH)_3$, —$NH_2CH(OH)_2$, or —$NHCOR^2$, or X and Y together form a ring structure selected from the group consisting of cyclobutane dicarboxylate (CBDCA) $(OCOC_4H_6OCO)^{2-}$; oxalate $(C_2O_4)^{2-}$, malanato $(OOCCH_2COO)^{2-}$, dithiocarbamate $((R^2)_2NCS_2)^-$, acetylacetonate $(CH_3COCHCOCH_3)^-$, carboxylate $(CO_2R^2)^-$, sulfate $(SO_4)^{2-}$, phosphate $(HPO_4)^{2-}$, selenate $(SeO_4)^{2-}$, silicate $(SiO_4)^{2-}$, diborate $(B_2O_5)^{4-}$, (acetylacetonate $(OCCH_3CH_2CH_3O)^-$, ethylene diamine $(H_2C_2H_4NH_2)$, bis(diphenylphosphino)ethane (dppe) $((C_6H_5)_2PC_2H_4P(C_6H_5)_2)$, bis(dimethylphosphino)ethane (dmpe) $((CH_3)_2PC_2H_4P(CH_3)_2)$, 2,2'-bipyridine $((NC_5H_4)_2)$ and glyme $(CH_3OCH_2CH_2OCH_3)$;

$R^1$ is —$NO_2$, —ONO, —CN, —SCN, —NCS, —COOH, $COOR^2$, —CHO, —COR, —OH or —$SO_3H$;

$R^2$ is any halogen, —COOH, —OH, —$NH_2$, —$HSO_3$, —$OHSO_3$, —$OH_2PO_3$, —$OBO_2$, —$OHSiO_3$, —$OHSeO_2$, an alkyl, alkoxy, cycloalkyl, cycloalkoxy, aryl, aryloxy, alkycarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, heteroaryloxycarbonyl, heterocycloalkoxy, or heterocycloalkoxycarbonyl, any of which can be optionally substituted with any halogen, —COOH, —OH, —$NO_2$, —$NH_2$, —$HSO_3$, —$OHSO_3$, —$OH_2PO_3$, —$OBO_2$, —$OHSiO_3$, —$OHSeO_2$, N-alkyl, alkyl, alkoxy, cycloalkyl, cycloalkoxy, aryl, aryloxy, alkycarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl;

$R^3$ is —$NH_3$, —$NH_2R^2$, —$NH(R^2)_2$, —$N(R^2)_3$, —$NH_2COR^2$, —$NH_2COH$, —$NH_2CHO$, —$NH_2CH_2OH$, —$NH_2C(OH)_3$, —$NH_2CH(OH)_2$, —$OCH_3$, —$OR^2$; any hydride, halogen, sulfur, oxygen, selenium, tellurium, phosphorous or nitrogen species; any alkene, alkyne or aromatic species;

or $R^3$, $R^3$, X, and Y together comprise porphyrin or phthalocyanine;

or $R^3$, $R^2$, X, and Y together comprise porphyrin or phthalocyanine;

or a pharmaceutically acceptable salt thereof.

As used herein, alkyl means straight or branched chain, saturated or mono- or polyunsaturated hydrocarbon groups having from 1 to 20 carbon atoms, and C1-X alkyl means straight or branched chain alkyl groups containing from one up to X carbon atoms. For example, $C_{1-6}$ alkyl means straight or branched chain alkyl groups containing from one up to 6 carbon atoms. Alkoxy means an alkyl-O-group in which the alkyl group is as previously described. Cycloalkyl includes a nonaromatic monocyclic or multicyclic ring system, including fused and Spiro rings, of from about three to about 10 carbon atoms. A cyclic alkyl may optionally be partially unsaturated. Cycloalkoxy means a cycloalkyl-O-group in which cycloalkyl is as defined herein. Aryl means an aromatic monocyclic or multicyclic carbocyclic ring system, including fused and Spiro rings, containing from about six to about 14 carbon atoms. Aryloxy means an aryl-O— group in which the aryl group is as described herein. Alkylcarbonyl means a RC(O)— group, where R is an alkyl group as previously described. Alkoxycarbonyl means an ROC(O)— group where R is an alkyl group as previously described. Cycloalkylcarbonyl means an RC(O)— group where R is a cycloalkyl group as previously described. Cycloalkoxycarbonyl means an ROC(O)— group, where R is a cycloalkyl group as previously described.

Heteroalkyl means a straight or branched chain having from one to 20 carbon atoms and one or more heteroatoms selected from nitrogen, oxygen, or sulfur, wherein the nitrogen and sulfur atoms may optionally be oxidized, i.e., in the form of an N-oxide or an S-oxide. Heterocycloalkyl means a monocyclic or multicyclic ring system (which may be saturated or partially unsaturated), including fused and spiro rings, of about five to about 10 elements wherein one or more of the elements in the ring system is an element other than carbon and is selected from nitrogen, oxygen, silicon, or sulfur atoms. Heteroaryl means a five to about a 14-membered aromatic monocyclic or multicyclic hydrocarbon ring system, including fused and Spiro rings, in which one or more of the elements in the ring system is an element other than carbon and is selected from nitrogen, oxygen, silicon, or sulfur and wherein an N atom may be in the form of an N-oxide. Arylcarbonyl means an aryl-CO-group in which the aryl group is as described herein. Heteroarylcarbonyl means a heteroaryl-CO-group in which the heteroaryl group is as described herein and heterocycloalkylcarbonyl means a heterocycloalkyl-CO— group in which the heterocycloalkyl group is as described herein. Aryloxycarbonyl means an ROC(O)— group, where R is an aryl group as previously described. Heteroaryloxycarbonyl means an ROC(O)— group, where R is a heteroaryl group as previously described. Heterocycloalkoxy means a heterocycloalkyl-O— group in which the heterocycloalkyl group is as previously described. Heterocycloalkoxycarbonyl means an ROC(O)— group where R is a heterocycloalkyl group as previously described.

Examples of saturated alkyl groups include, but are not limited to, methyl, ethyl, N-propyl, isopropyl, N-butyl, tert-butyl, isobutyl, sec-butyl, N-pentyl, N-hexyl, N-heptyl, and N-octyl. An unsaturated alkyl group is one having one or more double or triple bonds. Unsaturated alkyl groups include, for example, ethenyl, propenyl, butenyl, hexenyl, vinyl, 2-propynyl, 2-isopentenyl, 2-butadienyl, ethynyl, 1-propynyl, 3-propynyl, and 3-butynyl. Cycloalkyl groups include, for example, cyclopentyl, cyclohexyl, 1-cyclohex-enyl, 3-cyclohexenyl, and cycloheptyl. Heterocycloalkyl groups include, for example, 1-piperidinyl, 2-piperidinyl, 3-piperidinyl, 3-morpholinyl, 4-morpholinyl, tetrahydrofu-ran-2-yl, tetrahydrofuran-3-yl, tetrahydrothien-2-yl, tetrahy-drothien-3-yl, 1-piperazinyl, 2-piperazinyl, and 1,4-diazabi-cyclooctane. Aryl groups include, for example, phenyl, indenyl, biphenyl, 1-naphthyl, 2-naphthyl, anthracenyl, and phenanthracenyl. Heteroaryl groups include, for example, 1-pyrrolyl, 2-pyrrolyl, 3-pyrrolyl, furyl, thienyl, imidazolyl, oxazolyl, thiazolyl, pyrazolyl, pyridyl, indolyl, quinolinyl, isoquinolinyl, benzoquinolinyl, carbazolyl, and diaza-phenanthrenyl.

As used herein, halogen means the elements fluorine (F), chlorine (Cl), bromine (Br), and iodine (I).

As used herein, Lewis base means any atom or polyatomic species capable of providing and electron pair in a chemical bond, including any hydride, halogen, sulfur, oxygen, selenium, tellurium, phosphorous or nitrogen species; any alkene, alkyne or aromatic molecule.

The term pharmaceutically acceptable salts means salts of the platinum compounds of the invention which are prepared with acids or bases, depending on the particular substituents present on the subject compounds described herein. Examples of a pharmaceutically acceptable base addition salts include sodium, potassium, calcium, ammonium, or magnesium salt. Examples of pharmaceutically acceptable acid addition salts include hydrochloric, hydrobromic, nitric, phosphoric, carbonic, sulfuric, and organic acids like acetic, propionic, benzoic, succinic, fumaric, mandelic, oxalic, citric, tartaric, maleic, and the like. Pharmaceutically acceptable salts of platinum compounds of the invention can be prepared using conventional techniques.

It will be appreciated by those skilled in the art that certain of the platinum compounds of the invention may contain one or more asymmetrically substituted carbon atoms which can give rise to stereoisomers. All such stereoisomers, including enantiomers, and diastereoisomers and mixtures, including racemic mixtures thereof, are contemplated within the scope of the present invention. Platinum compounds of the present invention have been shown to associate with zinc-binding peptide domains. These associations result in alterations to protein activities, especially those related to nucleotide chaperoning and packaging; transfer RNA annealing; integrase-mediated strand transfer; virus assembly and budding; Gag protein trafficking and processing; and temporal control of reverse transcription known to require intact zinc-bound nucleocapsid proteins. Importantly, production of virus-like particles, morphologically and/or genetically defective, result from contact of virus-infected cells with platinum(IV) compounds. Both in vitro and in vivo studies have confirmed alterations to nucleocapsid protein functions while exhibiting low to no apparent complications of toxicity. Select platinum (IV) compounds have been shown to directly coordinate to the zinc-binding peptide sequence of the nucleocapsid protein to account for these observations.

Methods of the invention comprise modulating functions or structures associated with zinc-binding domains or zinc-binding sites. These are established therapeutic targets for a number of viruses, specific proteins, immunological pathways and other pathogens. In addition to the Retroviridae viruses HIV-1, HIV-2, SHIV, SIV, Fly, and HTLV-1, viruses known to require functional zinc domains or to coordinate zinc include but are not limited to: Picornaviridae (poliovirus, human coxsackievirus, hepatitis A virus), Flaviviridae (yellow fever virus, Dengue virus, West Nile virus, Kunjin virus, St. Louis encephalitis virus, hepatitis C virus), Togaviridae (rubella virus), Coronaviridae (human coronavirus, human SARS-associated coronavirus), Rhabdoviridae (rabies virus), Paramyxoviridae (human parainfluenza virus, measles virus, human respiratory syncytial virus), Filoviridae (Marburg virus, Ebola virus), Bornaviridae (Borna disease virus), Bunyaviridae (Hantaan virus), Arenaviridae (Lassa virus), and Reoviridae (human rotavirus). Additionally, proteins such as matrix metalloproteinases, Tat protein, Tristetraprolin and A20 protein are known to require coordination of zinc for their activities; as do proteins critical for survival and replication of trypanosomatids (malaria parasite). This application extends to zinc-binding sites in other systems whereby platinum(IV) compounds modulate the activities of proteins containing zinc-binding sites and provide utility.

In one embodiment, the method comprises contacting a cell with a platinum compound of the invention. In one embodiment, the cell is a tumor cell, cancer cell, viral-infected cell, immune cell, liver cell, heart cell, pancreatic cell, epithelial cell, endothelial cell, hematopoetic cell, stem cell, microglial cell, dendritic cell, neuronal cell, retinal pigment endothelial cell, adipocyte, osteoblast or a transformed cell. In another embodiment, the cell can be bacterial, parasitic, insect or viral. The cell can be a cell from a mammal, including human, monkey, chimpanzee, ape, dog, cat, cow, pig, and horse.

Zinc-binding domains or zinc-binding sites are typically characterized by a combination of cysteine and histidine residues. They can be classified by the type and order of these zinc-coordinating residues (e.g., $Cys_2His_2$, $Cys_4$, $Cys_2His$ Cys and $Cys_6$). One method classifies them into different "fold groups" based on the overall shape of the protein backbone in the folded domain such as the "classic zinc finger" ($Cys_2His_2$), treble clef, gag knuckle ($Cys_2His$ Cys) and zinc ribbon. Spacing between zinc-coordinating residues can be variable, with intermittent residues typically designated by the letter "X", as for the $Cys_2His_2$ zinc-binding domain sequence $X_2$-Cys-$X_{2,4}$-Cys-$X_{12}$-His-$X_{3,4,5}$-His, where X denotes any residue and the subscript refers to respective numbers of these. Synthetic or modified residues are envisioned to be appropriate in some applications. Coordination of zinc to other residues such as glutamate or aspartate (typically coordinating through an oxygen atom) are also possible, such as those found in the zinc-coordination sites of matrix metalloproteinases (Tallant, 2009), such as those sharing the sequence HEXXHXXGXXH, where H is histidine, E is glutamic acid and G is glycine.

Platinum compounds of the invention can be delivered to a target either through direct contact with the target or via a carrier. Targets include viruses, proteins, cells, toxins, bacteria, pathogens, or fungi. Carriers for delivering compositions to cells are known in the art and include, for example, a liposome or moiety or nanomaterial such as carbon nanoparticles. Another means for delivery of platinum compounds of the invention to a target comprises attaching the platinum compound to a protein, sugar or nucleic acid that is targeted for delivery to the target cell. Platinum compounds can be incorporated into polymers, examples of which include poly (D-L lactide-co-glycolide) polymer for intracranial delivery; poly[bis(p-carboxyphenoxy) propane:sebacic acid] in a 20:80 molar ratio (as used in GLIADEL); chondroitin, chitin, or chitosan. Of specific relevance are targeting methods suitable for immune cell types related to specific therapeutic needs.

The subject invention also concerns multiple methods for preventing or treating oncological disorders in a patient: inhibiting tumor metastasis, inhibiting cellular transformation, and/or activating both innate and immune responses. In one embodiment, an effective amount of a platinum compound of the present invention is administered to a patient having an oncological disorder and who is in need of treatment thereof. Importantly, methods of the invention describe unique targets distinct from DNA- or RNA-alkylation, but directed to proteins that are known to bind zinc metal to specific domains (zinc-binding domains, or to coordinate with zinc) for their activities such as matrix metalloproteinases. Such interactions have been shown to alter functions of zinc-binding domains. Methods of the invention can optionally include identifying a patient who is or may be in need of treatment for an oncological disorder. The patient can be a human or other mammal, such as a primate (monkey, chimpanzee, ape, etc.), dog, cat, cow, pig, or horse, or other animals having an oncological disorder. Means for administering and formulating platinum compounds for administration to a patient are known in the art, examples of which are described herein. Oncological disorders include cancers and/or tumors of the bone, breast, kidney, mouth, larynx, esophagus, stomach, testis, cervix, head, neck, colon, ovary, lung, bladder, skin (e.g., melanoma), liver, muscle, pancreas, prostate, eye (e.g., retinoblastoma), blood cells (including stem cells), and brain.

For the treatment of oncological disorders, the platinum compounds of this invention can be administered to a patient in need of treatment in combination with other antitumor or anticancer substances; or with radiation, electroporation, radio waves, immunotherapy, photodynamic therapy; or with surgical treatment to remove a tumor. These other substances or treatments may be given at the same as or at different times from the platinum compounds of this invention. For example, the platinum compounds of the present invention can be used in combination with mitotic inhibitors such as taxol or vinblastine, alkylating agents such as cyclophosamide or ifosfamide, antimetabolites such as 5-fluorouracil or hydroxyurea, DNA interchelators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively.

Many tumors and cancers have viral genome present in the tumor or cancer cells. For example, Epstein-Barr virus (EBV), Herpes Papillomavirus (HPV) and Hepatitus Virus C(HPVC) are each associated with a number of mammalian malignancies. The platinum compounds of the subject invention can be used alone or in combination with another anti-cancer and/or antiviral agent, such as ganciclovir, azidothymidine (AZT), lamivudine (3TC), maraviroc, raltegravir, etc., to treat patients infected with a virus that can cause cellular transformation and/or to treat patients having a tumor or cancer that is associated with the presence of viral genome in the cells. The platinum compounds of the subject invention can also be used in combination with viral-based treatments of oncologic disease.

Some platinum compounds of the present invention have also been shown to inhibit Signal Transducers and Activators of Transcription (STAT) activity (Turkson, 2004). Distinctions between these activities and platinum compounds of the subject invention are evidenced by differences in p24 antiviral activities, virion release efficiencies, toxicities, transcription rate inhibitions and zinc-binding domain interactions. Profound differences between platinum(II) compounds cisplatin and transplatin are well known.

Relatively low effective therapeutic concentrations and very low toxicities as compared with other platinum compounds provide distinct advantages. Furthermore, biological reduction of certain compounds of the invention leading to transplatinum(II) compounds exhibit much reduced toxicities as compared with cisplatinum(II) derivatives; these trans isomers have also demonstrated antiviral activities as compared with corresponding cis isomers. Platinum compounds of the invention can be tested for activity in suitable assays, such as virion release assays, proviral DNA incorporation assays, cytokine/chemokine production/sensitivity assays, receptor expression and functionality assays, etc. Most antiviral therapeutics inhibit early steps in virus infection; attention to the later steps of virus production must be considered. Long term control of viral loads suggest participation of immune responses, likely induced by the formation of immature virions, in vivo. Since immune cells and soluble proteins may also contribute to viral pathologies, in vitro assays may not fully reflect in vivo therapeutic capacities of these compounds. Further, these effects may be cell specific and transparent to single-cycle production assays.

The subject invention also concerns methods for preventing or treating bacterial, viral, fungal, parasitic or prion infections of a patient using a platinum compound of the invention, including the host immune responses to infections. In one embodiment, an effective amount of a platinum compound of the invention is administered to a patient to prevent or treat a bacterial or viral infection. Methods of the invention can optionally include identifying a patient who is or may be in need of treatment of a bacterial, viral, fungal or prion infection. The patient can be a human or other mammal, such as a primate (monkey, chimpanzee, ape, etc.), dog, cat, cow, pig, or horse, or other animal infected with a bacteria or virus. Bacterial infections that can be treated according to the present invention include at least those from *Staphylococcus, Streptococcus, Salmonella, Bacillus, Clostridium, Pseudomonas, Neisseria, Mycobacterium*, and *Yersinia*, inclusive of resistant strains. Viral infections that can be treated according to the present invention include, but are not limited to, those associated with human immunodeficiency, feline immunodeficiency virus (FIV), simian immunodeficiency virus (SIV), human T-cell leukemia virus (HTLV), Papillomavirus (e.g. human papilloma virus (HPV)), Polyomavirus (e.g., SV40, BK virus, DAR virus), orthopoxvirus (e.g., variola major virus (smallpox virus), Epstein Barr Virus (EBV), herpes simplex virus (HSV), hepatitis C virus, Rhabdovirus (e.g., Ebola virus) and cytomegalovirus (CMV). Platinum compositions of the present invention can also be used to treat bacterial, viral, or prion diseases in the presence of other therapies such as antimicrobials or antivirals. It is contemplated that these compounds interfere with zinc-binding domains critical to survival and replication of pathogenic vectors, including control of the immunological response.

Platinum compounds of the subject invention can be used to produce virus-like particles (VLPs). VLPs are useful for enhancing an immune response in a patient or to develop a vaccine in vitro, in vivo, or ex vivo. In one embodiment, a patient is administered a therapeutically effective amount of a platinum compound of the present invention to activate cellular and/or humoral immune responses either alone or in combination with an antigen, protein, peptide fragment, nucleotide, sugar or lipid, or any combination of these. In another embodiment, an effective amount of a platinum compound is introduced to an animal, such as a rabbit, together with an antigen (which may be a protein, peptide fragment, living or attenuated cell, virion, or sugar) to elicit the production of antibodies. In another embodiment, an effective amount of a platinum compound is introduced ex vivo to activate antigen-presentation responses for a patient in need of immune therapy. In another embodiment, a patient is administered a therapeutically effective amount of a platinum compound to stimulate immune responses in the presence of a pathogen. Methods of the invention can optionally include identifying a patient who is or may be in need of vaccine therapy. The patient can be a human or other mammal, such as a primate (monkey, chimpanzee, ape, etc.), dog, cat, cow, pig, or horse, or other animal. Platinum compounds of the invention are contemplated to alter zinc-binding domains, including those of nucleocapsid proteins, for example. Formation of immature, virus-like particles in this manner provides a platform for immunological applications.

Platinum compounds of the subject invention can also be used to treat patients infected with a parasitic organism, including the host immune responses to infection. In one embodiment, the patient is administered a therapeutically effective amount of a platinum compound of the present invention. Methods of the invention can optionally include identifying a patient who is or may be in need of treatment of a parasitic infection. The patient can be a human or other mammal, such as a primate (monkey, chimpanzee, ape, etc.), dog, cat, cow, pig, or horse, or other animal infected with a parasitic organism. Disease conditions that can be treated according to the present invention include, but are not limited to: *leishmania*, toxoplasmosis, schistosomiasis, trypanosomiasis, *pneumocystis*, malaria, and trichinosis. Parasitic organisms that can cause disease conditions treatable according to the present invention include, but are not limited to, *Leishmania, Toxoplasma, Schistosoma, Plasmodium*, and *Trypanosoma*. The subject invention can also be used to treat gastro-intestinal disorders caused by parasitic organisms such as: *Entamoeba, Giardia, Trichomonas*, and nematodes such as *Ascaris, Trichuris, Enterobius, Necator, Ancylostoma, Strongyloides*, and *Trichinella*. In another embodiment, a platinum compound of the present invention can be administered to patients prophylactically, wherein an uninfected patient is traveling to or will be present in an area where parasitic disease is prevalent or poses a risk to the patient. Accordingly, the patient can be treated with a composition of the present invention prior to the patient's exposure to or presence in the area where parasitic disease is prevalent or poses a risk and/or prior to infection with the parasitic organism.

Platinum compounds of the present invention can also be used to treat biological products in vitro that are contaminated with or suspected of being contaminated with a protein, peptide, virus or a bacteria or parasitic organism. Biological products that can be treated with a platinum compounds of the present invention include, but are not limited to, whole blood, fractionated blood, plasma, serum, whole organs, or parts of organs, and cells, including blood cells, muscle cells, skin cells, and neuronal cells, and products derived from cells. Products derived from cells that can be treated with a platinum compound of the present invention include, but are not limited to: interferons, interleukins, blood clotting factors such as factor VIII, IX, X, and the like, insulin, polyclonal and monoclonal antibodies, growth factors, cytokines, and other products. Treatment of biological products comprises contacting the product for an effective amount of time and with an effective amount of a platinum compound of the present invention. If necessary, the biological product can be subsequently washed, preferably with a suitable sterile wash solution such as phosphate buffered saline, to remove the platinum compound that was used to treat the product.

Therapeutic application of the subject platinum compounds, and compositions containing them, can be accomplished by any suitable therapeutic method and technique presently or prospectively known to those skilled in the art. The subject platinum compounds can be administered by any suitable route known in the art including, for example, oral, nasal (e.g., via aerosol inhalant), rectal, ex vivo (reintroduction of treated tissues), and parenteral routes of administration. As used herein, the term parenteral includes topical, subdermal (e.g., as in an implant), subcutaneous, intradermal, intravenous, intramuscular, intraperitoneal, and intrasternal administration, such as by injection. Administration of the subject platinum compounds of the invention can be continuous or at distinct intervals as can be readily determined by a person skilled in the art.

Platinum compounds of the subject invention can be formulated according to known methods for preparing pharmaceutically useful compositions. Formulations are described in detail in a number of sources which are well known and readily available to those skilled in the art. For example, Remington's Pharmaceutical Science by E. W. Martin describes formulations which can be used in connection with the subject invention. In general, the compositions of the subject invention will be formulated such that a bioeffective amount of the platinum compound is combined with a suitable carrier in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, aerosol particle, and sprays. The preferred form depends on the intended mode of administration and therapeutic application. The compositions also preferably include conventional pharmaceutically acceptable carriers and diluents which are known to those skilled in the art. Examples of carriers or diluents for use with the subject platinum compounds include ethanol, ethyl acetate, dimethyl sulfoxide, glycerol, alumina, starch, and equivalent carriers and diluents. To provide for the administration of such dosages for the desired therapeutic treatment, pharmaceutical compositions of the invention will advantageously comprise between about 0.1% and 99%, and especially, 1 and 15% by weight of the total of one or more of the subject platinum compounds based on the weight of the total composition including carrier or diluent.

The platinum compounds of the subject invention can also be administered utilizing liposome technology, antibody-conjugation, peptide-conjugation, nanotechnology (such as carbon nanotubes, gold nanospheres, or nanoslow-release capsules), polymeric sugars, electroporation, implantable pumps, and biodegradable containers. Certain of these delivery methods can, advantageously, provide a uniform dosage over an extended period of time while others provide immediate and/or local targeting. The platinum compounds of the present invention can also be administered in their salt derivative forms or crystalline forms known to those of ordinary skill in the art.

The subject invention also concerns a packaged dosage formulation comprising in one or more containers at least one platinum compound of the subject invention formulated in a pharmaceutically acceptable dosage.

Synthesis of Platinum Compounds

Using 0.300 grams of Transplatin (0.00100 moles, FW=300.1), 150 mL of ultra deionized water are added to a 250-mL Erlenmeyer flask. Additionally, cosolvents such as hexane, dichlorethane or other organic solvents can be added as well. Trans-platinum (II) diammine dichloride (transplatin) can be purchased from Sigma-Aldrich at 99.9% purity (Product No. 1525); cisplatin or other platinum compounds can be used as starting material. The choice of a sixth ligand includes the availability of a nitrogen, sulfur, phosphorous or oxygen atom in the chemical structure providing a Lewis base for bonding to the oxidized Pt. Other ligands are possible with other metals, halides or through chelation or interaction with pi molecular orbitals. One mole of the chosen ligand per mole of cisplatin should be weighed and added to the mixture. Silver nitrate can be added to remove chloride ligands and replace these with other ligands, since silver chloride precipitates are easily separated by filtration. Dichloroethane, e.g., provides solubility for organic ligands of hydrophobic nature and various cosolvents will alter the final crystalline structure and co-crystal structures possible in the final product. A magnetic stir bar is placed in the mixture and the flask placed on a magnetic stir plate in a chemical fume hood. An organic nitrite such as ethylnitrite or butylnitrite; or an inorganic nitrate such as potassium nitrite can be added to oxidize the platinum(II) to platinum(IV). A blue color is noted to indicate formation of the nitrosyl intermediate; variations in hue and duration of this color have been observed. Organic nitrites simplify separation of the final product, since the remaining organic solvent (e.g., ethane for ethylnitrite) can be boiled or evaporated away. The flask should be covered in aluminum foil to prevent light exposure and left to stir overnight. The mixture requires air for complete oxidation, so should not be tightly covered. Continued oxidation with air can be accelerated using air blown through a trap into the Erlenmeyer, over the liquids. The solvents will evaporate in about two days, leaving a yellow (or other color-depending on choice of ligands) precipitate, which is the product.

The precipitate can be purified via recrystallization in methanol, diethyl ether, acetone, or other suitable solvent. Alternatively, the product can be purified on silica-type columns or using HPLC.

All patents, patent applications, provisional applications, and publications referred to or cited herein are incorporated by reference in their entirety, including all figures and tables, to the extent they are not inconsistent with the explicit teachings of this specification. Among those intended to be incorporated by reference are: U.S. Pat. Nos. 7,763,585; 7,759,510; 7,566,798 and 7,238,372; US Patent Applications 2010/0316704, 2010/0310645, 2010/0190180, 2009/0285884, 2009/0214626, 2008/0286316, 2008/0187992, 2007/0161613, 2005/0288365, 2005/0080131 and 2005/0074502; and PCT Applications WO2007/006019, 2005/023824, 2005/016946. WO/2008/144616, WO/2005/023824 and WO/2007/008247.

Methods of Use of a Composition of the Present Invention

A composition of the present invention has a plurality of methods of use, including, but not intended to be limited to:

A method of inhibiting, preventing, or treating cancer metastasis by administering an effective amount of a platinum(IV) compound to a patient to modulate Matrix Metalloproteinases (such as MMP-2 or MMP-9) or Tissue-Inhibitor of Matrix Metalloproteinases (TIMP-1, TIMP-2, TIMP-3 or TIMP-4).

A method of inhibiting or preventing cancer or tumor development associated with viral cell transformations in a patient comprising administering an effective amount of a platinum(IV) compound prophylactically, such as those caused by Human Immunodeficiency Virus-1 in Karposi's Sarcoma; Epstein-Barr Virus in Burkitt's Lymphoma; Hepatitis B or Hepatitis C Viruses in liver cancer; Human Herpes Virus-8 and Simian Virus 40 in lymphomas; Human Papillomavirus (HPV) in cervical cancer, etc.

A method of treatment for in a patient comprising the administration of an effective amount of a platinum(IV) compound for the modulation of Toll-like Receptor (TLR) Signaling Pathways, Tumor Necrosis Factor-alpha (TNF-α) Signaling Pathways, or Nuclear Factor kappaBeta (NF-κB) Pathways.

A method of treatment for in a patient comprising the administration of an effective amount of a platinum(IV) compound for the modulation of Tumor Necrosis Factor-alpha (TNF-α), Activator Protein-1 (AP-1) or Granulocyte-Macrophage Colony-Stimulating Factor (GM-CSF).

A method of use comprising the administration of an effective amount of platinum(IV) compound to a patient to directly modulate Tristetraprolin protein, whereby the platinum(IV) compound interacts with the zinc-binding domain of Tristetraprolin to modulate message RNA lifetimes in the production of cytokines or soluble factors.

A method of use comprising the administration of an effective amount of platinum(IV) compound to a patient for the prevention, treatment, or symptoms associated with infectious diseases of viral, parasitic, bacterial, or prion origin.

A method of use whereby an effective amount of a platinum(IV) compound is administered to a patient alone or in combination with another therapeutic drug whereby drug resistance mechanisms are reduced, such as those involved in Multidrug Resistance (MDR) or upregulation of p53 protein.

A method of use comprising the use of a platinum(IV) compound in a patient to inhibit neurological damage induced by Trans-activator of transcription (Tat) proteins.

A method of use whereby an effective amount of a platinum(IV) compound is administered to a patient to reduce cell migration into the central nervous system associated with leakage of cells across a compromised blood-brain barrier.

A method of use comprising administering an effective therapeutic amount of a platinum(IV) compound to prevent or inhibit the assembly or conformational change of virion or prion particles.

A method of use comprising the administration of an effective amount of a platinum(IV) compound for stabilization of Tat proteins used as transporters, including cargoes of peptides, proteins, drugs, oligonucleotides, imaging agents, nanoparticles, micelles and liposomes.

A method of use as a vaccine adjuvant comprising administering an effective amount of a platinum(IV) compound either in vivo, in vitro, or ex vivo in conjunction with an antigen in order to enhance antigen presentation of the adaptive immune response system in the production of antibodies or vaccines.

A method of use comprising administering an effective amount of a platinum(IV) compound to a patient in the prevention or treatment of autoimmune diseases, whereby the platinum(IV) compound interacts with zinc-binding domains of immune cells.

A method of use comprising the use of a platinum(IV) compound with a virus-infected or virus-transfected cell to produce virus-like particles.

A method of use comprising the administration of an effective amount of a platinum(IV) compound to a patient in vivo or ex vivo to stimulate adaptive, innate or complement immune responses.

A method of use comprising the administration of an effective amount of a platinum(IV) compound to a virus-infected patient to reduce blood plasma viremia, cerebrospinal fluid plasma viremia or proviral load in peripheral blood mononuclear cells.

The following description presents embodiments of the invention representing various modes contemplated for practicing the invention. This description is not to be taken in a limiting sense but is made merely for the purpose of describing the general principles of the invention, whose scope is defined by the appended claims.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components of the invention. This is done merely for convenience and to give a general sense of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable processes and materials are described below. All publications, patent applications, patents, and other references mentioned herein are incorporated by reference in their entirety. In case of conflict, the present specification, including definitions, will control. In addition, the materials, processes, and examples are illustrative only and not intended to be limiting.

The following definitions refer to the particular embodiments described herein and are not to be taken as limiting; the invention includes equivalents for other undescribed embodiments.

As used herein, the term "effective amount" is intended to mean an amount of a platinum(IV) compound that, when administered to a subject, is sufficient to achieve a desirable, comprehensive, or otherwise satisfactory therapeutic response, including without limitation an optimal response and a maximal or near maximal response.

As used herein, the term "pathogen" is intended to mean is a biological agent such as a virus, bacteria, prion, or fungus that causes disease to its host.

As used herein, the term "inhibiting" is intended to mean treating, suppressing or preventing.

As used herein, the term "zinc-binding domain" is intended to mean a protein structural motif that can coordinate zinc ions through a combination of four cysteine (C/Cys) and/or histidine (H/His) residues. Examples of zinc-binding domains include CCCC, CCHC, CHCH and CCHH; spacing of these residues varies and may be denoted by the letter X, indicating any other residue, as for $CX_2CX_4HX_4C$, where the subscript indicates numbers of these. The terms "zinc finger", "zinc-binding motif", "zinc finger domain", "zinc domain", "zinc knuckle" are zinc-binding domains.

As used herein, the term "zinc-binding site" is intended to mean a protein structural motif that can coordinate zinc ions through a combination of residues, not necessarily limited to cysteine and/or histidine; these may include aspartate or glutamate, for example. The term "catalytic domain" of matrix metalloproteinases, for instance, is a zinc-binding site comprised of histidines and glutamatic acid or aspartic acid residues.

As used herein, the term "infection" is intended to mean a clinically manifested state or disease produced by the establishment of an infective agent either in or on a suitable subject or host.

As used herein, the term "subject" is intended to mean one that is acted on during the course of treatment, including without limitation a human or non-human individual awaiting or under medical care and treatment.

As used herein, the term "therapeutic" when referring to a substance or treatment is intended to mean a substance or treatment concerned with providing or assisting in a cure for, or ameliorating the symptoms of, a bodily dysfunction such as that caused by disease or injury.

In the foregoing description, certain terms have been used for brevity, clarity, and understanding, but no unnecessary limitations are to be implied there from beyond the requirements of the prior art, because such words are used for description purposes herein and are intended to be broadly construed. Moreover, the embodiments of the compositions and methods illustrated and described herein are by way of example, and the scope of the invention is not limited to the exact details of structure, synthesis, and use.

Having now described the invention, the operation and use of preferred embodiments thereof, and the advantageous new and useful results obtained thereby, the new and useful constructions, and reasonable equivalents thereof obvious to those skilled in the art, are set forth in the appended claims.

REFERENCES

1. Adamson C S, Salzwedel K, Freed E O. Virus maturation as a new HIV-1 therapeutic target. Expert Opin Ther Targets 13 (8): 895-908, 2009.
2. Aldovini A, Young R A. Mutations of RNA and protein sequences involved in human immunodeficiency virus type 1 packaging result in production of noninfectious virus. J Virol 64 (5): 1920-6, 1990.
3. Alvarez-Lajonchere L, Gonzalez M, Alvarez-Obregon J C, Guerra I, Vina A, Acosta-Rivero N, Musacchio A, Morales J, Duenas-Carrera S. Hepatitis C virus (HCV) core protein enhances the immunogenicity of a co-delivered DNA vaccine encoding HCV structural antigens in mice. Biotechnol Appl Biochem 44 (Pt 1): 9-17, 2006.
4. Amalinei C, Caruntu I D, Balan R A. Biology of metalloproteinases. Rom J Morphol Embryol 48 (4): 323-34, 2007.
5. Amexis G, Young N S. Multiple antigenic peptides as vaccine platform for the induction of humoral responses against dengue-2 virus. Viral Immunol 20 (4): 657-63, 2007.
6. Andras I E, Pu H, Deli M A, Nath A, Hennig B, Toborek M. HIV-1 Tat protein alters tight junction protein expression and distribution in cultured brain endothelial cells. J Neurosci Res 74 (2): 255-65, 2003.
7. Anzellotti A I, Farrell N P. Zinc metalloproteins as medicinal targets. Chem Soc Rev 37 (8): 1629-51, 2008.
8. Anzellotti A I, Liu Q, Bloemink M J, Scarsdale J N, Farrell N. Targeting retroviral Zn finger-DNA interactions: a small-molecule approach using the electrophilic nature of trans-platinum-nucleobase compounds. Chem Biol 13 (5): 539-48, 2006.
9. Anzellotti A I, Sabat M, Farrell N. Covalent and noncovalent interactions for [metal(dien)nucleobase](2+) complexes with L-tryptophan derivatives: formation of palladium-tryptophan species by nucleobase substitution under biologically relevant conditions. Inorg Chem 45 (4): 1638-45, 2006.
10. Arnesano F, Boccarelli A, Cornacchia D, Nushi F, Sasanelli R, Coluccia M, Natile G. Mechanistic insight into the inhibition of matrix metalloproteinases by platinum substrates. J Med Chem 52 (23): 7847-55, 2009.
11. Banks W A, Robinson S M, Nath A. Permeability of the blood-brain barrier to HIV-1 Tat. Exp Neurol 193 (1): 218-27, 2005.
12. Barabas K, Milner R, Lurie D, Adin C. Cisplatin: a review of toxicities and therapeutic applications. Vet Comp Oncol 6 (1): 1-18, 2008.
13. Bednarski P J, Mackay F S, Sadler P J. Photoactivatable platinum complexes. Anticancer Agents Med Chem 7 (1): 75-93, 2007.
14. Beerheide W, Bernard H U, Tan Y J, Ganesan A, Rice W G, Ting A E. Potential drugs against cervical cancer: zinc-ejecting inhibitors of the human papillomavirus type 16 E6 oncoprotein. J Natl Cancer Inst 91 (14): 1211-20, 1999.
15. Berkowitz R, Fisher J, Goff S P. RNA packaging. Curr Top Microbiol Immunol 214: 177-218, 1996.
16. Berthoux L, Pechoux C, Ottmann M, Morel G, Darlix J L. Mutations in the N-terminal domain of human immunodeficiency virus type 1 nucleocapsid protein affect virion core structure and proviral DNA synthesis. J Virol 71 (9): 6973-81, 1997.
17. Biedermannova L, K E R, Berka K, Hobza P, Vondrasek J. Another role of proline: stabilization interactions in proteins and protein complexes concerning proline and tryptophane. Phys Chem Chem Phys 10 (42): 6350-9, 2008.
18. Blasie C A, Berg J M. Toward ligand identification within a CCHHC zinc-binding domain from the NZF/MyT1 family. Inorg Chem 39 (2): 348-51, 2000.
19. Bose R N. Biomolecular targets for platinum antitumor drugs. Mini Rev Med Chem 2 (2): 103-11, 2002.
20. Bose R N, Maurmann L, Mishur R J, Yasui L, Gupta S, Grayburn W S, Hofstetter H, Salley T. Non-DNA-binding platinum anticancer agents: Cytotoxic activities of platinum-phosphato complexes towards human ovarian cancer cells. Proc Natl Acad Sci USA 105 (47): 18314-9, 2008.
21. Brayer K J, Segal D J. Keep your fingers off my DNA: protein-protein interactions mediated by $C_2H_2$ zinc finger domains. Cell Biochem Biophys 50 (3): 111-31, 2008.
22. Breckpot K, Aerts-Toegaert C, Heirman C, Peeters U, Beyaert R, Aerts J L, Thielemans K. Attenuated expression of A20 markedly increases the efficacy of double-stranded RNA-activated dendritic cells as an anti-cancer vaccine. J Immunol 182 (2): 860-70, 2009.
23. Burdette S. trans-Platinum reporting for duty. Chem Biol 13 (5): 465-7, 2006.
24. Burman W J, Gallicano K, Peloquin C. Therapeutic implications of drug interactions in the treatment of human immunodeficiency virus-related tuberculosis. Clin Infect Dis 28 (3): 419-29; quiz 430, 1999.
25. Buttner A, Mehraein P, Weis S. Vascular changes in the cerebral cortex in HIV-1 infection. II. An immunohistochemical and lectinhistochemical investigation. Acta Neuropathol 92 (1): 35-41, 1996.
26. Campbell G R, Loret E P. What does the structure-function relationship of the HIV-1 Tat protein teach us about developing an AIDS vaccine? Retrovirology 6: 50, 2009.
27. Campbell S, Rein A. In vitro assembly properties of human immunodeficiency virus type 1 Gag protein lacking the p6 domain. J Virol 73 (3): 2270-9, 1999.
28. Campbell S M, Crowe S M, Mak J. Lipid rafts and HIV-1: from viral entry to assembly of progeny virions. J Clin Virol 22 (3): 217-27, 2001.
29. Caputo A, Gavioli R, Bellino S, Longo O, Tripiciano A, Francavilla V, Sgadari C, Paniccia G, Titti F, Cafaro A, Ferrantelli F, Monini P, Ensoli F, Ensoli B. HIV-1 Tat-based vaccines: an overview and perspectives in the field of HIV/AIDS vaccine development. Int Rev Immunol 28 (5): 285-334, 2009.
30. Carballo E, Lai W S, Blackshear P J. Evidence that tristetraprolin is a physiological regulator of granulocyte-macrophage colony-stimulating factor messenger RNA deadenylation and stability. Blood 95 (6): 1891-9, 2000.
31. Chandra T, Maier W, Konig H G, Hirzel K, Kogel D, Schuler T, Chandra A, Demirhan I, Laube B. Molecular interactions of the type 1 human immunodeficiency virus transregulatory protein Tat with N-methyl-d-aspartate receptor subunits. Neuroscience 134 (1): 145-53, 2005.
32. Chaudhuri A, Duan F, Morsey B, Persidsky Y, Kanmogne G D. HIV-1 activates proinflammatory and interferon-inducible genes in human brain microvascular endothelial cells: putative mechanisms of blood-brain barrier dysfunction. J Cereb Blood Flow Metab 28 (4): 697-711, 2008.
33. Chen Z L, Strickland S, Neuronal death in the hippocampus is promoted by plasmin-catalyzed degradation of laminin. Cell 91 (7): 917-25, 1997.
34. Chinami M, Inoue M, Masunaga K, Fukuma T, Shingu M, Toyoda T. Nucleic acid binding by zinc finger-like motif of human papillomavirus type 16 E7 oncoprotein. J Virol Methods 59 (1-2): 173-6, 1996.
35. Conant K, McArthur J C, Griffin D E, Sjulson L, Wahl L M, Irani D N. Cerebrospinal fluid levels of MMP-2, 7, and 9 are elevated in association with human immunodeficiency virus dementia. Ann Neurol 46 (3): 391-8, 1999.
36. Creery D, Weiss W, Graziani-Bowering G, Kumar R, Aziz Z, Angel J B, Kumar A. Differential regulation of CXCR4 and CCR5 expression by interleukin (IL)-4 and IL-13 is associated with inhibition of chemotaxis and human immunodeficiency Virus (HIV) type 1 replication but not HIV entry into human monocytes. Viral Immunol 19 (3): 409-23, 2006.
37. Cruceanu M, Gorelick R J, Musier-Forsyth K, Rouzina I, Williams M C. Rapid kinetics of protein-nucleic acid interaction is a major component of HIV-1 nucleocapsid protein's nucleic acid chaperone function. J Mol Biol 363 (5): 867-77, 2006.
38. Cruceanu M, Urbaneja M A, Hixson C V, Johnson D G, Datta S A, Fivash M J, Stephen A G, Fisher R J, Gorelick R J, Casas-Finet J R, Rein A, Rouzina I, Williams M C. Nucleic acid binding and chaperone properties of HIV-1 Gag and nucleocapsid proteins. Nucleic Acids Res 34 (2): 593-605, 2006.
39. Csoma E, Deli T, Konya J, Csernoch L, Beck Z, Gergely L. Human herpesvirus 6A decreases the susceptibility of macrophages to R5 variants of human immunodeficiency virus 1: possible role of RANTES and IL-8. Virus Res 121 (2): 161-8, 2006.

40. Dannull J, Surovoy A, Jung G, Moelling K. Specific binding of HIV-1 nucleocapsid protein to PSI RNA in vitro requires N-terminal zinc finger and flanking basic amino acid residues. Embo J 13 (7): 1525-33, 1994.
41. Darugar Q, Kim H, Gorelick R J, Landes C. Human T-cell lymphotropic virus type 1 nucleocapsid protein-induced structural changes in transactivation response DNA hairpin measured by single-molecule fluorescence resonance energy transfer. J Virol 82 (24): 12164-71, 2008.
42. De Francesco R, Pessi A, Steinkuhler C. Mechanisms of hepatitis C virus NS3 proteinase inhibitors. J Viral Hepat 6 Suppl 1: 23-30, 1999.
43. de Paula Q A, Liu Q, Almaraz E, Denny J A, Mangrum J B, Bhuvanesh N, Darensbourg M Y, Farrell N P. Reactions of palladium and gold complexes with zinc-thiolate chelates using electrospray mass spectrometry and X-ray diffraction: molecular identification of [Pd(bme-dach)], [Au (bme-dach]+ and [ZnCl(bme-dach)]2Pd. Dalton Trans (48): 10896-903, 2009.
44. de Paula Q A, Mangrum J B, Farrell N P. Zinc finger proteins as templates for metal ion exchange: Substitution effects on the C-finger of HIV nucleocapsid NCp7 using M(chelate) species (M=Pt, Pd, Au). J Inorg Biochem 103 (10): 1347-54, 2009.
45. de Rocquigny H, Shvadchak V, Avilov S, Dong C Z, Dietrich U, Darlix J L, Mely Y. Targeting the viral nucleocapsid protein in anti-HIV-1 therapy. Mini Rev Med Chem 8 (1): 24-35, 2008.
46. Deniaud E, Baguet J, Chalard R, Blanquier B, Brinza L, Meunier J, Michallet M C, Laugraud A, Ah-Soon C, Wierinckx A, Castellazzi M, Lachuer J, Gautier C, Marvel J, Leverrier Y. Overexpression of transcription factor Sp1 leads to gene expression perturbations and cell cycle inhibition. PLoS One 4 (9): e7035, 2009.
47. Didierlaurent L, Houzet L, Morichaud Z, Darlix J L, Mougel M. The conserved N-terminal basic residues and zinc-finger motifs of HIV-1 nucleocapsid restrict the viral cDNA synthesis during virus formation and maturation. Nucleic Acids Res 36 (14): 4745-53, 2008.
48. Ding W, Liu W, Cooper K L, Qin X J, de Souza Bergo P L, Hudson L G, Liu K J. Inhibition of poly(ADP-ribose) polymerase-1 by arsenite interferes with repair of oxidative DNA damage. J Biol Chem 284 (11): 6809-17, 2009.
49. Dorfman T, Luban J, Goff S P, Haseltine W A, Gottlinger H G. Mapping of functionally important residues of a cysteine-histidine box in the human immunodeficiency virus type 1 nucleocapsid protein. J Virol 67 (10): 6159-69, 1993.
50. Egele C, Barbier P, Didier P, Piemont E, Allegro D, Chaloin O, Muller S, Peyrot V, Mely Y. Modulation of microtubule assembly by the HIV-1 Tat protein is strongly dependent on zinc binding to Tat. Retrovirology 5: 62, 2008.
51. Elkington P T, Green J A, Friedland J S. Analysis of matrix metalloproteinase secretion by macrophages. Methods Mol Biol 531: 253-65, 2009.
52. Elmowalid G A, Qiao M, Jeong S H, Borg B B, Baumert T F, Sapp R K, Hu Z, Murthy K, Liang T J. Immunization with hepatitis C virus-like particles results in control of hepatitis C virus infection in chimpanzees. Proc Natl Acad Sci USA 104 (20): 8427-32, 2007.
53. Enterlein S, Volchkov V, Weik M, Kolesnikova L, Volchkova V, Klenk H D, Muhlberger E. Rescue of recombinant Marburg virus from cDNA is dependent on nucleocapsid protein VP30. J Virol 80 (2): 1038-43, 2006.
54. Estrada D F, Boudreaux D M, Zhong D, St Jeor S C, De Guzman R N. The Hantavirus Glycoprotein G1 Tail Contains Dual CCHC-type Classical Zinc Fingers. J Biol Chem 284 (13): 8654-60, 2009.

55. Frankel A D, Bredt D S, Pabo C O. Tat protein from human immunodeficiency virus forms a metal-linked dimer. Science 240 (4848): 70-3, 1988.

56. Freed E O. HIV-1 gag proteins: diverse functions in the virus life cycle. Virology 251 (1): 1-15, 1998.

57. Freed E O, Orenstein J M, Buckler-White A J, Martin M A. Single amino acid changes in the human immunodeficiency virus type 1 matrix protein block virus particle production. J Virol 68 (8): 5311-20, 1994.

58. Fruh K, Bartee E, Gouveia K, Mansouri M. Immune evasion by a novel family of viral PHD/LAP-finger proteins of gamma-2 herpesviruses and poxviruses. Virus Res 88 (1-2): 55-69, 2002.

59. Galanski M, Arion V B, Jakupec M A, Keppler B K. Recent developments in the field of tumor-inhibiting metal complexes. Curr Pharm Des 9 (25): 2078-89, 2003.

60. Gallouzi I E, Di Marco S. Tristetraprolin: a weapon against HPV-induced cervical cancer? Aging (Albany N.Y.) 1 (10): 839-41, 2009.

61. Garcia C C, Ellenberg P C, Artuso M C, Scolaro L A, Damonte E B. Characterization of Junin virus particles inactivated by a zinc finger-reactive compound. Virus Res 143 (1): 106-13, 2009.

62. Ghorpade A, Persidskaia R, Suryadevara R, Che M, Liu X J, Persidsky Y, Gendelman H E. Mononuclear phagocyte differentiation, activation, and viral infection regulate matrix metalloproteinase expression: implications for human immunodeficiency virus type 1-associated dementia. J Virol 75 (14): 6572-83, 2001.

63. Gil L, Lopez C, Lazo L, Valdes I, Marcos E, Alonso R, Gambe A, Martin J, Romero Y, Guzman M G, Guillen G, Hermida L. Recombinant nucleocapsid-like particles from dengue-2 virus induce protective CD4+ and CD8+ cells against viral encephalitis in mice. Int Immunol 21 (10): 1175-83, 2009.

64. Gordon S B, Jarman E R, Kanyanda S, French N, Pridmore A C, Zijlstra E E, Molyneux M E, Read R C. Reduced interleukin-8 response to *Streptococcus pneumoniae* by alveolar macrophages from adults with HIV/AIDS. Aids 19 (11): 1197-200, 2005.

65. Gorelick R J, Benveniste R E, Gagliardi T D, Wiltrout T A, Busch L K, Bosche W J, Coren L V, Lifson J D, Bradley P J, Henderson L E, Arthur L O. Nucleocapsid protein zinc-finger mutants of simian immunodeficiency virus strain mne produce virions that are replication defective in vitro and in vivo. Virology 253 (2): 259-70, 1999.

66. Gorelick R J, Gagliardi T D, Bosche W J, Wiltrout T A, Coren L V, Chabot D J, Lifson J D, Henderson L E, Arthur L O. Strict conservation of the retroviral nucleocapsid protein zinc finger is strongly influenced by its role in viral infection processes: characterization of HIV-1 particles containing mutant nucleocapsid zinc-coordinating sequences. Virology 256 (1): 92-104, 1999.

67. Gorelick R J, Nigida S M, Jr., Bess J W, Jr., Arthur L O, Henderson L E, Rein A. Noninfectious human immunodeficiency virus type 1 mutants deficient in genomic RNA. J Virol 64 (7): 3207-11, 1990.

68. Gousset K, Ablan S D, Coren L V, Ono A, Soheilian F, Nagashima K, Ott D E, Freed E O. Real-time visualization of HIV-1 GAG trafficking in infected macrophages. PLoS Pathog 4 (3): e1000015, 2008.

69. Greenstone H L, Nieland J D, de Visser K E, De Bruijn M L, Kirnbauer R, Roden R B, Lowy D R, Kast W M, Schiller JT. Chimeric papillomavirus virus-like particles elicit antitumor immunity against the E7 oncoprotein in an HPV16 tumor model. Proc Natl Acad Sci USA 95 (4): 1800-5, 1998.
70. Guo J, Wu T, Anderson J, Kane B F, Johnson D G, Gorelick R J, Henderson L E, Levin J G. Zinc finger structures in the human immunodeficiency virus type 1 nucleocapsid protein facilitate efficient minus- and plus-strand transfer. J Virol 74 (19): 8980-8, 2000.
71. Guo J, Wu T, Kane B F, Johnson D G, Henderson L E, Gorelick R J, Levin J G. Subtle alterations of the native zinc finger structures have dramatic effects on the nucleic acid chaperone activity of human immunodeficiency virus type 1 nucleocapsid protein. J Virol 76 (9): 4370-8, 2002.
72. Gupta S, Boppana R, Mishra G C, Saha B, Mitra D. Interleukin-12 is necessary for the priming of CD4+ T cells required during the elicitation of HIV-1 gp120-specific cytotoxic T-lymphocyte function. Immunology 124 (4): 553-61, 2008.
73. Hamberger J, Liebeke M, Kaiser M, Bracht K, Olszewski U, Zeillinger R, Hamilton G, Braun D, Bednarski P J. Characterization of chemosensitivity and resistance of human cancer cell lines to platinum(II) versus platinum (IV) anticancer agents. Anticancer Drugs 20 (7): 559-72, 2009.
74. Harney A S, Lee J, Manus L M, Wang P, Ballweg D M, LaBonne C, Meade T J. Targeted inhibition of Snail family zinc finger transcription factors by oligonucleotide-Co(III) Schiff base conjugate. Proc Natl Acad Sci USA 106 (33): 13667-72, 2009.
75. Heinz U, Hemmingsen L, Kiefer M, Adolph H W. Structural adaptability of zinc binding sites: different structures in partially, fully, and heavy-metal loaded states. Chemistry 15 (30): 7350-8, 2009.
76. Herbein G, Varin A, Larbi A, Fortin C, Mahlknecht U, Fulop T, Aggarwal B B. Nef and TNFalpha are coplayers that favor HIV-1 replication in monocytic cells and primary macrophages. Curr HIV Res 6 (2): 117-29, 2008.
77. Hess C, Means T K, Autissier P, Woodberry T, Altfeld M, Addo M M, Frahm N, Brander C, Walker B D, Luster A D. IL-8 responsiveness defines a subset of CD8 T cells poised to kill. Blood 104 (12): 3463-71, 2004.
78. Houzet L, Gay B, Morichaud Z, Briant L, Mougel M. Intracellular assembly and budding of the Murine Leukemia Virus in infected cells. Retrovirology 3: 12, 2006.
79. Houzet L, Morichaud Z, Didierlaurent L, Muriaux D, Darlix J L, Mougel M. Nucleocapsid mutations turn HIV-1 into a DNA-containing virus. Nucleic Acids Res 36 (7): 2311-9, 2008.
80. Huang H W, Wang K T. Structural characterization of the metal binding site in the cysteine-rich region of HIV-1 Tat protein. Biochem Biophys Res Commun 227 (2): 615-21, 1996.
81. Ishida T, Ueda H, Segawa K, Doi M, Inoue M. Prominent stacking interaction with aromatic amino acid by N-quarternization of nucleic acid base: X-ray crystallographic characteristics and biological implications. Arch Biochem Biophys 278 (1): 217-27, 1990.
82. Ivanov A I, Christodoulou J, Parkinson J A, Barnham K J, Tucker A, Woodrow J, Sadler P J. Cisplatin binding sites on human albumin. J Biol Chem 273 (24): 14721-30, 1998.
83. Jacobsen F E, Lewis J A, Cohen S M. The design of inhibitors for medicinally relevant metalloproteins. ChemMedChem 2 (2): 152-71, 2007.
84. Jeong S H, Qiao M, Nascimbeni M, Hu Z, Rehermann B, Murthy K, Liang T J. Immunization with hepatitis C virus-like particles induces humoral and cellular immune responses in nonhuman primates. J Virol 78 (13): 6995-7003, 2004.
85. Johnston J B, Zhang K, Silva C, Shalinsky D R, Conant K, Ni W, Corbett D, Yong V W, Power C. HIV-1 Tat neurotoxicity is prevented by matrix metalloproteinase inhibitors. Ann Neurol 49 (2): 230-41, 2001.
86. Joshi A, Ablan S D, Soheilian F, Nagashima K, Freed E O. Evidence that productive human immunodeficiency virus type 1 assembly can occur in an intracellular compartment. J Virol 83 (11): 5375-87, 2009.
87. Kang S M, Choi J K, Kim S J, Kim J H, Ahn D G, Oh J W. Regulation of hepatitis C virus replication by the core protein through its interaction with viral RNA polymerase. Biochem Biophys Res Commun 386 (1): 55-9, 2009.
88. Kang S M, Song J M, Quan F S, Compans R W. Influenza vaccines based on virus-like particles. Virus Res 143 (2): 140-6, 2009.
89. Kang S M, Yoo D G, Lipatov A S, Song J M, Davis C T, Quan F S, Chen L M, Donis R O, Compans R W. Induction of long-term protective immune responses by influenza H5N1 virus-like particles. PLoS One 4 (3): e4667, 2009.
90. Kesel A J. A system of protein target sequences for anti-RNA-viral chemotherapy by a vitamin B6-derived zinc-chelating trioxa-adamantane-triol. Bioorg Med Chem 11 (21): 4599-613, 2003.
91. Khan R, Giedroc D P. Nucleic acid binding properties of recombinant Zn2 HIV-1 nucleocapsid protein are modulated by COOH-terminal processing. J Biol Chem 269 (36): 22538-46, 1994.
92. Kiernan R E, Freed E O. Cleavage of the murine leukemia virus transmembrane env protein by human immunodeficiency virus type 1 protease: transdominant inhibition by matrix mutations. J Virol 72 (12): 9621-7, 1998.
93. Kim H N, Chung H S. Caveolin-1 inhibits membrane-type 1 matrix metalloproteinase activity. BMB Rep 41 (12): 858-62, 2008.
94. King J E, Eugenin E A, Buckner C M, Berman J W. HIV tat and neurotoxicity. Microbes Infect 8 (5): 1347-57, 2006.
95. Koellensperger G, Daubert S, Erdmann R, Hann S, Rottensteiner H. Characterisation of zinc-binding domains of peroxisomal RING finger proteins using size exclusion chromatography/inductively coupled plasma-mass spectrometry. Biol Chem 388 (11): 1209-14, 2007.
96. Kratochwil N A, Bednarski P J. Relationships between reduction properties and cancer cell growth inhibitory activities of cis-dichloro- and cis-diiodo-Pt(IV)-ethylenediamines. Arch Pharm (Weinheim) 332 (8): 279-85, 1999.
97. Kumar A, Dhawan S, Mukhopadhyay A, Aggarwal B B. Human immunodeficiency virus-1-tat induces matrix metalloproteinase-9 in monocytes through protein tyrosine phosphatase-mediated activation of nuclear transcription factor NF-kappaB. FEBS Lett 462 (1-2): 140-4, 1999.
98. Lai W S, Carballo E, Thorn J M, Kennington E A, Blackshear P J. Interactions of CCCH zinc finger proteins with mRNA. Binding of tristetraprolin-related zinc finger proteins to Au-rich elements and destabilization of mRNA. J Biol Chem 275 (23): 17827-37, 2000.
99. Larabee J L, Hocker J R, Hanas J S. Mechanisms of inhibition of zinc-finger transcription factors by selenium compounds ebselen and selenite. J Inorg Biochem 103 (3): 419-26, 2009.
100. Larabee J L, Hocker J R, Hanas R J, Kahn F M, Hanas J S. Inhibition of zinc finger protein-DNA interactions by sodium selenite. Biochem Pharmacol 64 (12): 1757-65, 2002.

101. Lazo L, Gil L, Lopez C, Valdes I, Marcos E, Alvarez M, Blanco A, Romero Y, Falcon V, Guzman M G, Guillen G, Hermida L. Nucleocapsid-like particles of dengue-2 virus enhance the immune response against a recombinant protein of dengue-4 virus. Arch Virol 155 (10): 1587-95.

102. Li W, Li G, Steiner J, Nath A. Role of Tat protein in HIV neuropathogenesis. Neurotox Res 16 (3): 205-20, 2009.

103. Liang J, Wang J, Azfer A, Song W, Tromp G, Kolattukudy P E, Fu M. A novel CCCH-zinc finger protein family regulates proinflammatory activation of macrophages. J Biol Chem 283 (10): 6337-46, 2008.

104. Liang Y, Ye H, Kang C B, Yoon H S. Domain 2 of nonstructural protein 5A (NS5A) of hepatitis C virus is natively unfolded. Biochemistry 46 (41): 11550-8, 2007.

105. Lindwasser O W, Resh M D. Human immunodeficiency virus type 1 Gag contains a dileucine-like motif that regulates association with multivesicular bodies. J Virol 78 (11): 6013-23, 2004.

106. Lombardi S, Poli A, Massi C, Abramo F, Zaccaro L, Bazzichi A, Malvaldi G, Bendinelli M, Garzelli C. Detection of feline immunodeficiency virus p24 antigen and p24-specific antibodies by monoclonal antibody-based assays. J Virol Methods 46 (3): 287-301, 1994.

107. Luttge B G, Freed E O. FIV Gag: virus assembly and host-cell interactions. Vet Immunol Immunopathol 134 (1-2): 3-13.

108. Manicone A M, McGuire J K. Matrix metalloproteinases as modulators of inflammation. Semin Cell Dev Biol 19 (1): 34-41, 2008.

109. Manrique M L, Gonzalez S A, Affranchino J L. Functional relationship between the matrix proteins of feline and simian immunodeficiency viruses. Virology 329 (1): 157-67, 2004.

110. Manrique M L, Rauddi M L, Gonzalez S A, Affranchino J L. Functional domains in the feline immunodeficiency virus nucleocapsid protein. Virology 327 (1): 83-92, 2004.

111. Marcotrigiano J, Tellinghuisen T. Purification and crystallization of NS5A domain I of hepatitis C virus. Methods Mol Biol 510: 85-94, 2009.

112. Mark-Danieli M, Laham N, Kenan-Eichler M, Castiel A, Melamed D, Landau M, Bouvier N M, Evans M J, Bacharach E. Single point mutations in the zinc finger motifs of the human immunodeficiency virus type 1 nucleocapsid alter RNA binding specificities of the gag protein and enhance packaging and infectivity. J Virol 79 (12): 7756-67, 2005.

113. Markovic M, Knezevic N, Momcilovic M, Grguric-Sipka S, Harhaji L, Trajkovic V, Mostarica Stojkovic M, Sabo T, Miljkovic D. [Pt(HPxSC)Cl(3)], a novel platinum (IV) compound with anticancer properties. Eur J Pharmacol 517 (1-2): 28-34, 2005.

114. Mascarenhas A P, Musier-Forsyth K. The capsid protein of human immunodeficiency virus: interactions of HIV-1 capsid with host protein factors. Febs J 276 (21): 6118-27, 2009.

115. Maynard A T, Covell D G. Reactivity of zinc finger cores: analysis of protein packing and electrostatic screening. J Am Chem Soc 123 (6): 1047-58, 2001.

116. Mellor H R, Snelling S, Hall M D, Modok S, Jaffar M, Hambley T W, Callaghan R. The influence of tumour microenvironmental factors on the efficacy of cisplatin and novel platinum(IV) complexes. Biochem Pharmacol 70 (8): 1137-46, 2005.

117. Misumi S, Takamune N, Ohtsubo Y, Waniguchi K, Shoji S. Zn2+ binding to cysteine-rich domain of extracellular human immunodeficiency virus type 1 Tat protein is associated with Tat protein-induced apoptosis. AIDS Res Hum Retroviruses 20 (3): 297-304, 2004.

118. Mizuno A, Ido E, Goto T, Kuwata T, Nakai M, Hayami M. Mutational analysis of two zinc finger motifs in HIV type 1 nucleocapsid proteins: effects on proteolytic processing of Gag precursors and particle formation. AIDS Res Hum Retroviruses 12 (9): 793-800, 1996.

119. Moradpour D, Brass V, Penin F. Function follows form: the structure of the N-terminal domain of HCV NS5A. Hepatology 42 (3): 732-5, 2005.

120. Morellet N, de Rocquigny H, Mely Y, Jullian N, Demene H, Ottmann M, Gerard D, Darlix J L, Fournie-Zaluski M C, Rogues B P. Conformational behaviour of the active and inactive forms of the nucleocapsid NCp7 of HIV-1 studied by $^1$H NMR. Mol Biol 235 (1): 287-301, 1994.

121. Morellet N, Demene H, Teilleux V, Huynh-Dinh T, de Rocquigny H, Fournie-Zaluski M C, Rogues B P. Structure of the complex between the HIV-1 nucleocapsid protein NCp7 and the single-stranded pentanucleotide d(ACGCC). Mol Biol 283 (2): 419-34, 1998.

122. Morellet N, Meudal H, Bouaziz S, Rogues B P. Structure of the zinc finger domain encompassing residues 13-51 of the nucleocapsid protein from simian immunodeficiency virus. Biochem J 393 (Pt 3): 725-32, 2006.

123. Murata K, Lechmann M, Qiao M, Gunji T, Alter H J, Liang T J. Immunization with hepatitis C virus-like particles protects mice from recombinant hepatitis C virus-vaccinia infection. Proc Natl Acad Sci USA 100 (11): 6753-8, 2003.

124. New E J, Duan R, Zhang J Z, Hambley T W. Investigations using fluorescent ligands to monitor platinum(IV) reduction and platinum(II) reactions in cancer cells. Dalton Trans (16): 3092-101, 2009.

125. Nicastri E, Narciso P, Andreoni M. Initial treatment of HIV-1 infection. N Engl J Med 359 (9): 970-1; author reply 971, 2008.

126. Ottmann M, Gabus C, Darlix J L. The central globular domain of the nucleocapsid protein of human immunodeficiency virus type 1 is critical for virion structure and infectivity. J Virol 69 (3): 1778-84, 1995.

127. Ottmann M, Gabus C, Darlix J L. The central globular domain of the nucleocapsid protein of human immunodeficiency virus type 1 is critical for virion structure and infectivity. J Virol 69 (3): 1778-84, 1995.

128. Paliard X, Liu Y, Wagner R, Wolf H, Baenziger J, Walker C M. Priming of strong, broad, and long-lived HIV type 1 p55gag-specific CD8+ cytotoxic T cells after administration of a virus-like particle vaccine in rhesus macaques. AIDS Res Hum Retroviruses 16 (3): 273-82, 2000.

129. Papasavvas E, Sun J, Luo Q, Moore E C, Thiel B, MacGregor R R, Minty A, Mounzer K, Kostman J R, Montaner L J. IL-13 acutely augments HIV-specific and recall responses from HIV-1-infected subjects in vitro by modulating monocytes. J Immunol 175 (8): 5532-40, 2005.

130. Perera W S, Hooper N M. Ablation of the metal ion-induced endocytosis of the prion protein by disease-associated mutation of the octarepeat region. Curr Biol 11 (7): 519-23, 2001.

131. Peritz A, al-Baker S, Vollano J F, Schurig J E, Bradner W T, Dabrowiak J C. Antitumor and DNA-binding properties of a group of oligomeric complexes of Pt(II) and Pt(IV). J Med Chem 33 (8): 2184-8, 1990.

132. Persidsky Y, Buttini M, Limoges J, Bock P, Gendelman H E. An analysis of HIV-1-associated inflammatory products in brain tissue of humans and SCID mice with HIV-1 encephalitis. J Neurovirol 3 (6): 401-16, 1997.

133. Pistello M, Bonci F, Isola P, Mazzetti P, Merico A, Zaccaro L, Matteucci D, Bendinelli M. Evaluation of feline immunodeficiency virus ORF-A mutants as candidate attenuated vaccine. Virology 332 (2): 676-90, 2005.
134. Poon D T, Wu J, Aldovini A. Charged amino acid residues of human immunodeficiency virus type 1 nucleocapsid p7 protein involved in RNA packaging and infectivity. J Virol 70 (10): 6607-16, 1996.
135. Power C, Kong P A, Crawford T O, Wesselingh S, Glass J D, McArthur J C, Trapp B D. Cerebral white matter changes in acquired immunodeficiency syndrome dementia: alterations of the blood-brain barrier. Ann Neurol 34 (3): 339-50, 1993.
136. Pushko P, Tumpey T M, Bu F, Knell J, Robinson R, Smith G. Influenza virus-like particles comprised of the H A, N A, and M1 proteins of H9N2 influenza virus induce protective immune responses in BALB/c mice. Vaccine 23 (50): 5751-9, 2005.
137. Ramboarina S, Druillennec S, Morellet N, Bouaziz S, Rogues B P. Target specificity of human immunodeficiency virus type 1 NCp7 requires an intact conformation of its CCHC N-terminal zinc finger. J Virol 78 (12): 6682-7, 2004.
138. Ramboarina S, Srividya N, Atkinson R A, Morellet N, Rogues B P, Lefevre J F, Mely Y, Kieffer B. Effects of temperature on the dynamic behaviour of the HIV-1 nucleocapsid NCp7 and its DNA complex. J Mol Biol 316 (3): 611-27, 2002.
139. Rapoport M, Lorberboum-Galski H. TAT-based drug delivery system—new directions in protein delivery for new hopes? Expert Opin Drug Deily 6 (5): 453-63, 2009.
140. Rice W G, Turpin J A, Huang M, Clanton D, Buckheit R W, Jr., Covell D G, Wallqvist A, McDonnell N B, DeGuzman R N, Summers M F, Zalkow L, Bader J P, Haugwitz R D, Sausville E A. Azodicarbonamide inhibits HIV-1 replication by targeting the nucleocapsid protein. Nat Med 3 (3): 341-5, 1997.
141. Riedl P, Buschle M, Reimann J, Schirmbeck R. Binding immune-stimulating oligonucleotides to cationic peptides from viral core antigen enhances their potency as adjuvants. Eur J Immunol 32 (6): 1709-16, 2002.
142. Riedl P, Stober D, Oehninger C, Melber K, Reimann J, Schirmbeck R. Priming Th1 immunity to viral core particles is facilitated by trace amounts of RNA bound to its arginine-rich domain. J Immunol 168 (10): 4951-9, 2002.
143. Sadeyen J R, Tourne S, Shkreli M, Sizaret P Y, Coursaget P. Insertion of a foreign sequence on capsid surface loops of human papillomavirus type 16 virus-like particles reduces their capacity to induce neutralizing antibodies and delineates a conformational neutralizing epitope. Virology 309 (1): 32-40, 2003.
144. Saez R, Echaniz P, De Juan M D, Iribarren J A, Cuadrado E. The impaired response of NK cells from HIV-infected progressor patients to A-class CpG oligodeoxynucleotides is largely dependent of a decreased production of IL-12. Immunol Lett 109 (1): 83-90, 2007.
145. Saini M, Vrati S. A Japanese encephalitis virus peptide present on Johnson grass mosaic virus-like particles induces virus-neutralizing antibodies and protects mice against lethal challenge. J Virol 77 (6): 3487-94, 2003.
146. Schmalzbauer E, Strack B, Dannull J, Guehmann S, Moelling K. Mutations of basic amino acids of NCp7 of human immunodeficiency virus type 1 affect RNA binding in vitro. J Virol 70 (2): 771-7, 1996.
147. Scozzafava A, Casini A, Supuran C T. Targeting cysteine residues of biomolecules: new approaches for the design of antiviral and anticancer drugs. Curr Med Chem 9 (12): 1167-85, 2002.
148. Sedlik C, Saron M, Sarraseca J, Casal I, Leclerc C. Recombinant parvovirus-like particles as an antigen carrier: a novel nonreplicative exogenous antigen to elicit protective antiviral cytotoxic T cells. Proc Natl Acad Sci USA 94 (14): 7503-8, 1997.
149. Sela D, Milman N, Kapeller I, Zick A, Bezalel R, Yaffe N, Shlomai J. Unique characteristics of the kinetoplast DNA replication machinery provide potential drug targets in trypanosomatids. Adv Exp Med Biol 625: 9-21, 2008.
150. Sela D, Yaffe N, Shlomai J. Enzymatic mechanism controls redox-mediated protein-DNA interactions at the replication origin of kinetoplast DNA minicircles. J Biol Chem 283 (46): 32034-44, 2008.
151. Seve M, Favier A, Osman M, Hernandez D, Vaitaitis G, Flores N C, McCord J M, Flores S C. The human immunodeficiency virus-1 Tat protein increases cell proliferation, alters sensitivity to zinc chelator-induced apoptosis, and changes Sp1 DNA binding in HeLa cells. Arch Biochem Biophys 361 (2): 165-72, 1999.
152. Sexton P M, Christopoulos G, Christopoulos A, Nylen E S, Snider R H, Jr., Becker K L. Procalcitonin has bioactivity at calcitonin receptor family complexes: potential mediator implications in sepsis. Crit Care Med 36 (5): 1637-40, 2008.
153. Shresta S, Kyle J L, Robert Beatty P, Harris E. Early activation of natural killer and B cells in response to primary dengue virus infection in NJ mice. Virology 319 (2): 262-73, 2004.
154. Song X T, Evel-Kabler K, Shen L, Rollins L, Huang X F, Chen S Y. A20 is an antigen presentation attenuator, and its inhibition overcomes regulatory T cell-mediated suppression. Nat Med 14 (3): 258-65, 2008.
155. Stevenson P G, Efstathiou S, Doherty P C, Lehner P J. Inhibition of MHC class I-restricted antigen presentation by gamma 2-herpesviruses. Proc Natl Acad Sci USA 97 (15): 8455-60, 2000.
156. Storni T, Ruedl C, Schwarz K, Schwendener R A, Renner W A, Bachmann M F. Nonmethylated C G motifs packaged into virus-like particles induce protective cytotoxic T cell responses in the absence of systemic side effects. J Immunol 172 (3): 1777-85, 2004.
157. Sugrue R J, Fu J, Howe J, Chan Y C. Expression of the dengue virus structural proteins in *Pichia pastoris* leads to the generation of virus-like particles. J Gen Virol 78 (Pt 8): 1861-6, 1997.
158. Sui Z, Sniderhan L F, Schifitto G, Phipps R P, Gelbard H A, Dewhurst S, Maggirwar S B. Functional synergy between CD40 ligand and HIV-1 Tat contributes to inflammation: implications in HIV type 1 dementia. J Immunol 178 (5): 3226-36, 2007.
159. Tacket C O, Sztein M B, Losonsky G A, Wasserman S S, Estes M K. Humoral, mucosal, and cellular immune responses to oral Norwalk virus-like particles in volunteers. Clin Immunol 108 (3): 241-7, 2003.
160. Talbott R L, Sparger E E, Lovelace K M, Fitch W M, Pedersen N C, Luciw P A, Elder J H. Nucleotide sequence and genomic organization of feline immunodeficiency virus. Proc Natl Acad Sci USA 86 (15): 5743-7, 1989.
161. Tallant C, Marrero A, Gomis-Ruth F X. Matrix metalloproteinases: Fold and function of their catalytic domains. Biochim Biophys Acta, 2009.
162. Tanchou V, Decimo D, Pechoux C, Lener D, Rogemond V, Berthoux L, Ottmann M, Darlix J L. Role of the N-terminal zinc finger of human immunodeficiency virus type 1 nucleocapsid protein in virus structure and replication. J Virol 72 (5): 4442-7, 1998.
163. Tedbury P R, Harris M. Characterisation of the role of zinc in the hepatitis C virus NS2/3 auto-cleavage and NS3 protease activities. J Mol Biol 366 (5): 1652-60, 2007.
164. Tellinghuisen T L, Marcotrigiano J, Gorbalenya A E, Rice C M. The NS5A protein of hepatitis C virus is a zinc metalloprotein. J Biol Chem 279 (47): 48576-87, 2004.
165. Thomas J A, Bosche W J, Shatzer T L, Johnson D G, Gorelick R J. Mutations in human immunodeficiency virus type 1 nucleocapsid protein zinc fingers cause premature reverse transcription. J Virol 82 (19): 9318-28, 2008.
166. Thomas J A, Gorelick R J. Nucleocapsid protein function in early infection processes. Virus Res 134 (1-2): 39-63, 2008.
167. Tortorici M A, Ghiringhelli P D, Lozano M E, Albarino C G, Romanowski V. Zinc-binding properties of Junin virus nucleocapsid protein. J Gen Virol 82 (Pt 1): 121-8, 2001.
168. Turkson J, Zhang S, Palmer J, Kay H, Stanko J, Mora L B, Sebti S, Yu H, Jove R. Inhibition of constitutive signal transducer and activator of transcription 3 activation by novel platinum complexes with potent antitumor activity. Mol Cancer Ther 3 (12): 1533-42, 2004.
169. Turner K B, Hagan N A, Fabris D. Inhibitory effects of archetypical nucleic acid ligands on the interactions of HIV-1 nucleocapsid protein with elements of Psi-RNA. Nucleic Acids Res 34 (5): 1305-16, 2006.
170. Valcour V, Sithinamsuwan P, Letendre S, Ances B. Pathogenesis of HIV in the Central Nervous System. Curr HIV/AIDS Rep.
171. Van Lint P, Libert C. Chemokine and cytokine processing by matrix metalloproteinases and its effect on leukocyte migration and inflammation. J Leukoc Biol 82 (6): 1375-81, 2007.
172. Wadia J S, Dowdy S F. Transmembrane delivery of protein and peptide drugs by TAT-mediated transduction in the treatment of cancer. Adv Drug Deily Rev 57 (4): 579-96, 2005.
173. Waheed A A, Ablan S D, Soheilian F, Nagashima K, Ono A, Schaffner C P, Freed E O. Inhibition of human immunodeficiency virus type 1 assembly and release by the cholesterol-binding compound amphotericin B methyl ester: evidence for Vpu dependence. J Virol 82 (19): 9776-81, 2008.
174. Walter E D, Stevens D J, Visconte M P, Millhauser G L. The prion protein is a combined zinc and copper binding protein: Zn2+ alters the distribution of Cu2+ coordination modes. J Am Chem Soc 129 (50): 15440-1, 2007.
175. Warfield K L, Bosio C M, Welcher B C, Deal E M, Mohamadzadeh M, Schmaljohn A, Aman M J, Bavari S. Ebola virus-like particles protect from lethal Ebola virus infection. Proc Natl Acad Sci USA 100 (26): 15889-94, 2003.
176. Webster N L, Crowe S M. Matrix metalloproteinases, their production by monocytes and macrophages and their potential role in HIV-related diseases. J Leukoc Biol 80 (5): 1052-66, 2006.
177. Wiedermann F J, Kaneider N, Egger P, Tiefenthaler W, Wiedermann C J, Lindner K H, Schobersberger W. Migration of human monocytes in response to procalcitonin. Crit Care Med 30 (5): 1112-7, 2002.
178. Williams M C, Gorelick R J, Musier-Forsyth K. Specific zinc-finger architecture required for HIV-1 nucleocapsid protein's nucleic acid chaperone function. Proc Natl Acad Sci USA 99 (13): 8614-9, 2002.
179. Wingard J B, Anderson B, Weissman D. Induction of HIV-specific T and B cell responses with a replicating and conditionally infectious lentiviral vaccine. Eur J Immunol 38 (5): 1310-20, 2008.
180. Younce C W, Azfer A, Kolattukudy P E. MCP-1 (monocyte chemotactic protein-1)-induced protein, a recently identified zinc finger protein, induces adipogenesis in 3T3-L1 pre-adipocytes without peroxisome proliferator-activated receptor gamma. J Biol Chem 284 (40): 27620-8, 2009.
181. Yu Z, Beer C, Koester M, Wirth M. Caveolin-1 interacts with the Gag precursor of murine leukaemia virus and modulates virus production. Virol J 3: 73, 2006.
182. Zhong Y, Smart E J, Weksler B, Couraud P O, Hennig B, Toborek M. Caveolin-1 regulates human immunodeficiency virus-1 Tat-induced alterations of tight junction protein expression via modulation of the Ras signaling. J Neurosci 28 (31): 7788-96, 2008.
183. Zucker S, Drews M, Conner C, Foda H D, DeClerck Y A, Langley K E, Bahou W F, Docherty A J, Cao J. Tissue inhibitor of metalloproteinase-2 (TIMP-2) binds to the catalytic domain of the cell surface receptor, membrane type 1-matrix metalloproteinase 1 (MT1-MMP). J Biol Chem 273 (2): 1216-22, 1998.

That which is claimed is:

1. A method of treating an infection of a viral pathogen in a subject, the method comprising:

administering a platinum (IV) complex effective for treating an infection of a viral pathogen to the subject, the platinum IV complex comprising the structure shown in at least one of formula (II) or (IV):

$$\begin{array}{c} R^1 \\ X_{\prime\prime\prime\prime\prime}|_{\prime\prime\prime\prime}R^3 \\ Pt \\ R^2 \blacktriangleleft | \blacktriangledown Y \\ R^2 \end{array} \quad (II)$$

$$\begin{array}{c} R^1 \\ X_{\prime\prime\prime\prime\prime}|_{\prime\prime\prime\prime}R^3 \\ Pt \\ R^2 \blacktriangleleft | \blacktriangledown Y \\ R^3 \end{array} \quad (IV)$$

wherein:
X and Y are Cl, $R^1$ is —$NO_2$, $R^2$ is Cl, and $R^3$ is —$NH_3$; and
wherein the viral pathogen has one or more zinc-binding domains associated therewith.

2. The method of claim 1 wherein the viral pathogen is a Picornaviridae, poliovirus, human coxsackievirus, hepatitis A virus, Flaviviridae, yellow fever virus, Dengue virus, West Nile virus, Kunjin virus, St. Louis encephalitis virus, hepatitis C virus), Togaviridae rubella virus, Coronaviridae, human coronavirus, human SARS-associated coronavirus, Rhabdoviridae, rabies virus, Paramyxoviridae, human parainfluenza virus, measles virus, human respiratory syncytial virus, Filoviridae, Marburg virus, Ebola virus, Bornaviridae, Borna disease virus, Bunyaviridae, Hantaan virus, Arenaviridae, Lassa virus, Junin virus, Tacaribe virus, Reoviridae human rotavirus, Herpesviridae, HSV-1, HSV-2, Epstein-Barr Virus, Retroviridae, HIV-1, SIV, SHIV, FIV, HTLV-1, MTLV, MMTV, or HIV-2.

* * * * *

UNITED STATES PATENT AND TRADEMARK OFFICE
CERTIFICATE OF CORRECTION

| | |
|---|---|
| PATENT NO. | : 8,895,610 B1 |
| APPLICATION NO. | : 13/011613 |
| DATED | : November 25, 2014 |
| INVENTOR(S) | : Heidi Kay |

Page 1 of 1

It is certified that error appears in the above-identified patent and that said Letters Patent is hereby corrected as shown below:

On the Title Page

Column 1, Item (76):  Delete:
"Heldi Kay, Springfield, VA (US)"

Insert:
-- Heidi Kay, Springfield, VA (US) --

Signed and Sealed this
Third Day of March, 2015

Michelle K. Lee
*Deputy Director of the United States Patent and Trademark Office*

SEQUENCE LISTING

```
<160> NUMBER OF SEQ ID NOS: 17

<210> SEQ ID NO 1
<211> LENGTH: 18
<212> TYPE: PRT
<213> ORGANISM: Human immunodeficiency virus type 1

<400> SEQUENCE: 1

Lys Gly Cys Trp Lys Cys Gly Lys Glu Gly His Gln Met Lys Asp Cys
1               5                   10                  15

Thr Glu

<210> SEQ ID NO 2
<211> LENGTH: 71
<212> TYPE: PRT
<213> ORGANISM: Human immunodeficiency virus type 1
```

<400> SEQUENCE: 2

Ile Gln Lys Gly Asn Phe Arg Asn Gln Arg Lys Thr Val Lys Cys Phe
1               5                   10                  15

Asn Cys Gly Lys Glu Gly His Ile Ala Lys Asn Cys Arg Ala Pro Arg
            20                  25                  30

Lys Lys Gly Cys Trp Lys Cys Gly Lys Glu Gly His Gln Met Lys Asp
        35                  40                  45

Cys Thr Glu Arg Gln Ala Asn Phe Leu Gly Lys Ile Trp Pro Ser His
    50                  55                  60

Lys Gly Arg Pro Gly Asn Phe
65              70

<210> SEQ ID NO 3
<211> LENGTH: 72
<212> TYPE: PRT
<213> ORGANISM: Human immunodeficiency virus type 1

<400> SEQUENCE: 3

Met Gln Arg Gly Asn Phe Arg Asn Gln Arg Lys Asn Val Lys Cys Phe
1               5                   10                  15

Asn Cys Gly Lys Glu Gly His Thr Ala Arg Asn Cys Arg Ala Pro Arg
            20                  25                  30

Lys Lys Gly Cys Trp Lys Cys Gly Lys Glu Gly His Gln Met Lys Asp
        35                  40                  45

Cys Thr Glu Arg Gln Ala Asn Phe Leu Gly Lys Ile Trp Pro Ser Tyr
    50                  55                  60

Lys Gly Arg Pro Gly Asn Phe Leu
65              70

<210> SEQ ID NO 4
<211> LENGTH: 14
<212> TYPE: PRT
<213> ORGANISM: Human immunodeficiency virus type 1

<400> SEQUENCE: 4

Cys Phe Asn Cys Gly Lys Glu Gly His Ile Ala Lys Asn Cys
1               5                   10

<210> SEQ ID NO 5
<211> LENGTH: 14
<212> TYPE: PRT
<213> ORGANISM: Human immunodeficiency virus type 1

<400> SEQUENCE: 5

Cys Trp Asn Cys Gly Lys Glu Gly His Ser Ala Arg Trp Cys
1               5                   10

<210> SEQ ID NO 6
<211> LENGTH: 14
<212> TYPE: PRT
<213> ORGANISM: Human immunodeficiency virus type 1

<400> SEQUENCE: 6

Cys Phe Asn Cys Lys Lys Pro Gly His Leu Ala Arg Gln Cys
1               5                   10

<210> SEQ ID NO 7
<211> LENGTH: 14
<212> TYPE: PRT
<213> ORGANISM: Human immunodeficiency virus type 1

```
<400> SEQUENCE: 7

Cys Trp Lys Cys Gly Lys Glu Gly His Gln Met Lys Asp Cys
1               5                   10

<210> SEQ ID NO 8
<211> LENGTH: 14
<212> TYPE: PRT
<213> ORGANISM: Human immunodeficiency virus type 1

<400> SEQUENCE: 8

Cys Trp Lys Cys Gly Gln Met Gly His Val Met Ala Lys Cys
1               5                   10

<210> SEQ ID NO 9
<211> LENGTH: 14
<212> TYPE: PRT
<213> ORGANISM: Human immunodeficiency virus type 1

<400> SEQUENCE: 9

Cys Asn Lys Cys Gly Lys Pro Gly His Val Ala Ala Lys Cys
1               5                   10

<210> SEQ ID NO 10
<211> LENGTH: 14
<212> TYPE: PRT
<213> ORGANISM: Human immunodeficiency virus type 1

<400> SEQUENCE: 10

Cys Phe Asn Cys Gly Lys Glu Gly His Ile Ala Arg Asn Cys
1               5                   10

<210> SEQ ID NO 11
<211> LENGTH: 14
<212> TYPE: PRT
<213> ORGANISM: Human immunodeficiency virus type 1

<400> SEQUENCE: 11

Cys Phe Asn Cys Gly Lys Glu Gly His Leu Ala Arg Asn Cys
1               5                   10

<210> SEQ ID NO 12
<211> LENGTH: 14
<212> TYPE: PRT
<213> ORGANISM: Human immunodeficiency virus type 1

<400> SEQUENCE: 12

Cys Phe Asn Cys Gly Lys Glu Gly His Ile Ala Lys Asn Cys
1               5                   10

<210> SEQ ID NO 13
<211> LENGTH: 14
<212> TYPE: PRT
<213> ORGANISM: Human immunodeficiency virus type 1

<400> SEQUENCE: 13

Cys Phe Asn Cys Gly Lys Asp Gly His Leu Ala Arg Asn Cys
1               5                   10

<210> SEQ ID NO 14
<211> LENGTH: 14
<212> TYPE: PRT
<213> ORGANISM: Human immunodeficiency virus type 1

<400> SEQUENCE: 14
```

-continued

```
Cys Trp Lys Cys Gly Lys Glu Gly His Gln Met Lys Asp Cys
1               5                   10
```

<210> SEQ ID NO 15
<211> LENGTH: 14
<212> TYPE: PRT
<213> ORGANISM: Human immunodeficiency virus type 1

<400> SEQUENCE: 15

```
Cys Trp Lys Cys Gly Arg Glu Gly His Gln Met Lys Asp Cys
1               5                   10
```

<210> SEQ ID NO 16
<211> LENGTH: 101
<212> TYPE: PRT
<213> ORGANISM: Human immunodeficiency virus type 1

<400> SEQUENCE: 16

```
Met Glu Pro Val Asp Pro Arg Leu Glu Pro Trp Lys His Pro Gly Ser
1               5                   10                  15

Gln Pro Lys Thr Pro Cys Thr Lys Cys Tyr Cys Lys Lys Cys Cys Leu
            20                  25                  30

His Cys Gln Val Cys Phe Met Thr Lys Gly Leu Gly Ile Ser Tyr Gly
        35                  40                  45

Arg Lys Lys Arg Arg Gln Arg Arg Ala Pro Gln Asp Asn Lys Asn
    50                  55                  60

His Gln Val Ser Leu Ser Lys Gln Pro Thr Ser Arg Ala Arg Gly Asp
65                  70                  75                  80

Pro Thr Gly Gln Glu Glu Ser Lys Glu Lys Val Glu Lys Glu Thr Val
                85                  90                  95

Val Asp Pro Val Thr
            100
```

<210> SEQ ID NO 17
<211> LENGTH: 8
<212> TYPE: PRT
<213> ORGANISM: Artificial Sequence
<220> FEATURE:
<223> OTHER INFORMATION: synthetic peptide

<400> SEQUENCE: 17

```
Pro His Gly Gly Gly Trp Gly Gln
1               5
```